US008388933B2

(12) United States Patent
Leppla et al.

(10) Patent No.: US 8,388,933 B2
(45) Date of Patent: Mar. 5, 2013

(54) MULTIMERIC PROTEIN TOXINS TO TARGET CELLS HAVING MULTIPLE IDENTIFYING CHARACTERISTICS

(75) Inventors: Stephen H. Leppla, Bethesda, MD (US); Shi-Hui Liu, Bethesda, MD (US); Thomas H. Bugge, Bethesda, MD (US)

(73) Assignee: The United States of America as Represented by the Secretary of the Department of Health and Human Services, Washington, DC (US)

( * ) Notice: Subject to any disclaimer, the term of this patent is extended or adjusted under 35 U.S.C. 154(b) by 0 days.

(21) Appl. No.: 13/088,011

(22) Filed: Apr. 15, 2011

(65) Prior Publication Data
US 2011/0280908 A1    Nov. 17, 2011

Related U.S. Application Data

(62) Division of application No. 11/055,557, filed on Feb. 9, 2005, now Pat. No. 7,947,289.

(60) Provisional application No. 60/543,417, filed on Feb. 9, 2004.

(51) Int. Cl.
*A61K 49/00* (2006.01)
*A61K 39/00* (2006.01)
*A61K 39/07* (2006.01)

(52) U.S. Cl. .... 424/9.1; 424/9.2; 424/184.1; 424/185.1; 424/192.1; 424/234.1; 424/246.1; 530/300; 530/350

(58) Field of Classification Search ............. 424/9.1, 424/9.2, 184.1, 185.1, 192.1, 234.1, 246.1; 530/300, 350
See application file for complete search history.

(56) References Cited

U.S. PATENT DOCUMENTS
5,677,274 A    10/1997    Leppla et al.

FOREIGN PATENT DOCUMENTS
WO    WO 01/21656 A2    3/2001
WO    WO 03/033648 A2    4/2003
WO    WO 2004/099254 A2    11/2004

OTHER PUBLICATIONS

Cunningham K., et al.; , *Mapping the lethal factor and edema factor binding sites on oligomeric anthrax protective antigen*, PNAS 2002 99: 7049-7053; 10.1073/pnas.062160399, May 7, 2002, pp. 7049-7053.
Mogridge, J. et al., *The lethal and edema factors of anthrax toxin bind only to oligomeric forms of the protective antigen*, PNAS 2002 99: 7045-7048. 10.1073/pnas.052160199, May 7, 2002, pp. 7045-7048.
Liu, S. et al., *Targeting of Tumor Cells by Cell Surface Urokinase Plasminogen Activator-dependent Anthrax Toxin*, J. Biol. Chem., 276: 17976-17984 : doi:10.1074/jbc.M011085200, May 25, 2001, pp. 17976-17984.
Liu, S. et al.,, *Tumor Cell-selective Cytotoxicity of Matrix Metalloproteinase-activated Anthrax Toxin*, Cancer Res. 2000 60: 6061-6067, Nov. 1, 2000, pp. 6061-6067.
Liu, S. et al.,, *Anthrax toxin: structures, functions and tumour targeting*, Expert Opinion on Biolological Therapy, vol. 3, No. 5. Ashley Publications, Aug. 2003, pp. 843-853.
Liu, S. et al.,, *Intermolecular complementation achieves high-specificity tumor targeting by anthrax toxin*, Nature Biotechnology; doi:10.1038/nbt1091, Nature Publishing Group, May 15, 2005. pp. 1-6.
Frankel, A.E., et al., *Phase I Trial of a Novel Diphtheria Toxin/ Granulocyte Macrophage Colony-stimulalting Factor Fusion Protein (DT388GMCSF) for Refractory or Relapsed Acute Myelod Leukemia*, Clinical Cancer Research vol. 8, May 2002, pp. 1004-1013.
Liu, S. et al.,, *Potent antitumor activity of a urokinase-activated engineered anthrax toxin*, PNAS vol. 100 No. 2, Jan. 21, 2003. pp. 657-662.

*Primary Examiner* — Rodney P. Swartz
(74) *Attorney, Agent, or Firm* — Kilpatrick Townsend & Stockton LLP

(57) ABSTRACT

The present invention provides compositions comprising modified bacterial toxins and methods for using the modified bacterial toxins for targeting particular cell populations and for treating diseases.

18 Claims, 8 Drawing Sheets

FIG. 1

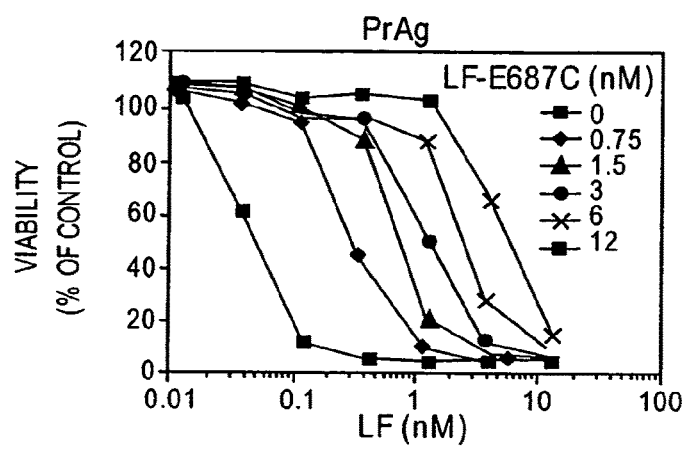
FIG. 4A
FIG. 4B
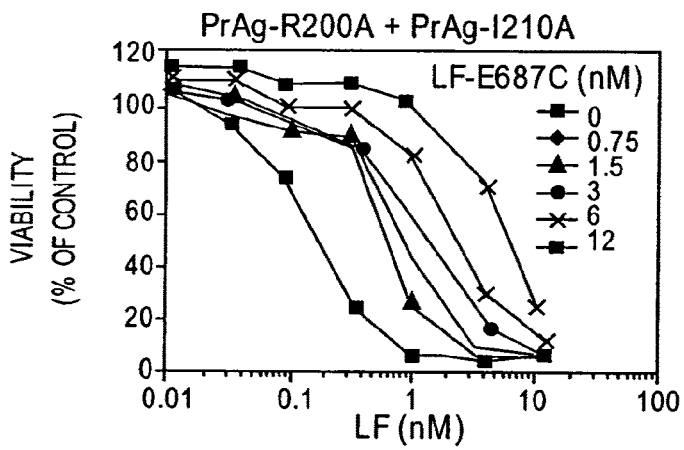
FIG. 4C
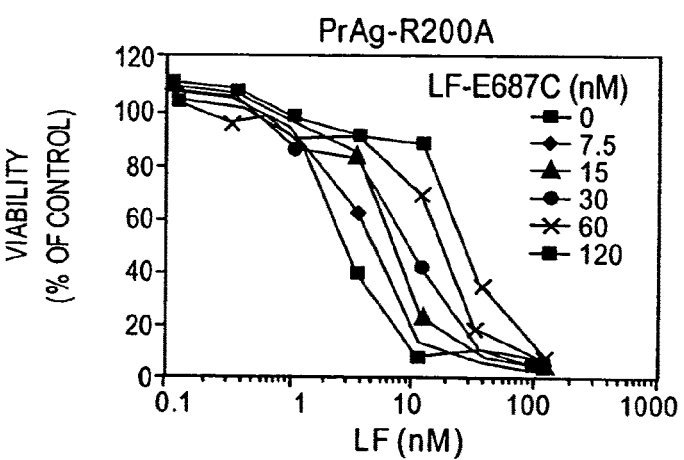
FIG. 4D

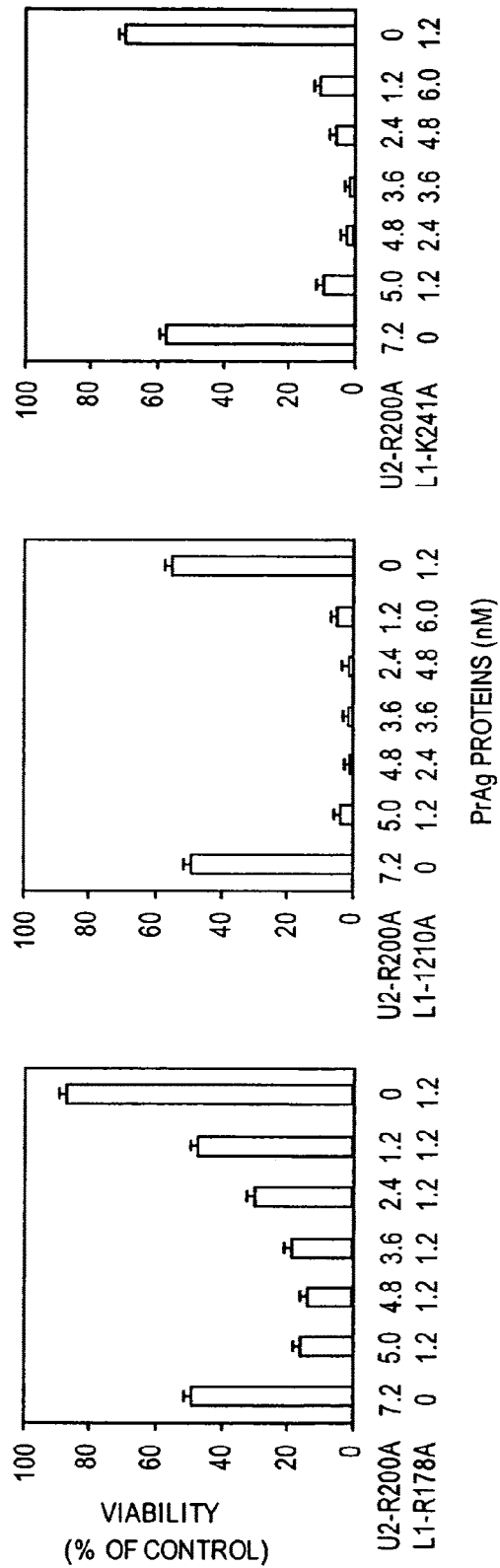
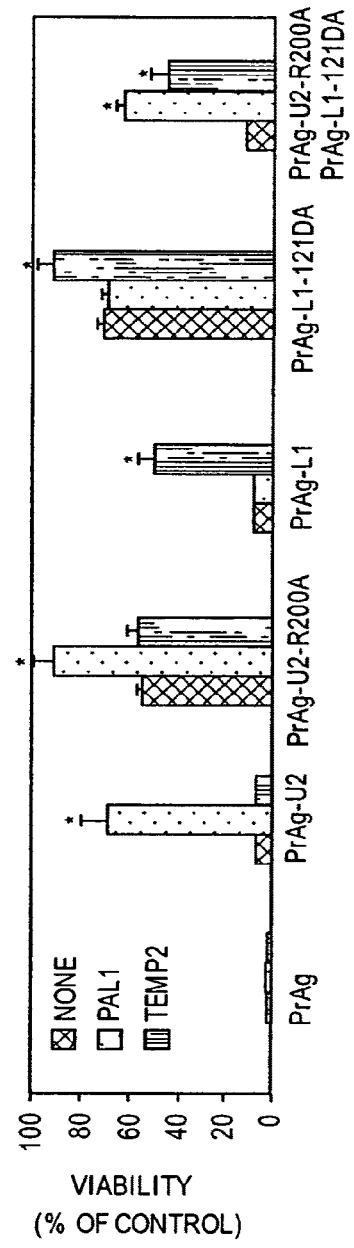
FIG. 5A
FIG. 5B

SEQUENCE LISTING

<160> NUMBER OF SEQ ID NOS: 46

<210> SEQ ID NO 1
<211> LENGTH: 2304
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-U2-R200A

<400> SEQUENCE: 1

```
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa ttttcaagca     180
cccatggtgg ttacctcttc tactacaggg gatttatcta ttcctagttc tgagttagaa     240
aatattccat cggaaaacca atattttcaa tctgctattt ggtcaggatt tatcaaagtt     300
aagaagagtg atgaatatac atttgctact tccgctgata atcatgtaac aatgtgggta     360
gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaaagaag tgatttctag tgataactta     540
caattgccag aattaaaaca aaaatcttcg aactcaccag aagtggaag atcagcaagt     600 acaagtgctg gacctacggt tccagaccgt gacaatgatg gaatccctga ttcattagag     660
gtagaaggat atacggttga tgtcaaaaat aaagcaactt ttctttcacc atggatttct     720
aatattcatg aaaagaaagg attaaccaaa tataaatcat ctcctgaaaa atggagcacg     780
gcttctgatc cgtacagtga tttcgaaaag gttacaggac ggattgataa gaatgtatca     840
ccagaggcaa gacaccccct tgtggcagct tatccgattg tacatgtaga tatggagaat     900
attattctct caaaaaatga ggatcaatcc acacagaata ctgatagtca aacgagaaca     960
ataagtaaaa atacttctac aagtaggaca catactagtg aagtacatgg aaatgcagaa    1020
gtgcatgcgt cgttctttga tattggtggg agtgtatctg caggatttag taattcgaat    1080
tcaagtacgg tcgcaattga tcattcacta tctctagcag gggaaagaac ttgggctgaa    1140
acaatgggtt taaataccgc tgatacagca agattaaatg ccaatattag atatgtaaat    1200
actgggacgc tccaatctcta caacgtgtta ccaacgactt cgttagtgtt aggaaaaaat    1260
caaacactcg cgacaattaa agctaaggaa aaccaattaa gtcaaatact tgcacctaat    1320
aattattatc cttctaaaaa cttggcgcca atcgcattaa atgcacaaga cgatttcagt    1380
tctactccaa ttacaatgaa ttacaatcaa tttcttgagt tagaaaaaac gaaacaatta    1440
agattagata cggatcaagt atatgggaat atagcaacat acaattttga aaatggaaga    1500
gtgagggtgg atacaggctc gaactggagt gaagtgttac cgcaaattca agaaacaact    1560
```

```
gcacgtatca ttttaatgg aaaagattta aatctggtag aaaggcggat agcggcggtt      1620
aatcctagtg atccattaga aacgactaaa ccggatatga cattaaaaga agcccttaaa      1680
atagcatttg gatttaacga accgaatgga aacttacaat atcaagggaa agacataacc      1740
gaatttgatt ttaatttcga tcaacaaaca tctcaaaata tcaagaatca gttagcggaa      1800
ttaaacgcaa ctaacatata tactgtatta gataaaatca aattaaatgc aaaaatgaat      1860
attttaataa gagataaacg ttttcattat gatagaaata acatagcagt tggggcggat      1920
gagtcagtag ttaaggaggc tcatagagaa gtaattaatt cgtcaacaga gggattattg      1980
ttaaatattg ataaggatat aagaaaaata ttatcaggtt atattgtaga aattgaagat      2040
actgaagggc ttaaagaagt tataaatgac agatatgata tgttgaatat ttctagttta      2100
cggcaagatg gaaaaacatt tatagatttt aaaaatata atgataaatt accgttatat       2160
ataagtaatc ccaattataa ggtaaatgta tatgctgtta ctaaagaaaa cactattatt      2220
aatcctagtg agaatgggga tactagtacc aacgggatca agaaaattt aatctttct       2280 aaaaaaggct atgagatagg ataa                                            2304
```

<210> SEQ ID NO 2
<211> LENGTH: 767
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-U2-R200A
<220> FEATURE:
<221> NAME/KEY: SIGNAL
<222> LOCATION: (1)..(29)
<223> OTHER INFORMATION: signal peptide

<400> SEQUENCE: 2

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Pro Gly Ser Gly Arg Ser Ala Ser Thr Ser Ala Gly Pro Thr Val Pro
```

-continued

```
            195                 200                 205
Asp Arg Asp Asn Asp Gly Ile Pro Asp Ser Leu Glu Val Glu Gly Tyr
    210                 215                 220
Thr Val Asp Val Lys Asn Lys Ala Thr Phe Leu Ser Pro Trp Ile Ser
225                 230                 235                 240
Asn Ile His Glu Lys Lys Gly Leu Thr Lys Tyr Lys Ser Ser Pro Glu
                245                 250                 255
Lys Trp Ser Thr Ala Ser Asp Pro Tyr Ser Asp Phe Glu Lys Val Thr
                260                 265                 270
Gly Arg Ile Asp Lys Asn Val Ser Pro Glu Ala Arg His Pro Leu Val
                275                 280                 285
Ala Ala Tyr Pro Ile Val His Val Asp Met Glu Asn Ile Ile Leu Ser
        290                 295                 300
Lys Asn Glu Asp Gln Ser Thr Gln Asn Thr Asp Ser Gln Thr Arg Thr
305                 310                 315                 320
Ile Ser Lys Asn Thr Ser Thr Ser Arg Thr His Thr Ser Glu Val His
                325                 330                 335
Gly Asn Ala Glu Val His Ala Ser Phe Phe Asp Ile Gly Gly Ser Val
                340                 345                 350
Ser Ala Gly Phe Ser Asn Ser Asn Ser Ser Thr Val Ala Ile Asp His
        355                 360                 365
Ser Leu Ser Leu Ala Gly Glu Arg Thr Trp Ala Glu Thr Met Gly Leu
    370                 375                 380
Asn Thr Ala Asp Thr Ala Arg Leu Asn Ala Asn Ile Arg Tyr Val Asn
385                 390                 395                 400
Thr Gly Thr Ala Pro Ile Tyr Asn Val Leu Pro Thr Thr Ser Leu Val
                405                 410                 415
Leu Gly Lys Asn Gln Thr Leu Ala Thr Ile Lys Ala Lys Glu Asn Gln
                420                 425                 430
Leu Ser Gln Ile Leu Ala Pro Asn Asn Tyr Tyr Pro Ser Lys Asn Leu
        435                 440                 445
Ala Pro Ile Ala Leu Asn Ala Gln Asp Asp Phe Ser Ser Thr Pro Ile
    450                 455                 460
Thr Met Asn Tyr Asn Gln Phe Leu Glu Leu Glu Lys Thr Lys Gln Leu
465                 470                 475                 480
Arg Leu Asp Thr Asp Gln Val Tyr Gly Asn Ile Ala Thr Tyr Asn Phe
                485                 490                 495
Glu Asn Gly Arg Val Arg Val Asp Thr Gly Ser Asn Trp Ser Glu Val
                500                 505                 510
Leu Pro Gln Ile Gln Glu Thr Thr Ala Arg Ile Ile Phe Asn Gly Lys
        515                 520                 525
Asp Leu Asn Leu Val Glu Arg Arg Ile Ala Ala Val Asn Pro Ser Asp
    530                 535                 540
Pro Leu Glu Thr Thr Lys Pro Asp Met Thr Leu Lys Glu Ala Leu Lys
545                 550                 555                 560
Ile Ala Phe Gly Phe Asn Glu Pro Asn Gly Asn Leu Gln Tyr Gln Gly
                565                 570                 575
Lys Asp Ile Thr Glu Phe Asp Phe Asn Phe Asp Gln Gln Thr Ser Gln
                580                 585                 590
Asn Ile Lys Asn Gln Leu Ala Glu Leu Asn Ala Thr Asn Ile Tyr Thr
        595                 600                 605
Val Leu Asp Lys Ile Lys Leu Asn Ala Lys Met Asn Ile Leu Ile Arg
    610                 615                 620
```

```
Asp Lys Arg Phe His Tyr Asp Arg Asn Asn Ile Ala Val Gly Ala Asp
625                 630                 635                 640

Glu Ser Val Val Lys Glu Ala His Arg Glu Val Ile Asn Ser Ser Thr
            645                 650                 655

Glu Gly Leu Leu Leu Asn Ile Asp Lys Asp Ile Arg Lys Ile Leu Ser
        660                 665                 670

Gly Tyr Ile Val Glu Ile Glu Asp Thr Glu Gly Leu Lys Glu Val Ile
            675                 680                 685

Asn Asp Arg Tyr Asp Met Leu Asn Ile Ser Ser Leu Arg Gln Asp Gly
        690                 695                 700

Lys Thr Phe Ile Asp Phe Lys Lys Tyr Asn Asp Lys Leu Pro Leu Tyr
705                 710                 715                 720

Ile Ser Asn Pro Asn Tyr Lys Val Asn Val Tyr Ala Val Thr Lys Glu
                725                 730                 735

Asn Thr Ile Ile Asn Pro Ser Glu Asn Gly Asp Thr Ser Thr Asn Gly
            740                 745                 750

Ile Lys Lys Ile Leu Ile Phe Ser Lys Lys Gly Tyr Glu Ile Gly
        755                 760                 765
```

<210> SEQ ID NO 3
<211> LENGTH: 2307
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-L1-I210A (PA-M-I210A)

<400> SEQUENCE: 3

```
atgaaaaaac gaaagtgtt aataccatta atggcattgt ctacgatatt agtttcaagc    60
acaggtaatt tagaggtgat tcaggcagaa gttaaacagg agaaccggtt attaaatgaa   120
tcagaatcaa gttcccaggg gttactagga tactatttta gtgatttgaa ttttcaagca   180
cccatggtgg ttacctcttc tactacaggg gatttatcta ttcctagttc tgagttagaa   240
aatattccat cggaaaacca atattttcaa tctgctattt ggtcaggatt tatcaaagtt   300
aagaagagtg atgaatatac atttgctact tccgctgata atcatgtaac aatgtgggta   360
gatgaccaag aagtgattaa taagcttct aattctaaca aaatcagatt agaaaaagga   420
agattatatc aaataaaaat tcaatatcaa cgagaaaatc ctactgaaaa aggattggat   480
ttcaagttgt actggaccga ttctcaaaat aaaaagaag tgatttctag tgataactta   540
caattgccag aattaaaaca aaaatcttcg aactcaggac cattaggaat gttgagtcaa   600
agtacaagtg ctggacctac ggttccagac cgtgacaatg atggaatccc tgattcatta   660
gaggtagaag atatacggt tgatgtcaaa ataaaagaa cttttctttc accatggatt   720
tctaatgctc atgaaagaa aggattaacc aaatataaat catctcctga aaaatggagc   780
acggcttctg atccgtacag tgatttcgaa aaggttacag gacggattga taagaatgta   840
tcaccagagg caagacaccc ccttgtggca gcttatccga ttgtacatgt agatatggag   900
aatattattc tctcaaaaaa tgaggatcaa tccacacaga atactgatag tcaaacgaga   960
acaataagta aaaatacttc tacaagtagg acacatacta gtgaagtaca tggaaatgca  1020
gaagtgcatg cgtcgttctt tgatattggt gggagtgtat ctgcaggatt tagtaattcg  1080
aattcaagta cggtcgcaat tgatcattca ctatctctag cgggaagg aacttgggct  1140
gaaacaatgg gtttaaatac cgctgataca gcaagattaa atgccaatat tagatatgta  1200
aatactggga cggctccaat ctacaacgtg ttaccaacga cttcgttagt gttaggaaaa  1260
```

-continued

```
aatcaaacac tcgcgacaat taaagctaag gaaaaccaat taagtcaaat acttgcacct   1320
aataattatt atccttctaa aaacttggcg ccaatcgcat taaatgcaca agacgatttc   1380
agttctactc caattacaat gaattacaat caatttcttg agttagaaaa aacgaaacaa   1440
ttaagattag atacggatca agtatatggg aatatagcaa catacaattt tgaaaatgga   1500
agagtgaggg tggatacagg ctcgaactgg agtgaagtgt taccgcaaat tcaagaaaca   1560
actgcacgta tcattttaa tggaaaagat ttaaatctgg tagaaaggcg gatagcggcg   1620
gttaatccta gtgatccatt agaaacgact aaaccggata tgacattaaa agaagccctt   1680
aaaatagcat ttggatttaa cgaaccgaat ggaaacttac aatatcaagg gaaagacata   1740
accgaatttg attttaattt cgatcaacaa acatctcaaa atatcaagaa tcagttagcg   1800
gaattaaacg caactaacat atatactgta ttagataaaa tcaaattaaa tgcaaaaatg   1860
aatattttaa taagagataa acgttttcat tatgatagaa ataacatagc agttggggcg   1920
gatgagtcag tagttaagga ggctcataga gaagtaatta attcgtcaac agagggatta   1980 ttgttaaaata ttgataagga tataagaaaa atattatcag gttatattgt agaaattgaa   2040
gatactgaag ggcttaaaga agttataaat gacagatatg atatgttgaa tatttctagt   2100
ttacggcaag atggaaaaac atttatagat tttaaaaaat ataatgataa attaccgtta   2160
tatataagta atcccaatta taaggtaaat gtatatgctg ttactaaaga aaacactatt   2220
attaatccta gtgagaatgg ggatactagt accaacggga tcaagaaaat tttaatcttt   2280
tctaaaaaag gctatgagat aggataa                                      2307
```

<210> SEQ ID NO 4
<211> LENGTH: 768
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-L1-I210A (PA-M-I210A)
<220> FEATURE:
<221> NAME/KEY: SIGNAL
<222> LOCATION: (1)..(29)
<223> OTHER INFORMATION: signal peptide

<400> SEQUENCE: 4

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140
```

```
Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Gly Pro Leu Gly Met Leu Ser Gln Ser Thr Ser Ala Gly Pro Thr Val
        195                 200                 205

Pro Asp Arg Asp Asn Asp Gly Ile Pro Asp Ser Leu Glu Val Glu Gly
210                 215                 220

Tyr Thr Val Asp Val Lys Asn Lys Arg Thr Phe Leu Ser Pro Trp Ile
225                 230                 235                 240

Ser Asn Ala His Glu Lys Lys Gly Leu Thr Lys Tyr Lys Ser Ser Pro
                245                 250                 255

Glu Lys Trp Ser Thr Ala Ser Asp Pro Tyr Ser Asp Phe Glu Lys Val
            260                 265                 270

Thr Gly Arg Ile Asp Lys Asn Val Ser Pro Glu Ala Arg His Pro Leu
        275                 280                 285

Val Ala Ala Tyr Pro Ile Val His Val Asp Met Glu Asn Ile Ile Leu
290                 295                 300

Ser Lys Asn Glu Asp Gln Ser Thr Gln Asn Thr Asp Ser Gln Thr Arg
305                 310                 315                 320

Thr Ile Ser Lys Asn Thr Ser Thr Ser Arg Thr His Thr Ser Glu Val
                325                 330                 335

His Gly Asn Ala Glu Val His Ala Ser Phe Phe Asp Ile Gly Gly Ser
            340                 345                 350

Val Ser Ala Gly Phe Ser Asn Ser Asn Ser Ser Thr Val Ala Ile Asp
        355                 360                 365

His Ser Leu Ser Leu Ala Gly Glu Arg Thr Trp Ala Glu Thr Met Gly
370                 375                 380

Leu Asn Thr Ala Asp Thr Ala Arg Leu Asn Ala Asn Ile Arg Tyr Val
385                 390                 395                 400

Asn Thr Gly Thr Ala Pro Ile Tyr Asn Val Leu Pro Thr Thr Ser Leu
                405                 410                 415

Val Leu Gly Lys Asn Gln Thr Leu Ala Thr Ile Lys Ala Lys Glu Asn
            420                 425                 430

Gln Leu Ser Gln Ile Leu Ala Pro Asn Asn Tyr Tyr Pro Ser Lys Asn
        435                 440                 445

Leu Ala Pro Ile Ala Leu Asn Ala Gln Asp Asp Phe Ser Ser Thr Pro
450                 455                 460

Ile Thr Met Asn Tyr Asn Gln Phe Leu Glu Leu Glu Lys Thr Lys Gln
465                 470                 475                 480

Leu Arg Leu Asp Thr Asp Gln Val Tyr Gly Asn Ile Ala Thr Tyr Asn
                485                 490                 495

Phe Glu Asn Gly Arg Val Arg Val Asp Thr Gly Ser Asn Trp Ser Glu
            500                 505                 510

Val Leu Pro Gln Ile Gln Glu Thr Thr Ala Arg Ile Ile Phe Asn Gly
        515                 520                 525

Lys Asp Leu Asn Leu Val Glu Arg Arg Ile Ala Ala Val Asn Pro Ser
530                 535                 540

Asp Pro Leu Glu Thr Thr Lys Pro Asp Met Thr Leu Lys Glu Ala Leu
545                 550                 555                 560

Lys Ile Ala Phe Gly Phe Asn Glu Pro Asn Gly Asn Leu Gln Tyr Gln
                565                 570                 575
```

```
Gly Lys Asp Ile Thr Glu Phe Asp Phe Asn Phe Asp Gln Gln Thr Ser
            580                 585                 590

Gln Asn Ile Lys Asn Gln Leu Ala Glu Leu Asn Ala Thr Asn Ile Tyr
        595                 600                 605

Thr Val Leu Asp Lys Ile Lys Leu Asn Ala Lys Met Asn Ile Leu Ile
    610                 615                 620

Arg Asp Lys Arg Phe His Tyr Asp Arg Asn Asn Ile Ala Val Gly Ala
625                 630                 635                 640

Asp Glu Ser Val Val Lys Glu Ala His Arg Glu Val Ile Asn Ser Ser
                645                 650                 655

Thr Glu Gly Leu Leu Leu Asn Ile Asp Lys Asp Ile Arg Lys Ile Leu
            660                 665                 670

Ser Gly Tyr Ile Val Glu Ile Glu Asp Thr Glu Gly Leu Lys Glu Val
        675                 680                 685

Ile Asn Asp Arg Tyr Asp Met Leu Asn Ile Ser Ser Leu Arg Gln Asp
    690                 695                 700

Gly Lys Thr Phe Ile Asp Phe Lys Lys Tyr Asn Asp Lys Leu Pro Leu
705                 710                 715                 720

Tyr Ile Ser Asn Pro Asn Tyr Lys Val Asn Val Tyr Ala Val Thr Lys
                725                 730                 735

Glu Asn Thr Ile Ile Asn Pro Ser Glu Asn Gly Asp Thr Ser Thr Asn
            740                 745                 750

Gly Ile Lys Lys Ile Leu Ile Phe Ser Lys Lys Gly Tyr Glu Ile Gly
        755                 760                 765

<210> SEQ ID NO 5
<211> LENGTH: 2307
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-L1-K214A (PA-M-K214A)

<400> SEQUENCE: 5
atgaaaaaac gaaaagtgtt aataccatta atggcattgt ctacgatatt agtttcaagc    60
acaggtaatt tagaggtgat tcaggcagaa gttaaacagg agaaccggtt attaaatgaa   120
tcagaatcaa gttcccaggg gttactagga tactatttta gtgatttgaa ttttcaagca   180
cccatggtgg ttacctcttc tactacaggg gatttatcta ttcctagttc tgagttagaa   240
aatattccat cggaaaacca atattttcaa tctgctattt ggtcaggatt tatcaaagtt   300
aagaagagtg atgaatatac atttgctact tccgctgata tcatgtaac aatgtgggta   360 gatgaccaag aagtgattaa taaagcttct aattctaaca aaatcagatt agaaaaagga   420
agattatatc aaataaaaat tcaatatcaa cgagaaaatc ctactgaaaa aggattggat   480
ttcaagttgt actggaccga ttctcaaaat aaaaaagaag tgatttctag tgataactta   540
caattgccag aattaaaaca aaaatcttcg aactcaggac cattaggaat gttgagtcaa   600
agtacaagtg ctggacctac ggttccagac cgtgacaatg atggaatccc tgattcatta   660
gaggtagaag gatatacggt tgatgtcaaa aataaaagaa ctttctcttt accatggatt   720
tctaatattc atgaaaaggc aggattaacc aaatataaat catctcctga aaatggagc    780 acggcttctg atccgtacag tgatttcgaa aaggttacag gacggattga taagaatgta   840
tcaccagagg caagacaccc ccttgtggca gcttatccga ttgtacatgt agatatggag   900
aatattattc tctcaaaaaa tgaggatcaa tccacacaga atactgatag tcaaacgaga   960
```

-continued

```
acaataagta aaaatacttc tacaagtagg acacatacta gtgaagtaca tggaaatgca    1020
gaagtgcatg cgtcgttctt tgatattggt gggagtgtat ctgcaggatt tagtaattcg    1080
aattcaagta cggtcgcaat tgatcattca ctatctctag caggggaaag aacttgggct    1140
gaaacaatgg gtttaaatac cgctgataca gcaagattaa atgccaatat tagatatgta    1200
aatactggga cggctccaat ctacaacgtg ttaccaacga cttcgttagt gttaggaaaa    1260
aatcaaacac tcgcgacaat taaagctaag gaaaaccaat taagtcaaat acttgcacct    1320
aataattatt atccttctaa aaacttggcg ccaatcgcat aaatgcaca agacgatttc     1380 agttctactc caattacaat gaattacaat caatttcttg agttagaaaa aacgaaacaa    1440
ttaagattag atacggatca agtatatggg aatatagcaa catacaattt tgaaaatgga    1500
agagtgaggg tggatacagg ctcgaactgg agtgaagtgt taccgcaaat tcaagaaaca    1560
actgcacgta tcatttttaa tggaaaagat ttaaatctgg tagaaaggcg gatagcggcg    1620
gttaatccta gtgatccatt agaaacgact aaaccggata tgacattaaa agaagccctt    1680
aaaatagcat ttggatttaa cgaaccgaat ggaaacttac aatatcaagg gaaagacata    1740
accgaatttg attttaattt cgatcaacaa acatctcaaa atatcaagaa tcagttagcg    1800
gaattaaacg caactaacat atatactgta ttagataaaa tcaaattaaa tgcaaaaatg    1860
aatattttaa taagagataa acgttttcat tatgatagaa ataacatagc agttggggcg    1920
gatgagtcag tagttaagga ggctcataga gaagtaatta attcgtcaac agagggatta    1980
ttgttaaata ttgataagga tataagaaaa atattatcag gttatattgt agaaattgaa    2040
gatactgaag ggcttaaaga agttataaat gacagatatg atatgttgaa tatttctagt    2100
ttacggcaag atggaaaaac atttatagat tttaaaaaat ataatgataa attaccgtta    2160
tatataagta atcccaatta taaggtaaat gtatatgctg ttactaaaga aaacactatt    2220
attaatccta gtgagaatgg ggatactagt accaacggga tcaagaaaat tttaatctttt   2280 tctaaaaaag gctatgagat aggataa                                       2307
```

<210> SEQ ID NO 6
<211> LENGTH: 768
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-L1-K214A (PA-M-K214A)
<220> FEATURE:
<221> NAME/KEY: SIGNAL
<222> LOCATION: (1)..(29)
<223> OTHER INFORMATION: signal peptide

<400> SEQUENCE: 6

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95
```

-continued

Phe Ile Lys Val Lys Lys Ser Asp Glu Tyr Thr Phe Ala Thr Ser Ala
                100                 105                 110

Asp Asn His Val Thr Met Trp Val Asp Asp Gln Glu Val Ile Asn Lys
            115                 120                 125

Ala Ser Asn Ser Asn Lys Ile Arg Leu Glu Lys Gly Arg Leu Tyr Gln
        130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Gly Pro Leu Gly Met Leu Ser Gln Ser Thr Ser Ala Gly Pro Thr Val
        195                 200                 205

Pro Asp Arg Asp Asn Asp Gly Ile Pro Asp Ser Leu Glu Val Glu Gly
    210                 215                 220

Tyr Thr Val Asp Val Lys Asn Lys Arg Thr Phe Leu Ser Pro Trp Ile
225                 230                 235                 240

Ser Asn Ile His Glu Lys Ala Gly Leu Thr Lys Tyr Lys Ser Ser Pro
                245                 250                 255

Glu Lys Trp Ser Thr Ala Ser Asp Pro Tyr Ser Asp Phe Glu Lys Val
            260                 265                 270

Thr Gly Arg Ile Asp Lys Asn Val Ser Pro Glu Ala Arg His Pro Leu
        275                 280                 285

Val Ala Ala Tyr Pro Ile Val His Val Asp Met Glu Asn Ile Ile Leu
    290                 295                 300

Ser Lys Asn Glu Asp Gln Ser Thr Gln Asn Thr Asp Ser Gln Thr Arg
305                 310                 315                 320

Thr Ile Ser Lys Asn Thr Ser Thr Ser Arg Thr His Thr Ser Glu Val
                325                 330                 335

His Gly Asn Ala Glu Val His Ala Ser Phe Phe Asp Ile Gly Gly Ser
            340                 345                 350

Val Ser Ala Gly Phe Ser Asn Ser Asn Ser Ser Thr Val Ala Ile Asp
        355                 360                 365

His Ser Leu Ser Leu Ala Gly Glu Arg Thr Trp Ala Glu Thr Met Gly
    370                 375                 380

Leu Asn Thr Ala Asp Thr Ala Arg Leu Asn Ala Asn Ile Arg Tyr Val
385                 390                 395                 400

Asn Thr Gly Thr Ala Pro Ile Tyr Asn Val Leu Pro Thr Thr Ser Leu
                405                 410                 415

Val Leu Gly Lys Asn Gln Thr Leu Ala Thr Ile Lys Ala Lys Glu Asn
            420                 425                 430

Gln Leu Ser Gln Ile Leu Ala Pro Asn Tyr Tyr Pro Ser Lys Asn
        435                 440                 445

Leu Ala Pro Ile Ala Leu Asn Ala Gln Asp Asp Phe Ser Ser Thr Pro
    450                 455                 460

Ile Thr Met Asn Tyr Asn Gln Phe Leu Glu Leu Glu Lys Thr Lys Gln
465                 470                 475                 480

Leu Arg Leu Asp Thr Asp Gln Val Tyr Gly Asn Ile Ala Thr Tyr Asn
                485                 490                 495

Phe Glu Asn Gly Arg Val Arg Val Asp Thr Gly Ser Asn Trp Ser Glu
            500                 505                 510

Val Leu Pro Gln Ile Gln Glu Thr Thr Ala Arg Ile Ile Phe Asn Gly

|     |     |     |     | 515 |     |     |     | 520 |     |     |     | 525 |     |     |
| --- | --- | --- | --- | --- | --- | --- | --- | --- | --- | --- | --- | --- | --- | --- |

Lys Asp Leu Asn Leu Val Glu Arg Arg Ile Ala Ala Val Asn Pro Ser
530                     535                     540

Asp Pro Leu Glu Thr Thr Lys Pro Asp Met Thr Leu Lys Glu Ala Leu
545                     550                     555                     560

Lys Ile Ala Phe Gly Phe Asn Glu Pro Asn Gly Asn Leu Gln Tyr Gln
                        565                     570                     575

Gly Lys Asp Ile Thr Glu Phe Asp Phe Asn Phe Asp Gln Gln Thr Ser
                        580                     585                     590

Gln Asn Ile Lys Asn Gln Leu Ala Glu Leu Asn Ala Thr Asn Ile Tyr
                        595                     600                     605

Thr Val Leu Asp Lys Ile Lys Leu Asn Ala Lys Met Asn Ile Leu Ile
                        610                     615                     620

Arg Asp Lys Arg Phe His Tyr Asp Arg Asn Asn Ile Ala Val Gly Ala
625                     630                     635                     640

Asp Glu Ser Val Val Lys Glu Ala His Arg Glu Val Ile Asn Ser Ser
                        645                     650                     655

Thr Glu Gly Leu Leu Leu Asn Ile Asp Lys Asp Ile Arg Lys Ile Leu
                        660                     665                     670

Ser Gly Tyr Ile Val Glu Ile Glu Asp Thr Glu Gly Leu Lys Glu Val
                        675                     680                     685

Ile Asn Asp Arg Tyr Asp Met Leu Asn Ile Ser Ser Leu Arg Gln Asp
690                     695                     700

Gly Lys Thr Phe Ile Asp Phe Lys Lys Tyr Asn Asp Lys Leu Pro Leu
705                     710                     715                     720

Tyr Ile Ser Asn Pro Asn Tyr Lys Val Asn Val Tyr Ala Val Thr Lys
                        725                     730                     735

Glu Asn Thr Ile Ile Asn Pro Ser Glu Asn Gly Asp Thr Ser Thr Asn
                        740                     745                     750

Gly Ile Lys Lys Ile Leu Ile Phe Ser Lys Lys Gly Tyr Glu Ile Gly
                        755                     760                     765

<210> SEQ ID NO 7
<211> LENGTH: 2307
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-L1-R178A (PA-M-R178A)

<400> SEQUENCE: 7

```
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga ctatttta gtgatttgaa ttttcaagca      180
cccatggtgg ttacctcttc tactacaggg gatttatcta ttcctagttc tgagttagaa     240
aatattccat cggaaaacca atattttcaa tctgctattt ggtcaggatt tatcaaagtt     300
aagaagagtg atgaatatac atttgctact tccgctgata tcatgtaac aatgtgggta     360
gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaagaag tgatttctag tgataactta     540
caattgccag aattaaaaca aaatcttcg aactcaggac cattaggaat gttgagtcaa     600
agtacaagtg ctggacctac ggttccagac gctgacaatg atgggatccc tgattcatta     660
```

```
gaggtagaag gatatacggt tgatgtcaaa aataaaagaa cttttctttc accatggatt    720
tctaatattc atgaaaagaa aggattaacc aaatataaat catctcctga aaatggagc     780 acggcttctg atccgtacag tgatttcgaa aaggttacag gacggattga taagaatgta    840
tcaccagagg caagacaccc ccttgtggca gcttatccga ttgtacatgt agatatggag    900
aatattattc tctcaaaaaa tgaggatcaa tccacacaga atactgatag tcaaacgaga    960
acaataagta aaaatacttc tacaagtagg acacatacta gtgaagtaca tggaaatgca   1020
gaagtgcatg cgtcgttctt tgatattggt gggagtgtat ctgcaggatt tagtaattcg   1080
aattcaagta cggtcgcaat tgatcattca ctatctctag caggggaaag aacttgggct   1140
gaaacaatgg gtttaaatac cgctgataca gcaagattaa atgccaatat tagatatgta   1200
aatactggga cggctccaat ctacaacgtg ttaccaacga cttcgttagt gttaggaaaa   1260
aatcaaacac tcgcgacaat taaagctaag gaaaaccaat taagtcaaat acttgcacct   1320
aataattatt atccttctaa aaacttggcg ccaatcgcat taaatgcaca agacgatttc   1380
agttctactc caattacaat gaattacaat caatttcttg agttagaaaa aacgaaacaa   1440
ttaagattag atacggatca agtatatggg aatatagcaa catacaattt tgaaaatgga   1500
agagtgaggg tggatacagg ctcgaactgg agtgaagtgt taccgcaaat tcaagaaaca   1560
actgcacgta tcattttaa tggaaaagat ttaaatctgg tagaaaggcg gatagcggcg   1620
gttaatccta gtgatccatt agaaacgact aaaccggata tgacattaaa agaagccctt   1680
aaaatagcat ttggatttaa cgaaccgaat ggaaacttac aatatcaagg gaaagacata   1740
accgaatttg attttaattt cgatcaacaa acatctcaaa atatcaagaa tcagttagcg   1800
gaattaaacg caactaacat atatactgta ttagataaaa tcaaattaaa tgcaaaaatg   1860
aatattttaa taagagataa acgttttcat tatgatagaa ataacatagc agttggggcg   1920
gatgagtcag tagttaagga ggctcataga gaagtaatta ttcgtcaac agagggatta   1980 ttgttaaata ttgataagga tataagaaaa atattatcag gttatattgt agaaattgaa   2040
gatactgaag ggcttaaaga agttataaat gacagatatg atatgttgaa tatttctagt   2100
ttacggcaag atggaaaaac atttatagat tttaaaaaat ataatgataa attaccgtta   2160
tatataagta atcccaatta taaggtaaat gtatatgctg ttactaaaga aaacactatt   2220
attaatccta gtgagaatgg ggatactagt accaacggga tcaagaaaat tttaatcttt   2280
tctaaaaaag gctatgagat aggataa                                        2307
```

<210> SEQ ID NO 8
<211> LENGTH: 768
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-L1-R178A (PA-M-R178A)
<220> FEATURE:
<221> NAME/KEY: SIGNAL
<222> LOCATION: (1)..(29)
<223> OTHER INFORMATION: signal peptide

<400> SEQUENCE: 8

Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu

```
                35              40              45
Leu Gly Tyr Tyr Phe Ser Asp Leu Asn Phe Gln Ala Pro Met Val Val
         50              55              60
Thr Ser Ser Thr Thr Gly Asp Leu Ser Ile Pro Ser Ser Glu Leu Glu
 65              70              75              80
Asn Ile Pro Ser Glu Asn Gln Tyr Phe Gln Ser Ala Ile Trp Ser Gly
                 85              90              95
Phe Ile Lys Val Lys Ser Asp Glu Tyr Thr Phe Ala Thr Ser Ala
             100             105             110
Asp Asn His Val Thr Met Trp Val Asp Gln Glu Val Ile Asn Lys
             115             120             125
Ala Ser Asn Ser Asn Lys Ile Arg Leu Glu Lys Gly Arg Leu Tyr Gln
     130             135             140
Ile Lys Ile Gln Tyr Gln Arg Glu Asn Pro Thr Glu Lys Gly Leu Asp
145             150             155             160
Phe Lys Leu Tyr Trp Thr Asp Ser Gln Asn Lys Lys Glu Val Ile Ser
                 165             170             175
Ser Asp Asn Leu Gln Leu Pro Glu Leu Lys Gln Lys Ser Ser Asn Ser
         180             185             190
Gly Pro Leu Gly Met Leu Ser Gln Ser Thr Ser Ala Gly Pro Thr Val
         195             200             205
Pro Asp Ala Asp Asn Asp Gly Ile Pro Asp Ser Leu Glu Val Glu Gly
 210             215             220
Tyr Thr Val Asp Val Lys Asn Lys Arg Thr Phe Leu Ser Pro Trp Ile
225             230             235             240
Ser Asn Ile His Glu Lys Lys Gly Leu Thr Lys Tyr Lys Ser Pro
                 245             250             255
Glu Lys Trp Ser Thr Ala Ser Asp Pro Tyr Ser Asp Phe Glu Lys Val
         260             265             270
Thr Gly Arg Ile Asp Lys Asn Val Ser Pro Glu Ala Arg His Pro Leu
         275             280             285
Val Ala Ala Tyr Pro Ile Val His Val Asp Met Glu Asn Ile Ile Leu
 290             295             300
Ser Lys Asn Glu Asp Gln Ser Thr Gln Asn Thr Asp Ser Gln Thr Arg
305             310             315             320
Thr Ile Ser Lys Asn Thr Ser Thr Ser Arg Thr His Thr Ser Glu Val
                 325             330             335
His Gly Asn Ala Glu Val His Ala Ser Phe Phe Asp Ile Gly Gly Ser
         340             345             350
Val Ser Ala Gly Phe Ser Asn Ser Asn Ser Ser Thr Val Ala Ile Asp
         355             360             365
His Ser Leu Ser Leu Ala Gly Glu Arg Thr Trp Ala Glu Thr Met Gly
         370             375             380
Leu Asn Thr Ala Asp Thr Ala Arg Leu Asn Ala Asn Ile Arg Tyr Val
385             390             395             400
Asn Thr Gly Thr Ala Pro Ile Tyr Asn Val Leu Pro Thr Thr Ser Leu
             405             410             415
Val Leu Gly Lys Asn Gln Thr Leu Ala Thr Ile Lys Ala Lys Glu Asn
             420             425             430
Gln Leu Ser Gln Ile Leu Ala Pro Asn Asn Tyr Tyr Pro Ser Lys Asn
         435             440             445
Leu Ala Pro Ile Ala Leu Asn Ala Gln Asp Asp Phe Ser Ser Thr Pro
 450             455             460
```

```
Ile Thr Met Asn Tyr Asn Gln Phe Leu Glu Leu Glu Lys Thr Lys Gln
465                 470                 475                 480

Leu Arg Leu Asp Thr Asp Gln Val Tyr Gly Asn Ile Ala Thr Tyr Asn
            485                 490                 495

Phe Glu Asn Gly Arg Val Arg Val Asp Thr Gly Ser Asn Trp Ser Glu
        500                 505                 510

Val Leu Pro Gln Ile Gln Glu Thr Thr Ala Arg Ile Ile Phe Asn Gly
    515                 520                 525

Lys Asp Leu Asn Leu Val Glu Arg Arg Ile Ala Ala Val Asn Pro Ser
530                 535                 540

Asp Pro Leu Glu Thr Thr Lys Pro Asp Met Thr Leu Lys Glu Ala Leu
545                 550                 555                 560

Lys Ile Ala Phe Gly Phe Asn Glu Pro Asn Gly Asn Leu Gln Tyr Gln
            565                 570                 575

Gly Lys Asp Ile Thr Glu Phe Asp Phe Asn Phe Asp Gln Gln Thr Ser
        580                 585                 590

Gln Asn Ile Lys Asn Gln Leu Ala Glu Leu Asn Ala Thr Asn Ile Tyr
    595                 600                 605

Thr Val Leu Asp Lys Ile Lys Leu Asn Ala Lys Met Asn Ile Leu Ile
610                 615                 620

Arg Asp Lys Arg Phe His Tyr Asp Arg Asn Asn Ile Ala Val Gly Ala
625                 630                 635                 640

Asp Glu Ser Val Val Lys Glu Ala His Arg Glu Val Ile Asn Ser Ser
            645                 650                 655

Thr Glu Gly Leu Leu Leu Asn Ile Asp Lys Asp Ile Arg Lys Ile Leu
        660                 665                 670

Ser Gly Tyr Ile Val Glu Ile Glu Asp Thr Glu Gly Leu Lys Glu Val
    675                 680                 685

Ile Asn Asp Arg Tyr Asp Met Leu Asn Ile Ser Ser Leu Arg Gln Asp
690                 695                 700

Gly Lys Thr Phe Ile Asp Phe Lys Lys Tyr Asn Asp Lys Leu Pro Leu
705                 710                 715                 720

Tyr Ile Ser Asn Pro Asn Tyr Lys Val Asn Val Tyr Ala Val Thr Lys
            725                 730                 735

Glu Asn Thr Ile Ile Asn Pro Ser Glu Asn Gly Asp Thr Ser Thr Asn
        740                 745                 750

Gly Ile Lys Lys Ile Leu Ile Phe Ser Lys Lys Gly Tyr Glu Ile Gly
    755                 760                 765

<210> SEQ ID NO 9
<211> LENGTH: 2304
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-U2-K197A (PA-U-K197A)

<400> SEQUENCE: 9
atgaaaaaac gaaaagtgtt aataccatta atggcattgt ctacgatatt agtttcaagc    60
acaggtaatt tagaggtgat tcaggcagaa gttaaacagg agaaccggtt attaaatgaa   120
tcagaatcaa gttcccaggg gttactagga tactatttta gtgatttgaa ttttcaagca   180
cccatggtgg ttacctcttc tactacaggg gatttatcta ttcctagttc tgagttagaa   240
aatattccat cggaaaacca atatttcaa tctgctattg gtcaggatt tatcaaagtt   300 aagaagagtg atgaatatac atttgctact tccgctgata atcatgtaac aatgtgggta   360
```

```
gatgaccaag aagtgattaa taaagcttct aattctaaca aaatcagatt agaaaaagga    420
agattatatc aaataaaaat tcaatatcaa cgagaaaatc ctactgaaaa aggattggat    480
ttcaagttgt actggaccga ttctcaaaat aaaaagaag tgatttctag tgataactta     540
caattgccag aattaaaaca aaaatcttcg aactcaccag gaagtggaag atcagcaagt    600
acaagtgctg gacctacggt tccagaccgt gacaatgatg aatccctga ttcattagag     660 gtagaaggat atacggttga tgtcgcaaat aaaagaactt ttctttcacc atggatttct    720
aatattcatg aaagaaagg attaaccaaa tataaatcat ctcctgaaaa atggagcacg     780
gcttctgatc cgtacagtga tttcgaaaag gttacaggac ggattgataa gaatgtatca    840
ccagaggcaa gacacccct tgtggcagct tatccgattg tacatgtaga tatggagaat     900
attattctct caaaaaatga ggatcaatcc acacagaata ctgatagtca aacgagaaca    960
ataagtaaaa atacttctac aagtaggaca catactagtg aagtacatgg aaatgcagaa    1020
gtgcatgcgt cgttctttga tattggtggg agtgtatctg caggatttag taattcgaat    1080
tcaagtacgg tcgcaattga tcattcacta tctctagcag gggaaagaac ttgggctgaa    1140
acaatgggtt taaataccgc tgatacagca agattaaatg ccaatattag atatgtaaat    1200
actgggacgg ctccaatcta caacgtgtta ccaacgactt cgttagtgtt aggaaaaaat    1260
caaacactcg cgacaattaa agctaaggaa accaattaa gtcaaatact tgcacctaat     1320
aattattatc cttctaaaaa cttggcgcca atcgcattaa atgcacaaga cgatttcagt    1380
tctactccaa ttacaatgaa ttacaatcaa tttcttgagt tagaaaaaac gaaacaatta    1440
agattagata cggatcaagt atatgggaat atagcaacat acaatttga aaatggaaga     1500 gtgagggtgg atacaggctc gaactggagt gaagtgttac cgcaaattca agaaacaact    1560
gcacgtatca ttttaatgg aaaagattta atctggtag aaaggcggat agcggcggtt      1620
aatcctagtg atccattaga aacgactaaa ccggatatga cattaaaaga agcccttaaa    1680
atagcatttg gatttaacga accgaatgga aacttacaat atcaagggaa agacataacc    1740
gaatttgatt ttaatttcga tcaacaaaca tctcaaaata tcaagaatca gttagcggaa    1800
ttaaacgcaa ctaacatata tactgtatta gataaaatca aattaaatgc aaaaatgaat    1860
attttaataa gagataaacg ttttcattat gatagaaata acatagcagt tgggcggat     1920 gagtcagtag ttaaggaggc tcatagagaa gtaattaatt cgtcaacaga gggattattg    1980
ttaaatattg ataaggatat aagaaaaata ttatcaggtt atattgtaga aattgaagat    2040
actgaagggc ttaaagaagt tataaatgac agatatgata tgttgaatat ttctagttta    2100
cggcaagatg gaaaaacatt tatagatttt aaaaaatata atgataaatt accgttatat    2160
ataagtaatc ccaattataa ggtaaatgta tatgctgtta ctaaagaaaa cactattatt    2220
aatcctagtg agaatgggga tactagtacc aacgggatca gaaaattttt aatctttct     2280 aaaaaaggct atgagatagg ataa                                           2304
```

<210> SEQ ID NO 10
<211> LENGTH: 767
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-U2-K197A (PA-U-K197A)
<220> FEATURE:
<221> NAME/KEY: SIGNAL
<222> LOCATION: (1)..(29)
<223> OTHER INFORMATION: signal peptide

<400> SEQUENCE: 10

Met Lys Lys Arg Lys Val Leu Ile Pro Leu Met Ala Leu Ser Thr Ile
1               5                   10                  15

Leu Val Ser Ser Thr Gly Asn Leu Glu Val Ile Gln Ala Glu Val Lys
            20                  25                  30

Gln Glu Asn Arg Leu Leu Asn Glu Ser Glu Ser Ser Gln Gly Leu
        35                  40                  45

Leu Gly Tyr Tyr Phe Ser Asp Leu Asn Phe Gln Ala Pro Met Val Val
    50                  55                  60

Thr Ser Ser Thr Thr Gly Asp Leu Ser Ile Pro Ser Ser Glu Leu Glu
65                  70                  75                  80

Asn Ile Pro Ser Glu Asn Gln Tyr Phe Gln Ser Ala Ile Trp Ser Gly
                85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Pro Gly Ser Gly Arg Ser Ala Ser Thr Ser Ala Gly Pro Thr Val Pro
        195                 200                 205

Asp Arg Asp Asn Asp Gly Ile Pro Asp Ser Leu Glu Val Glu Gly Tyr
    210                 215                 220

Thr Val Asp Val Ala Asn Lys Arg Thr Phe Leu Ser Pro Trp Ile Ser
225                 230                 235                 240

Asn Ile His Glu Lys Lys Gly Leu Thr Lys Tyr Lys Ser Ser Pro Glu
                245                 250                 255

Lys Trp Ser Thr Ala Ser Asp Pro Tyr Ser Asp Phe Glu Lys Val Thr
            260                 265                 270

Gly Arg Ile Asp Lys Asn Val Ser Pro Glu Ala Arg His Pro Leu Val
        275                 280                 285

Ala Ala Tyr Pro Ile Val His Val Asp Met Glu Asn Ile Ile Leu Ser
    290                 295                 300

Lys Asn Glu Asp Gln Ser Thr Gln Asn Thr Asp Ser Gln Thr Arg Thr
305                 310                 315                 320

Ile Ser Lys Asn Thr Ser Thr Ser Arg Thr His Thr Ser Glu Val His
                325                 330                 335

Gly Asn Ala Glu Val His Ala Ser Phe Phe Asp Ile Gly Gly Ser Val
            340                 345                 350

Ser Ala Gly Phe Ser Asn Ser Asn Ser Ser Thr Val Ala Ile Asp His
        355                 360                 365

Ser Leu Ser Leu Ala Gly Glu Arg Thr Trp Ala Glu Thr Met Gly Leu
    370                 375                 380

Asn Thr Ala Asp Thr Ala Arg Leu Asn Ala Asn Ile Arg Tyr Val Asn
385                 390                 395                 400

Thr Gly Thr Ala Pro Ile Tyr Asn Val Leu Pro Thr Thr Ser Leu Val
                405                 410                 415

Leu Gly Lys Asn Gln Thr Leu Ala Thr Ile Lys Ala Lys Glu Asn Gln
                420                 425                 430

Leu Ser Gln Ile Leu Ala Pro Asn Asn Tyr Tyr Pro Ser Lys Asn Leu
            435                 440                 445

Ala Pro Ile Ala Leu Asn Ala Gln Asp Asp Phe Ser Ser Thr Pro Ile
450                 455                 460

Thr Met Asn Tyr Asn Gln Phe Leu Glu Leu Glu Lys Thr Lys Gln Leu
465                 470                 475                 480

Arg Leu Asp Thr Asp Gln Val Tyr Gly Asn Ile Ala Thr Tyr Asn Phe
                485                 490                 495

Glu Asn Gly Arg Val Arg Val Asp Thr Gly Ser Asn Trp Ser Glu Val
            500                 505                 510

Leu Pro Gln Ile Gln Glu Thr Thr Ala Arg Ile Ile Phe Asn Gly Lys
        515                 520                 525

Asp Leu Asn Leu Val Glu Arg Arg Ile Ala Ala Val Asn Pro Ser Asp
530                 535                 540

Pro Leu Glu Thr Thr Lys Pro Asp Met Thr Leu Lys Glu Ala Leu Lys
545                 550                 555                 560

Ile Ala Phe Gly Phe Asn Glu Pro Asn Gly Asn Leu Gln Tyr Gln Gly
                565                 570                 575

Lys Asp Ile Thr Glu Phe Asp Phe Asn Phe Asp Gln Gln Thr Ser Gln
            580                 585                 590

Asn Ile Lys Asn Gln Leu Ala Glu Leu Asn Ala Thr Asn Ile Tyr Thr
        595                 600                 605

Val Leu Asp Lys Ile Lys Leu Asn Ala Lys Met Asn Ile Leu Ile Arg
610                 615                 620

Asp Lys Arg Phe His Tyr Asp Arg Asn Asn Ile Ala Val Gly Ala Asp
625                 630                 635                 640

Glu Ser Val Val Lys Glu Ala His Arg Glu Val Ile Asn Ser Ser Thr
                645                 650                 655

Glu Gly Leu Leu Leu Asn Ile Asp Lys Asp Ile Arg Lys Ile Leu Ser
            660                 665                 670

Gly Tyr Ile Val Glu Ile Glu Asp Thr Glu Gly Leu Lys Glu Val Ile
        675                 680                 685

Asn Asp Arg Tyr Asp Met Leu Asn Ile Ser Ser Leu Arg Gln Asp Gly
690                 695                 700

Lys Thr Phe Ile Asp Phe Lys Lys Tyr Asn Asp Lys Leu Pro Leu Tyr
705                 710                 715                 720

Ile Ser Asn Pro Asn Tyr Lys Val Asn Val Tyr Ala Val Thr Lys Glu
                725                 730                 735

Asn Thr Ile Ile Asn Pro Ser Glu Asn Gly Asp Thr Ser Thr Asn Gly
            740                 745                 750

Ile Lys Lys Ile Leu Ile Phe Ser Lys Lys Gly Tyr Glu Ile Gly
        755                 760                 765

<210> SEQ ID NO 11
<211> LENGTH: 2295
<212> TYPE: DNA
<213> ORGANISM: Bacillus anthracis
<220> FEATURE:
<223> OTHER INFORMATION: wild-type homo-oligomeric anthrax toxin
      protective antigen (PrAg)

<400> SEQUENCE: 11
atgaaaaaac gaaaagtgtt aataccatta atggcattgt ctacgatatt agtttcaagc    60

```
acaggtaatt tagaggtgat tcaggcagaa gttaaacagg agaaccggtt attaaatgaa      120
tcagaatcaa gttcccaggg gttactagga tactatttta gtgatttgaa ttttcaagca      180
cccatggtgg ttacctcttc tactacaggg gatttatcta ttcctagttc tgagttagaa      240
aatattccat cggaaaacca atattttcaa tctgctattt ggtcaggatt tatcaaagtt      300
aagaagagtg atgaatatac atttgctact ccgctgata atcatgtaac aatgtgggta       360
gatgaccaag aagtgattaa taaagcttct aattctaaca aaatcagatt agaaaaagga      420
agattatatc aaataaaaat tcaatatcaa cgagaaaatc ctactgaaaa aggattggat      480
ttcaagttgt actggaccga ttctcaaaat aaaaagaag tgatttctag tgataactta        540
caattgccag aattaaaaca aaaatcttcg aactcaagaa aaaagcgaag tacaagtgct      600
ggacctacgg ttccagaccg tgacaatgat ggaatccctg attcattaga ggtagaagga      660
tatacggttg atgtcaaaaa taaaagaact tttcttttcac catggatttc taatattcat     720
gaaaagaaag gattaaccaa atataaatca tctcctgaaa aatggagcac ggcttctgat      780
ccgtacagtg atttcgaaaa ggttacagga cggattgata agaatgtatc accagaggca      840
agacaccccc ttgtggcagc ttatccgatt gtacatgtag atatggagaa tattattctc      900
tcaaaaaatg aggatcaatc cacacagaat actgatagtc aaacgagaac aataagtaaa      960
aatacttcta caagtaggac acatactagt gaagtacatg gaaatgcaga agtgcatgcg      1020
tcgttctttg atattggtgg gagtgtatct gcaggattta gtaattcgaa ttcaagtacg      1080
gtcgcaattg atcattcact atctctagca ggggaaagaa cttgggctga acaatgggt      1140 ttaaataccg ctgatacagc aagattaaat gccaatatta gatatgtaaa tactgggacg      1200
gctccaatct acaacgtgtt accaacgact tcgttagtgt taggaaaaaa tcaaacactc      1260
gcgacaatta aagctaagga aaaccaatta agtcaaatac ttgcacctaa taattattat      1320
ccttctaaaa acttggcgcc aatcgcatta aatgcacaag acgatttcag ttctactcca      1380
attacaatga attacaatca atttcttgag ttagaaaaaa cgaaacaatt aagattagat      1440
acggatcaag tatatgggaa tatagcaaca tacaattttg aaaatggaag agtgagggtg      1500
gatacaggct cgaactggag tgaagtgtta ccgcaaaattc agaaacaac tgcacgtatc      1560 attttttaatg gaaaagattt aaatctggta gaaaggcgga tagcggcggt taatcctagt      1620
gatccattag aaaacgactaa accggatatg acattaaaag aagcccttaa aatagcattt      1680 ggattaacg aaccgaatgg aaacttacaa tatcaaggga agacataac cgaatttgat       1740 tttaattttcg atcaacaaac atctcaaaat atcaagaatc agttagcgga attaaacgca     1800
actaacatat atactgtatt agataaaatc aaattaaatg caaaaatgaa tattttaata      1860
agagataaac gttttcatta tgatagaaat aacatagcag ttggggcgga tgagtcagta      1920
gttaaggagg ctcatagaga agtaattaat tcgtcaacag agggattatt gttaaatatt     1980
gataaggata taagaaaaat attatcaggt tatattgtag aaattgaaga tactgaaggg      2040
cttaaagaag ttataaatga cagatatgat atgttgaata tttctagttt acggcaagat     2100
ggaaaaacat ttatagattt taaaaatat aatgataaat taccgttata tataagtaat      2160
cccaattata aggtaaatgt atatgctgtt actaaagaaa acactattat taatcctagt    2220
gagaatgggg atactagtac caacgggatc aagaaaattt taatctttt taaaaaaggc      2280 tatgagatag gataa                                                        2295
```

<210> SEQ ID NO 12
<211> LENGTH: 764
<212> TYPE: PRT

-continued

```
<213> ORGANISM: Bacillus anthracis
<220> FEATURE:
<223> OTHER INFORMATION: wild-type homo-oligomeric anthrax toxin
      protective antigen (PrAg), anthrax toxin protective antigen
      (PrAg, pagA, pXO1-110) component
<220> FEATURE:
<221> NAME/KEY: SIGNAL
<222> LOCATION: (1)..(29)
<223> OTHER INFORMATION: signal peptide

<400> SEQUENCE: 12

Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365
```

Leu Ala Gly Glu Arg Thr Trp Ala Glu Thr Met Gly Leu Asn Thr Ala
     370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 13
<211> LENGTH: 2304
<212> TYPE: DNA

<213> ORGANISM: Artificial Sequence
<220> FEATURE:
<223> OTHER INFORMATION: Description of Artificial Sequence:modified
homo-oligomeric anthrax toxin protective antigen
(PrAg) PrAg-U2

<400> SEQUENCE: 13

```
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa ttttcaagca     180
cccatggtgg ttacctcttc tactacaggg gatttatcta ttcctagttc tgagttagaa     240
aatattccat cggaaaacca atattttcaa tctgctattt ggtcaggatt tatcaaagtt     300
aagaagagtg atgaatatac atttgctact tccgctgata tcatgtaac aatgtgggta      360
gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaagaag tgatttctag tgataactta     540
caattgccag aattaaaaca aaatcttcg aactcaccag gaagtggaag atcagcaagt     600
acaagtgctg gacctacggt tccagaccgt gacaatgatg gaatccctga ttcattagag     660
gtagaaggat atacggttga tgtcaaaaat aaaagaactt ttctttcacc atggatttct     720
aatattcatg aaaagaaagg attaaccaaa tataaatcat ctcctgaaaa atggagcacg     780
gcttctgatc cgtacagtga tttcgaaaag gttacaggac ggattgataa gaatgtatca     840
ccagaggcaa gacacccct tgtggcagct tatccgattg tacatgtaga tatggagaat     900
attattctct caaaaaatga ggatcaatcc acacagaata ctgatagtca acgagaaca    960
ataagtaaaa atacttctac aagtaggaca catactagtg aagtacatgg aaatgcagaa    1020
gtgcatgcgt cgttctttga tattggtggg agtgtatctg caggatttag taattcgaat    1080
tcaagtacgg tcgcaattga tcattcacta tctctagcag gggaaagaac ttgggctgaa    1140
acaatggggtt taaataccgc tgatacagca agattaaatg ccaatattag atatgtaaat    1200
actgggacgg ctccaatcta caacgtgtta ccaacgactt cgttagtgtt aggaaaaaat    1260
caaacactcg cgacaattaa agctaaggaa aaccaattaa gtcaaatact tgcacctaat    1320
aattattatc cttctaaaaa cttggcgcca atcgcattaa atgcacaaga cgatttcagt    1380
tctactccaa ttacaatgaa ttacaatcaa tttcttgagt tagaaaaaac gaaacaatta    1440
agattagata cggatcaagt atatgggaat atagcaacat acaattttga aaatggaaga    1500
gtgagggtgg atacaggctc gaactggagt gaagtgttac cgcaaattca agaaacaact    1560
gcacgtatca tttttaatgg aaaagattta aatctggtag aaaggcggat agcggcggtt    1620
aatcctagtg atccattaga aacgactaaa ccggatatga cattaaaaga agcccttaaa    1680
atagcatttg gatttaacga accgaatgga aacttacaat atcaagggaa agacataacc    1740
gaatttgatt ttaatttcga tcaacaaaca tctcaaaata tcaagaatca gttagcggaa    1800
ttaaacgcaa ctaacatata tactgtatta gataaaatca attaaatgc aaaaatgaat    1860
attttaataa gagataaacg ttttcattat gatagaaata acatagcagt tggggcggat    1920
gagtcagtag ttaaggaggc tcatagaaa gtaattaatt cgtcaacaga gggattattg    1980
ttaaatattg ataaggatat aagaaaaata ttatcaggtt atattgtaga aattgaagat    2040
actgaagggc ttaagaagt tataaatgac agatatgata tgttgaatat ttctagttta    2100
cggcaagatg gaaaaacatt tatagatttt aaaaatata atgataaatt accgttatat    2160
```

-continued

```
ataagtaatc ccaattataa ggtaaatgta tatgctgtta ctaaagaaaa cactattatt    2220
aatcctagtg agaatgggga tactagtacc aacgggatca agaaaatttt aatctttttct   2280 aaaaaaggct atgagatagg ataa                                          2304
```

<210> SEQ ID NO 14
<211> LENGTH: 767
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-U2
<220> FEATURE:
<221> NAME/KEY: SIGNAL
<222> LOCATION: (1)..(29)
<223> OTHER INFORMATION: signal peptide

<400> SEQUENCE: 14

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Pro Gly Ser Gly Arg Ser Ala Ser Thr Ser Ala Gly Pro Thr Val Pro
        195                 200                 205

Asp Arg Asp Asn Asp Gly Ile Pro Asp Ser Leu Glu Val Glu Gly Tyr
    210                 215                 220

Thr Val Asp Val Lys Asn Lys Arg Thr Phe Leu Ser Pro Trp Ile Ser
225                 230                 235                 240

Asn Ile His Glu Lys Lys Gly Leu Thr Lys Tyr Lys Ser Ser Pro Glu
                245                 250                 255

Lys Trp Ser Thr Ala Ser Asp Pro Tyr Ser Asp Phe Glu Lys Val Thr
            260                 265                 270

Gly Arg Ile Asp Lys Asn Val Ser Pro Glu Ala Arg His Pro Leu Val
        275                 280                 285

Ala Ala Tyr Pro Ile Val His Val Asp Met Glu Asn Ile Ile Leu Ser
    290                 295                 300

Lys Asn Glu Asp Gln Ser Thr Gln Asn Thr Asp Ser Gln Thr Arg Thr
```

```
                305                 310                 315                 320
Ile Ser Lys Asn Thr Ser Thr Ser Arg Thr His Thr Ser Glu Val His
                325                 330                 335
Gly Asn Ala Glu Val His Ala Ser Phe Phe Asp Ile Gly Gly Ser Val
                340                 345                 350
Ser Ala Gly Phe Ser Asn Ser Asn Ser Ser Thr Val Ala Ile Asp His
                355                 360                 365
Ser Leu Ser Leu Ala Gly Glu Arg Thr Trp Ala Glu Thr Met Gly Leu
                370                 375                 380
Asn Thr Ala Asp Thr Ala Arg Leu Asn Ala Asn Ile Arg Tyr Val Asn
385                 390                 395                 400
Thr Gly Thr Ala Pro Ile Tyr Asn Val Leu Pro Thr Thr Ser Leu Val
                405                 410                 415
Leu Gly Lys Asn Gln Thr Leu Ala Thr Ile Lys Ala Lys Glu Asn Gln
                420                 425                 430
Leu Ser Gln Ile Leu Ala Pro Asn Asn Tyr Tyr Pro Ser Lys Asn Leu
                435                 440                 445
Ala Pro Ile Ala Leu Asn Ala Gln Asp Asp Phe Ser Ser Thr Pro Ile
                450                 455                 460
Thr Met Asn Tyr Asn Gln Phe Leu Glu Leu Glu Lys Thr Lys Gln Leu
465                 470                 475                 480
Arg Leu Asp Thr Asp Gln Val Tyr Gly Asn Ile Ala Thr Tyr Asn Phe
                485                 490                 495
Glu Asn Gly Arg Val Arg Val Asp Thr Gly Ser Asn Trp Ser Glu Val
                500                 505                 510
Leu Pro Gln Ile Gln Glu Thr Thr Ala Arg Ile Ile Phe Asn Gly Lys
                515                 520                 525
Asp Leu Asn Leu Val Glu Arg Arg Ile Ala Ala Val Asn Pro Ser Asp
                530                 535                 540
Pro Leu Glu Thr Thr Lys Pro Asp Met Thr Leu Lys Glu Ala Leu Lys
545                 550                 555                 560
Ile Ala Phe Gly Phe Asn Glu Pro Asn Gly Asn Leu Gln Tyr Gln Gly
                565                 570                 575
Lys Asp Ile Thr Glu Phe Asp Phe Asn Phe Asp Gln Gln Thr Ser Gln
                580                 585                 590
Asn Ile Lys Asn Gln Leu Ala Glu Leu Asn Ala Thr Asn Ile Tyr Thr
                595                 600                 605
Val Leu Asp Lys Ile Lys Leu Asn Ala Lys Met Asn Ile Leu Ile Arg
                610                 615                 620
Asp Lys Arg Phe His Tyr Asp Arg Asn Asn Ile Ala Val Gly Ala Asp
625                 630                 635                 640
Glu Ser Val Val Lys Glu Ala His Arg Glu Val Ile Asn Ser Ser Thr
                645                 650                 655
Glu Gly Leu Leu Leu Asn Ile Asp Lys Asp Ile Arg Lys Ile Leu Ser
                660                 665                 670
Gly Tyr Ile Val Glu Ile Glu Asp Thr Glu Gly Leu Lys Glu Val Ile
                675                 680                 685
Asn Asp Arg Tyr Asp Met Leu Asn Ile Ser Ser Leu Arg Gln Asp Gly
                690                 695                 700
Lys Thr Phe Ile Asp Phe Lys Lys Tyr Asn Asp Lys Leu Pro Leu Tyr
705                 710                 715                 720
Ile Ser Asn Pro Asn Tyr Lys Val Asn Val Tyr Ala Val Thr Lys Glu
                725                 730                 735
```

Asn Thr Ile Ile Asn Pro Ser Glu Asn Gly Asp Thr Ser Thr Asn Gly
            740                 745                 750

Ile Lys Lys Ile Leu Ile Phe Ser Lys Lys Gly Tyr Glu Ile Gly
        755                 760                 765

<210> SEQ ID NO 15
<211> LENGTH: 2295
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-R200A

<400> SEQUENCE: 15

| | | | | | |
|---|---|---|---|---|---|
| atgaaaaaac | gaaaagtgtt | aataccatta | atggcattgt | ctacgatatt | agtttcaagc | 60 |
| acaggtaatt | tagaggtgat | tcaggcagaa | gttaaacagg | agaaccggtt | attaaatgaa | 120 |
| tcagaatcaa | gttcccaggg | gttactagga | tactatttta | gtgatttgaa | ttttcaagca | 180 |
| cccatggtgg | ttacctcttc | tactacaggg | gatttatcta | ttcctagttc | tgagttagaa | 240 |
| aatattccat | cggaaaacca | atattttcaa | tctgctattt | ggtcaggatt | tatcaaagtt | 300 |
| aagaagagtg | atgaatatac | atttgctact | tccgctgata | atcatgtaac | aatgtgggta | 360 |
| gatgaccaag | aagtgattaa | taaagcttct | aattctaaca | aaatcagatt | agaaaaagga | 420 |
| agattatatc | aaataaaaat | tcaatatcaa | cgagaaaatc | ctactgaaaa | aggattggat | 480 |
| ttcaagttgt | actggaccga | ttctcaaaat | aaaaagaag | tgatttctag | tgataactta | 540 |
| caattgccag | aattaaaaca | aaaatcttcg | aactcaagaa | aaaagcgaag | tacaagtgct | 600 |
| ggacctacgg | ttccagaccg | tgacaatgat | ggaatccctg | attcattaga | ggtagaagga | 660 |
| tatacggttg | atgtcaaaaa | taaagcaact | tttctttcac | catggattc | taatattcat | 720 |
| gaaaagaaag | gattaaccaa | atataaatca | tctcctgaaa | aatggagcac | ggcttctgat | 780 |
| ccgtacagtg | atttcgaaaa | ggttacagga | cggattgata | agaatgtatc | accagaggca | 840 |
| agacacccc | ttgtggcagc | ttatccgatt | gtacatgtag | atatggagaa | tattattctc | 900 |
| tcaaaaaatg | aggatcaatc | cacacagaat | actgatagtc | aaacgagaac | aataagtaaa | 960 |
| aatacttcta | caagtaggac | acatactagt | gaagtacatg | gaaatgcaga | agtgcatgcg | 1020 |
| tcgttctttg | atattggtgg | gagtgtatct | gcaggattta | gtaattcgaa | ttcaagtacg | 1080 |
| gtcgcaattg | atcattcact | atctctagca | ggggaaagaa | cttgggctga | acaatgggt | 1140 |
| ttaaataccg | ctgatacagc | aagattaaat | gccaatatta | gatatgtaaa | tactgggacg | 1200 |
| gctccaatct | acaacgtgtt | accaacgact | tcgttagtgt | taggaaaaaa | tcaaacactc | 1260 |
| gcgacaatta | agctaagga | aaaccaatta | agtcaaatac | ttgcacctaa | taattattat | 1320 |
| ccttctaaaa | acttggcgcc | aatcgcatta | aatgcacaag | acgatttcag | ttctactcca | 1380 |
| attacaatga | attacaatca | atttcttgag | ttagaaaaaa | cgaaacaatt | aagattagat | 1440 |
| acggatcaag | tatatgggaa | tatagcaaca | tacaattttg | aaaatggaag | agtgagggtg | 1500 |
| gatacaggct | cgaactggag | tgaagtgtta | ccgcaaattc | aagaaacaac | tgcacgtatc | 1560 |
| attttaatg | aaaagatt | aaatctggta | gaaggcgga | tagcggcggt | taatcctagt | 1620 |
| gatccattag | aaacgactaa | accggatatg | acattaaaag | aagcccttaa | aatagcattt | 1680 |
| ggatttaacg | aaccgaatgg | aaacttacaa | tatcaaggga | aagacataac | cgaatttgat | 1740 |
| tttaatttcg | atcaacaaac | atctcaaaat | atcaagaatc | agttagcgga | attaaacgca | 1800 |
| actaacatat | atactgtatt | agataaaatc | aaattaaatg | caaaaatgaa | tattttaata | 1860 |

-continued

```
agagataaac gttttcatta tgatagaaat aacatagcag ttggggcgga tgagtcagta    1920
gttaaggagg ctcatagaga agtaattaat tcgtcaacag agggattatt gttaaatatt    1980
gataaggata taagaaaaat attatcaggt tatattgtag aaattgaaga tactgaaggg    2040
cttaaagaag ttataaatga cagatatgat atgttgaata tttctagttt acggcaagat    2100
ggaaaaacat ttatagattt taaaaaatat aatgataaat taccgttata tataagtaat    2160
cccaattata aggtaaatgt atatgctgtt actaaagaaa acactattat taatcctagt    2220
gagaatgggg atactagtac caacgggatc aagaaaattt taatcttttc taaaaaaggc    2280
tatgagatag gataa                                                     2295

<210> SEQ ID NO 16
<211> LENGTH: 764
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-R200A
<220> FEATURE:
<221> NAME/KEY: SIGNAL
<222> LOCATION: (1)..(29)
<223> OTHER INFORMATION: signal peptide

<400> SEQUENCE: 16

Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Ala Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255
```

-continued

```
Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285

Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685
```

```
Tyr Asp Met Leu Asn Ile Ser Ser Leu Arg Gln Asp Gly Lys Thr Phe
    690                 695                 700
Ile Asp Phe Lys Lys Tyr Asn Asp Lys Leu Pro Leu Tyr Ile Ser Asn
705                 710                 715                 720
Pro Asn Tyr Lys Val Asn Val Tyr Ala Val Thr Lys Glu Asn Thr Ile
                725                 730                 735
Ile Asn Pro Ser Glu Asn Gly Asp Thr Ser Thr Asn Gly Ile Lys Lys
            740                 745                 750
Ile Leu Ile Phe Ser Lys Lys Gly Tyr Glu Ile Gly
        755                 760
```

<210> SEQ ID NO 17
<211> LENGTH: 2307
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-L1

<400> SEQUENCE: 17

```
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga tactatttta gtgatttgaa ttttcaagca     180
cccatggtgg ttacctcttc tactacaggg gattttatcta ttcctagttc tgagttagaa     240
aatattccat cggaaaacca atattttcaa tctgctattt ggtcaggatt tatcaaagtt     300
aagaagagtg atgaatatac atttgctact tccgctgata tcatgtaac aatgtgggta     360 gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaaagaag tgatttctag tgataactta     540
caattgccag aattaaaaca aaatctttcg aactcaggac cattaggaat gttgagtcaa     600
agtacaagtg ctggacctac ggttccagac cgtgacaatg atggaatccc tgattcatta     660
gaggtagaag atatacggt tgatgtcaaa aataaaagaa cttttctttc accatggatt     720
tctaatattc atgaaaagaa aggattaacc aaatataaat catctcctga aaaatggagc     780
acggcttctg atccgtacag tgatttcgaa aaggttacag gacggattga taagaatgta     840
tcaccagagg caagacaccc ccttgtggca gcttatccga ttgtacatgt agatatggag     900
aatattattc tctcaaaaaa tgaggatcaa tccacacaga atactgatag tcaaacgaga     960
acaataagta aaaatacttc tacaagtagg acacatacta gtgaagtaca tggaaatgca    1020
gaagtgcatg cgtcgttctt tgatattggt gggagtgtat ctgcaggatt tagtaattcg    1080
aattcaagta cggtcgcaat tgatcattca ctatctctag caggggaaag aacttgggct    1140
gaaacaatgg gtttaaatac cgctgataca gcaagattaa atgccaatat tagatatgta    1200
aatactggga cggctccaat ctacaacgtg ttaccaacga cttcgttagt gttaggaaaa    1260
aatcaaacac tcgcgacaat taaagctaag gaaaaccaat taagtcaaat acttgcacct    1320
aataattatt atcctctaa aaacttggcg ccaatcgcat taatgcaca agacgatttc    1380 agttctactc caattacaat gaattacaat caatttcttg agttagaaaa aacgaaacaa    1440
ttaagattag atacggatca agtatatggg aatatagcaa catacaattt tgaaaatgga    1500
agagtgaggg tggatacagg ctcgaactgg agtgaagtgt taccgcaaat tcaagaaaca    1560
```

```
actgcacgta tcatttttaa tggaaaagat ttaaatctgg tagaaaggcg gatagcggcg    1620
gttaatccta gtgatccatt agaaacgact aaaccggata tgacattaaa agaagccctt    1680
aaaatagcat ttggatttaa cgaaccgaat ggaaacttac aatatcaagg gaaagacata    1740
accgaatttg attttaattt cgatcaacaa acatctcaaa atatcaagaa tcagttagcg    1800
gaattaaacg caactaacat atatactgta ttagataaaa tcaaattaaa tgcaaaaatg    1860
aatatttaaa taagagataa acgttttcat tatgatagaa ataacatagc agttggggcg    1920
gatgagtcag tagttaagga ggctcataga gaagtaatta attcgtcaac agagggatta    1980
ttgttaaata ttgataagga tataagaaaa atattatcag gttatattgt agaaattgaa    2040
gatactgaag ggcttaaaga agttataaat gacagatatg atatgttgaa tatttctagt    2100
ttacggcaag atggaaaaac atttatagat tttaaaaaat ataatgataa attaccgtta    2160
tatataagta atcccaatta taaggtaaat gtatatgctg ttactaaaga aaacactatt    2220
attaatccta gtgagaatgg ggatactagt accaacggga tcaagaaaat tttaatcttt    2280
tctaaaaaag gctatgagat aggataa                                        2307
```

<210> SEQ ID NO 18  
<211> LENGTH: 768  
<212> TYPE: PRT  
<213> ORGANISM: Artificial Sequence  
<220> FEATURE:  
<223> OTHER INFORMATION: Description of Artificial Sequence:modified homo-oligomeric anthrax toxin protective antigen (PrAg) PrAg-L1  
<220> FEATURE:  
<221> NAME/KEY: SIGNAL  
<222> LOCATION: (1)..(29)  
<223> OTHER INFORMATION: signal peptide

<400> SEQUENCE: 18

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Gly Pro Leu Gly Met Leu Ser Gln Ser Thr Ser Ala Gly Pro Thr Val
        195                 200                 205
```

```
Pro Asp Arg Asp Asn Asp Gly Ile Pro Asp Ser Leu Glu Val Glu Gly
    210                 215                 220
Tyr Thr Val Asp Val Lys Asn Lys Arg Thr Phe Leu Ser Pro Trp Ile
225                 230                 235                 240
Ser Asn Ile His Glu Lys Lys Gly Leu Thr Lys Tyr Lys Ser Ser Pro
                245                 250                 255
Glu Lys Trp Ser Thr Ala Ser Asp Pro Tyr Ser Asp Phe Glu Lys Val
            260                 265                 270
Thr Gly Arg Ile Asp Lys Asn Val Ser Pro Glu Ala Arg His Pro Leu
        275                 280                 285
Val Ala Ala Tyr Pro Ile Val His Val Asp Met Glu Asn Ile Ile Leu
    290                 295                 300
Ser Lys Asn Glu Asp Gln Ser Thr Gln Asn Thr Asp Ser Gln Thr Arg
305                 310                 315                 320
Thr Ile Ser Lys Asn Thr Ser Thr Ser Arg Thr His Thr Ser Glu Val
                325                 330                 335
His Gly Asn Ala Glu Val His Ala Ser Phe Phe Asp Ile Gly Gly Ser
            340                 345                 350
Val Ser Ala Gly Phe Ser Asn Ser Asn Ser Ser Thr Val Ala Ile Asp
        355                 360                 365
His Ser Leu Ser Leu Ala Gly Glu Arg Thr Trp Ala Glu Thr Met Gly
    370                 375                 380
Leu Asn Thr Ala Asp Thr Ala Arg Leu Asn Ala Asn Ile Arg Tyr Val
385                 390                 395                 400
Asn Thr Gly Thr Ala Pro Ile Tyr Asn Val Leu Pro Thr Thr Ser Leu
                405                 410                 415
Val Leu Gly Lys Asn Gln Thr Leu Ala Thr Ile Lys Ala Lys Glu Asn
            420                 425                 430
Gln Leu Ser Gln Ile Leu Ala Pro Asn Asn Tyr Tyr Pro Ser Lys Asn
        435                 440                 445
Leu Ala Pro Ile Ala Leu Asn Ala Gln Asp Asp Phe Ser Ser Thr Pro
    450                 455                 460
Ile Thr Met Asn Tyr Asn Gln Phe Leu Glu Leu Glu Lys Thr Lys Gln
465                 470                 475                 480
Leu Arg Leu Asp Thr Asp Gln Val Tyr Gly Asn Ile Ala Thr Tyr Asn
                485                 490                 495
Phe Glu Asn Gly Arg Val Arg Val Asp Thr Gly Ser Asn Trp Ser Glu
            500                 505                 510
Val Leu Pro Gln Ile Gln Glu Thr Thr Ala Arg Ile Ile Phe Asn Gly
        515                 520                 525
Lys Asp Leu Asn Leu Val Glu Arg Arg Ile Ala Ala Val Asn Pro Ser
    530                 535                 540
Asp Pro Leu Glu Thr Thr Lys Pro Asp Met Thr Leu Lys Glu Ala Leu
545                 550                 555                 560
Lys Ile Ala Phe Gly Phe Asn Glu Pro Asn Gly Asn Leu Gln Tyr Gln
                565                 570                 575
Gly Lys Asp Ile Thr Glu Phe Asp Phe Asn Phe Asp Gln Gln Thr Ser
            580                 585                 590
Gln Asn Ile Lys Asn Gln Leu Ala Glu Leu Asn Ala Thr Asn Ile Tyr
        595                 600                 605
Thr Val Leu Asp Lys Ile Lys Leu Asn Ala Lys Met Asn Ile Leu Ile
    610                 615                 620
Arg Asp Lys Arg Phe His Tyr Asp Arg Asn Asn Ile Ala Val Gly Ala
```

```
                 625                 630                 635                 640
Asp Glu Ser Val Val Lys Glu Ala His Arg Glu Val Ile Asn Ser Ser
                     645                 650                 655
Thr Glu Gly Leu Leu Leu Asn Ile Asp Lys Asp Ile Arg Lys Ile Leu
                660                 665                 670
Ser Gly Tyr Ile Val Glu Ile Glu Asp Thr Glu Gly Leu Lys Glu Val
            675                 680                 685
Ile Asn Asp Arg Tyr Asp Met Leu Asn Ile Ser Ser Leu Arg Gln Asp
        690                 695                 700
Gly Lys Thr Phe Ile Asp Phe Lys Lys Tyr Asn Asp Lys Leu Pro Leu
705                 710                 715                 720
Tyr Ile Ser Asn Pro Asn Tyr Lys Val Asn Val Tyr Ala Val Thr Lys
                725                 730                 735
Glu Asn Thr Ile Ile Asn Pro Ser Glu Asn Gly Asp Thr Ser Thr Asn
                740                 745                 750
Gly Ile Lys Lys Ile Leu Ile Phe Ser Lys Lys Gly Tyr Glu Ile Gly
            755                 760                 765

<210> SEQ ID NO 19
<211> LENGTH: 2295
<212> TYPE: DNA
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-I210A

<400> SEQUENCE: 19
atgaaaaaac gaaaagtgtt aataccatta atggcattgt ctacgatatt agtttcaagc      60
acaggtaatt tagaggtgat tcaggcagaa gttaaacagg agaaccggtt attaaatgaa     120
tcagaatcaa gttcccaggg gttactagga ctatttttta gtgatttgaa ttttcaagca     180
cccatggtgg ttacctcttc tactacaggg gatttatcta ttcctagttc tgagttagaa     240
aatattccat cggaaaacca atattttcaa tctgctattt ggtcaggatt tatcaaagtt     300
aagaagagtg atgaatatac atttgctact tccgctgata tcatgtaac aatgtgggta     360 gatgaccaag aagtgattaa taaagcttct aattctaaca aaatcagatt agaaaaagga     420
agattatatc aaataaaaat tcaatatcaa cgagaaaatc ctactgaaaa aggattggat     480
ttcaagttgt actggaccga ttctcaaaat aaaaaagaag tgatttctag tgataactta     540
caattgccag aattaaaaca aaaatcttcg aactcaagaa aaaagcgaag tacaagtgct     600
ggacctacgg ttccagaccg tgacaatgat ggaatccctg attcattaga ggtagaagga     660
tatacggttg atgtcaaaaa taaagaact tttctttcac catggatttc taatgcacat     720
gaaaagaaag gattaaccaa atataaatca tctcctgaaa aatggagcac ggcttctgat     780
ccgtacagtg atttcgaaaa ggttacagga cggattgata agaatgtatc accagaggca     840 agacacccc ttgtggcagc ttatccgatt gtacatgtag atatggagaa tattattctc     900
tcaaaaaatg aggatcaatc cacacagaat actgatagtc aaacgagaac aataagtaaa     960
aatacttcta caagtaggac acatactagt gaagtacatg aaatgcaga agtgcatgcg    1020 tcgttctttg atattggtgg gagtgtatct gcaggattta gtaattcgaa ttcaagtacg    1080
gtcgcaattg atcattcact atctctagca ggggaaagaa cttgggctga acaatgggt    1140 ttaaataccg ctgatacagc aagattaaat gccaatatta gatatgtaaa tactgggacg    1200
gctccaatct acaacgtgtt accaacgact tcgttagtgt taggaaaaaa tcaaacactc    1260
```

-continued

```
gcgacaatta aagctaagga aaaccaatta agtcaaatac ttgcacctaa taattattat    1320
ccttctaaaa acttggcgcc aatcgcatta aatgcacaag acgatttcag ttctactcca    1380
attacaatga attacaatca atttcttgag ttagaaaaaa cgaaacaatt aagattagat    1440
acggatcaag tatatgggaa tatagcaaca tacaattttg aaaatggaag agtgagggtg    1500
gatacaggct cgaactggag tgaagtgtta ccgcaaattc aagaaacaac tgcacgtatc    1560
atttttaatg gaaagatttt aaatctggta gaaaggcgga tagcggcggt taatcctagt    1620
gatccattag aaacgactaa accggatatg acattaaaag aagcccttaa aatagcattt    1680
ggatttaacg aaccgaatgg aaacttacaa tatcaaggga aagacataac cgaatttgat    1740
tttaatttcg atcaacaaac atctcaaaat atcaagaatc agttagcgga attaaacgca    1800
actaacatat atactgtatt agataaaatc aaattaaatg caaaaatgaa tattttaata    1860
agagataaac gttttcatta tgatagaaat aacatagcag ttggggcgga tgagtcagta    1920
gttaaggagg ctcatagaga agtaattaat tcgtcaacag agggattatt gttaaatatt    1980
gataaggata taagaaaaat attatcaggt tatattgtag aaattgaaga tactgaaggg    2040
cttaaagaag ttataaatga cagatatgat atgttgaata tttctagttt acggcaagat    2100
ggaaaaacat ttatagattt taaaaaatat aatgataaat taccgttata tataagtaat    2160
cccaattata aggtaaatgt atatgctgtt actaaagaaa acactattat taatcctagt    2220
gagaatgggg atactagtac caacgggatc aagaaaattt taatcttttc taaaaaaggc    2280
tatgagatag gataa                                                    2295
```

<210> SEQ ID NO 20
<211> LENGTH: 764
<212> TYPE: PRT
<213> ORGANISM: Artificial Sequence
<220> FEATURE:
<223> OTHER INFORMATION: Description of Artificial Sequence:modified
      homo-oligomeric anthrax toxin protective antigen
      (PrAg) PrAg-I210A
<220> FEATURE:
<221> NAME/KEY: SIGNAL
<222> LOCATION: (1)..(29)
<223> OTHER INFORMATION: signal peptide

<400> SEQUENCE: 20

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
             20                  25                  30

Gln Glu Asn Arg Leu Leu Asn Glu Ser Glu Ser Ser Ser Gln Gly Leu
         35                  40                  45

Leu Gly Tyr Tyr Phe Ser Asp Leu Asn Phe Gln Ala Pro Met Val Val
     50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
        115                 120                 125

Ala Ser Asn Ser Asn Lys Ile Arg Leu Glu Lys Gly Arg Leu Tyr Gln
    130                 135                 140

Ile Lys Ile Gln Tyr Gln Arg Glu Asn Pro Thr Glu Lys Gly Leu Asp
```

```
              145                 150                 155                 160
Phe Lys Leu Tyr Trp Thr Asp Ser Gln Asn Lys Lys Glu Val Ile Ser
                    165                 170                 175

Ser Asp Asn Leu Gln Leu Pro Glu Leu Lys Gln Lys Ser Ser Asn Ser
                180                 185                 190

Arg Lys Lys Arg Ser Thr Ser Ala Gly Pro Thr Val Pro Asp Arg Asp
                195                 200                 205

Asn Asp Gly Ile Pro Asp Ser Leu Glu Val Glu Gly Tyr Thr Val Asp
            210                 215                 220

Val Lys Asn Lys Arg Thr Phe Leu Ser Pro Trp Ile Ser Asn Ala His
225                 230                 235                 240

Glu Lys Lys Gly Leu Thr Lys Tyr Lys Ser Ser Pro Glu Lys Trp Ser
                    245                 250                 255

Thr Ala Ser Asp Pro Tyr Ser Asp Phe Glu Lys Val Thr Gly Arg Ile
                260                 265                 270

Asp Lys Asn Val Ser Pro Glu Ala Arg His Pro Leu Val Ala Ala Tyr
            275                 280                 285

Pro Ile Val His Val Asp Met Glu Asn Ile Ile Leu Ser Lys Asn Glu
        290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                    325                 330                 335

Glu Val His Ala Ser Phe Phe Asp Ile Gly Gly Ser Val Ser Ala Gly
                340                 345                 350

Phe Ser Asn Ser Asn Ser Ser Thr Val Ala Ile Asp His Ser Leu Ser
                355                 360                 365

Leu Ala Gly Glu Arg Thr Trp Ala Glu Thr Met Gly Leu Asn Thr Ala
        370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                    405                 410                 415

Asn Gln Thr Leu Ala Thr Ile Lys Ala Lys Glu Asn Gln Leu Ser Gln
                420                 425                 430

Ile Leu Ala Pro Asn Asn Tyr Tyr Pro Ser Lys Asn Leu Ala Pro Ile
            435                 440                 445

Ala Leu Asn Ala Gln Asp Asp Phe Ser Ser Thr Pro Ile Thr Met Asn
        450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                    485                 490                 495

Arg Val Arg Val Asp Thr Gly Ser Asn Trp Ser Glu Val Leu Pro Gln
                500                 505                 510

Ile Gln Glu Thr Thr Ala Arg Ile Ile Phe Asn Gly Lys Asp Leu Asn
            515                 520                 525

Leu Val Glu Arg Arg Ile Ala Ala Val Asn Pro Ser Asp Pro Leu Glu
        530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                    565                 570                 575
```

```
Thr Glu Phe Asp Phe Asn Phe Asp Gln Gln Thr Ser Gln Asn Ile Lys
            580                 585                 590

Asn Gln Leu Ala Glu Leu Asn Ala Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
690                 695                 700

Ile Asp Phe Lys Lys Tyr Asn Asp Lys Leu Pro Leu Tyr Ile Ser Asn
705                 710                 715                 720

Pro Asn Tyr Lys Val Asn Val Tyr Ala Val Thr Lys Glu Asn Thr Ile
                725                 730                 735

Ile Asn Pro Ser Glu Asn Gly Asp Thr Ser Thr Asn Gly Ile Lys Lys
            740                 745                 750

Ile Leu Ile Phe Ser Lys Lys Gly Tyr Glu Ile Gly
        755                 760

<210> SEQ ID NO 21
<211> LENGTH: 8
<212> TYPE: PRT
<213> ORGANISM: Artificial Sequence
<220> FEATURE:
<223> OTHER INFORMATION: Description of Artificial Sequence:matrix
      metalloproteinase (MMP) cleavage site

<400> SEQUENCE: 21

Gly Pro Leu Pro Met Leu Ser Gln
 1               5

<210> SEQ ID NO 22
<211> LENGTH: 8
<212> TYPE: PRT
<213> ORGANISM: Artificial Sequence
<220> FEATURE:
<223> OTHER INFORMATION: Description of Artificial Sequence:matrix
      metalloproteinase (MMP) cleavage site

<400> SEQUENCE: 22

Gly Pro Leu Pro Leu Trp Ala Gln
 1               5

<210> SEQ ID NO 23
<211> LENGTH: 7
<212> TYPE: PRT
<213> ORGANISM: Artificial Sequence
<220> FEATURE:
<223> OTHER INFORMATION: Description of Artificial Sequence:plasminogen
      activator cleavage site

<400> SEQUENCE: 23

Pro Gly Ser Gly Arg Ser Ala
 1               5

<210> SEQ ID NO 24
```

```
<211> LENGTH: 7
<212> TYPE: PRT
<213> ORGANISM: Artificial Sequence
<220> FEATURE:
<223> OTHER INFORMATION: Description of Artificial Sequence:plasminogen
      activator cleavage site

<400> SEQUENCE: 24

Pro Gly Ser Gly Lys Ser Ala
  1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence:matrix
      metalloproteinase (MMP) cleavage site

<400> SEQUENCE: 25

Gly Pro Leu Gly Met Leu Ser Gln
  1               5

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:native furin
      cleavage site, cell surface furin or furin-like
      protease cleavage site

<400> SEQUENCE: 26

Arg Lys Lys Arg
  1

<210> SEQ ID NO 27
<211> LENGTH: 8
<212> TYPE: PRT
<213> ORGANISM: Artificial Sequence
<220> FEATURE:
<223> OTHER INFORMATION: Description of Artificial Sequence:matrix
      metalloproteinase (MMP) cleavage site

<400> SEQUENCE: 27

Gly Pro Leu Gly Leu Trp Ala Gln
  1               5

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence:plasminogen
      activator cleavage site, uPA and tPA physiological
      substrate sequence

<400> SEQUENCE: 28

Pro Cys Pro Gly Arg Val Val Gly Gly
  1               5

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence:plasminogen
      activator cleavage site

<400> SEQUENCE: 29
```

Pro Gln Arg Gly Arg Ser Ala
 1               5

<210> SEQ ID NO 30
<211> LENGTH: 6
<212> TYPE: PRT
<213> ORGANISM: Artificial Sequence
<220> FEATURE:
<223> OTHER INFORMATION: Description of Artificial Sequence:plasminogen
      activator cleavage site, uPA favorite sequence

<400> SEQUENCE: 30

Gly Ser Gly Arg Ser Ala
 1               5

<210> SEQ ID NO 31
<211> LENGTH: 6
<212> TYPE: PRT
<213> ORGANISM: Artificial Sequence
<220> FEATURE:
<223> OTHER INFORMATION: Description of Artificial Sequence:plasminogen
      activator cleavage site, uPA favorite sequence

<400> SEQUENCE: 31

Gly Ser Gly Lys Ser Ala
 1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence:plasminogen
      activator cleavage site, tPA favorite sequence

<400> SEQUENCE: 32

Gln Arg Gly Arg Ser Ala
 1               5

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence:sense primer
      Pn

<400> SEQUENCE: 33
ggtagatgac caagaagtga                                            20

<210> SEQ ID NO 34
<211> LENGTH: 52
<212> TYPE: DNA
<213> ORGANISM: Artificial Sequence
<220> FEATURE:
<223> OTHER INFORMATION: Description of Artificial Sequence:antisense
      primer Pk197a

<400> SEQUENCE: 34
aaatccatgg tgaaagaaaa gttcttttat ttgcgacatc aaccgtatat cc         52

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence:antisense
      primer Pr200a

<400> SEQUENCE: 35
aaatccatgg tgaaagaaaa gttgctttat ttttgacatc aaccg            45

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence:sense primer
      Pnco

<400> SEQUENCE: 36
ttcaccatgg atttctaata ttcatg                                 26

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence:antisense
      primer Ppst

<400> SEQUENCE: 37
taaatcctgc agatacactc ccaccaat                               28

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence:antisense
      primer Pr178a-1

<400> SEQUENCE: 38
agggatccca tcattgtcag cgtctggaac cgtaggtcc                   39

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence:sense primer
      Pr178a-2

<400> SEQUENCE: 39
tgggatccct gattcattag aggtagaagg                             30

<210> SEQ ID NO 40
<211> LENGTH: 36
<212> TYPE: DNA
<213> ORGANISM: Artificial Sequence
<220> FEATURE:
<223> OTHER INFORMATION: Description of Artificial Sequence:sense primer
      Pi210a

<400> SEQUENCE: 40
ttcaccatgg atttctaatg ctcatgaaaa gaaagg                      36

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence:antisense
      primer Pli4

<400> SEQUENCE: 41

-continued

```
acgtttatct cttattaaaa t                                              21
```

<210> SEQ ID NO 42
<211> LENGTH: 50
<212> TYPE: DNA
<213> ORGANISM: Artificial Sequence
<220> FEATURE:
<223> OTHER INFORMATION: Description of Artificial Sequence:sense primer
      Pk214a

<400> SEQUENCE: 42

```
ttcaccatgg atttctaata ttcatgaaaa ggcaggatta accaaatata              50
```

<210> SEQ ID NO 43
<211> LENGTH: 764
<212> TYPE: PRT
<213> ORGANISM: Bacillus anthracis
<220> FEATURE:
<223> OTHER INFORMATION: anthrax toxin protective antigen (PrAg, pagA,
      pXO1-110) component

<400> SEQUENCE: 43

```
Met Lys Lys Arg Lys Val Leu Ile Pro Leu Met Ala Leu Ser Thr Ile
  1               5                  10                  15

Leu Val Ser Ser Thr Gly Asn Leu Glu Val Ile Gln Ala Glu Val Lys
                 20                  25                  30

Gln Glu Asn Arg Leu Leu Asn Glu Ser Glu Ser Ser Ser Gln Gly Leu
             35                  40                  45

Leu Gly Tyr Tyr Phe Ser Asp Leu Asn Phe Gln Ala Pro Met Val Val
         50                  55                  60

Thr Ser Ser Thr Thr Gly Asp Leu Ser Ile Pro Ser Ser Glu Leu Glu
 65                  70                  75                  80

Asn Ile Pro Ser Glu Asn Gln Tyr Phe Gln Ser Ala Ile Trp Ser Gly
                 85                  90                  95

Phe Ile Lys Val Lys Lys Ser Asp Glu Tyr Thr Phe Ala Thr Ser Ala
            100                 105                 110

Asp Asn His Val Thr Met Trp Val Asp Asp Gln Glu Val Ile Asn Lys
            115                 120                 125

Ala Ser Asn Ser Asn Lys Ile Arg Leu Glu Lys Gly Arg Leu Tyr Gln
        130                 135                 140

Ile Lys Ile Gln Tyr Gln Arg Glu Asn Pro Thr Glu Lys Gly Leu Asp
145                 150                 155                 160

Phe Lys Leu Tyr Trp Thr Asp Ser Gln Asn Lys Lys Glu Val Ile Ser
                165                 170                 175

Ser Asp Asn Leu Gln Leu Pro Glu Leu Lys Gln Lys Ser Ser Asn Ser
            180                 185                 190

Arg Lys Lys Arg Ser Thr Ser Ala Gly Pro Thr Val Pro Asp Arg Asp
        195                 200                 205

Asn Asp Gly Ile Pro Asp Ser Leu Glu Val Glu Gly Tyr Thr Val Asp
    210                 215                 220

Val Lys Asn Lys Arg Thr Phe Leu Ser Pro Trp Ile Ser Asn Ile His
225                 230                 235                 240

Glu Lys Lys Gly Leu Thr Lys Tyr Lys Ser Ser Pro Glu Lys Trp Ser
                245                 250                 255

Thr Ala Ser Asp Pro Tyr Ser Asp Phe Glu Lys Val Thr Gly Arg Ile
            260                 265                 270

Asp Lys Asn Val Ser Pro Glu Ala Arg His Pro Leu Val Ala Ala Tyr
        275                 280                 285
```

```
Pro Ile Val His Val Asp Met Glu Asn Ile Ile Leu Ser Lys Asn Glu
    290                 295                 300

Asp Gln Ser Thr Gln Asn Thr Asp Ser Gln Thr Arg Thr Ile Ser Lys
305                 310                 315                 320

Asn Thr Ser Thr Ser Arg Thr His Thr Ser Glu Val His Gly Asn Ala
                325                 330                 335

Glu Val His Ala Ser Phe Phe Asp Ile Gly Gly Ser Val Ser Ala Gly
            340                 345                 350

Phe Ser Asn Ser Asn Ser Ser Thr Val Ala Ile Asp His Ser Leu Ser
        355                 360                 365

Leu Ala Gly Glu Arg Thr Trp Ala Glu Thr Met Gly Leu Asn Thr Ala
    370                 375                 380

Asp Thr Ala Arg Leu Asn Ala Asn Ile Arg Tyr Val Asn Thr Gly Thr
385                 390                 395                 400

Ala Pro Ile Tyr Asn Val Leu Pro Thr Thr Ser Leu Val Leu Gly Lys
                405                 410                 415

Asn Gln Thr Leu Ala Thr Ile Lys Ala Lys Glu Asn Gln Leu Ser Gln
            420                 425                 430

Ile Leu Ala Pro Asn Asn Tyr Tyr Pro Ser Lys Asn Leu Ala Pro Ile
        435                 440                 445

Ala Leu Asn Ala Gln Asp Asp Phe Ser Ser Thr Pro Ile Thr Met Asn
    450                 455                 460

Tyr Asn Gln Phe Leu Glu Leu Glu Lys Thr Lys Gln Leu Arg Leu Asp
465                 470                 475                 480

Thr Asp Gln Val Tyr Gly Asn Ile Ala Thr Tyr Asn Phe Glu Asn Gly
                485                 490                 495

Arg Val Arg Val Asp Thr Gly Ser Asn Trp Ser Glu Val Leu Pro Gln
            500                 505                 510

Ile Gln Glu Thr Thr Ala Arg Ile Ile Phe Asn Gly Lys Asp Leu Asn
        515                 520                 525

Leu Val Glu Arg Arg Ile Ala Ala Val Asn Pro Ser Asp Pro Leu Glu
    530                 535                 540

Thr Thr Lys Pro Asp Met Thr Leu Lys Glu Ala Leu Lys Ile Ala Phe
545                 550                 555                 560

Gly Phe Asn Glu Pro Asn Gly Asn Leu Gln Tyr Gln Gly Lys Asp Ile
                565                 570                 575

Thr Glu Phe Asp Phe Asn Phe Asp Gln Gln Thr Ser Gln Asn Ile Lys
            580                 585                 590

Asn Gln Leu Ala Glu Leu Asn Val Thr Asn Ile Tyr Thr Val Leu Asp
        595                 600                 605

Lys Ile Lys Leu Asn Ala Lys Met Asn Ile Leu Ile Arg Asp Lys Arg
    610                 615                 620

Phe His Tyr Asp Arg Asn Asn Ile Ala Val Gly Ala Asp Glu Ser Val
625                 630                 635                 640

Val Lys Glu Ala His Arg Glu Val Ile Asn Ser Ser Thr Glu Gly Leu
                645                 650                 655

Leu Leu Asn Ile Asp Lys Asp Ile Arg Lys Ile Leu Ser Gly Tyr Ile
            660                 665                 670

Val Glu Ile Glu Asp Thr Glu Gly Leu Lys Glu Val Ile Asn Asp Arg
        675                 680                 685

Tyr Asp Met Leu Asn Ile Ser Ser Leu Arg Gln Asp Gly Lys Thr Phe
    690                 695                 700

Ile Asp Phe Lys Lys Tyr Asn Asp Lys Leu Pro Leu Tyr Ile Ser Asn
```

```
                                  705                 710                 715                 720
Pro Asn Tyr Lys Val Asn Val Tyr Ala Val Thr Lys Glu Asn Thr Ile
                    725                 730                 735

Ile Asn Pro Ser Glu Asn Gly Asp Thr Ser Thr Asn Gly Ile Lys Lys
                    740                 745                 750

Ile Leu Ile Phe Ser Lys Lys Gly Tyr Glu Ile Gly
                    755                 760

<210> SEQ ID NO 44
<211> LENGTH: 809
<212> TYPE: PRT
<213> ORGANISM: Bacillus anthracis
<220> FEATURE:
<223> OTHER INFORMATION: anthrax toxin lethal factor (LF, lef, pXO1-107)
      precursor component

<400> SEQUENCE: 44

Met Asn Ile Lys Lys Glu Phe Ile Lys Val Ile Ser Met Ser Cys Leu
  1               5                  10                  15

Val Thr Ala Ile Thr Leu Ser Gly Pro Val Phe Ile Pro Leu Val Gln
                 20                  25                  30

Gly Ala Gly Gly His Gly Asp Val Gly Met His Val Lys Glu Lys Glu
             35                  40                  45

Lys Asn Lys Asp Glu Asn Lys Arg Lys Asp Glu Glu Arg Asn Lys Thr
 50                  55                  60

Gln Glu Glu His Leu Lys Glu Ile Met Lys His Ile Val Lys Ile Glu
 65                  70                  75                  80

Val Lys Gly Glu Glu Ala Val Lys Lys Glu Ala Ala Glu Lys Leu Leu
                 85                  90                  95

Glu Lys Val Pro Ser Asp Val Leu Glu Met Tyr Lys Ala Ile Gly Gly
                100                 105                 110

Lys Ile Tyr Ile Val Asp Gly Asp Ile Thr Lys His Ile Ser Leu Glu
            115                 120                 125

Ala Leu Ser Glu Asp Lys Lys Lys Ile Lys Asp Ile Tyr Gly Lys Asp
        130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe Ala Tyr
                245                 250                 255

Tyr Ile Glu Pro Gln His Arg Asp Val Leu Gln Leu Tyr Ala Pro Glu
            260                 265                 270

Ala Phe Asn Tyr Met Asp Lys Phe Asn Glu Gln Glu Ile Asn Leu Ser
        275                 280                 285

Leu Glu Glu Leu Lys Asp Gln Arg Met Leu Ser Arg Tyr Glu Lys Trp
    290                 295                 300

Glu Lys Ile Lys Gln His Tyr Gln His Trp Ser Asp Ser Leu Ser Glu
```

-continued

```
          305                 310                 315                 320

Glu Gly Arg Gly Leu Leu Lys Lys Leu Gln Ile Pro Ile Glu Pro Lys
                325                 330                 335

Lys Asp Asp Ile Ile His Ser Leu Ser Gln Glu Glu Lys Glu Leu Leu
                340                 345                 350

Lys Arg Ile Gln Ile Asp Ser Ser Asp Phe Leu Ser Thr Glu Glu Lys
                355                 360                 365

Glu Phe Leu Lys Lys Leu Gln Ile Asp Ile Arg Asp Ser Leu Ser Glu
                370                 375                 380

Glu Glu Lys Glu Leu Leu Asn Arg Ile Gln Val Asp Ser Ser Asn Pro
385                 390                 395                 400

Leu Ser Glu Lys Glu Lys Glu Phe Leu Lys Lys Leu Lys Leu Asp Ile
                405                 410                 415

Gln Pro Tyr Asp Ile Asn Gln Arg Leu Gln Asp Thr Gly Gly Leu Ile
                420                 425                 430

Asp Ser Pro Ser Ile Asn Leu Asp Val Arg Lys Gln Tyr Lys Arg Asp
                435                 440                 445

Ile Gln Asn Ile Asp Ala Leu Leu His Gln Ser Ile Gly Ser Thr Leu
450                 455                 460

Tyr Asn Lys Ile Tyr Leu Tyr Glu Asn Met Asn Ile Asn Asn Leu Thr
465                 470                 475                 480

Ala Thr Leu Gly Ala Asp Leu Val Asp Ser Thr Asp Asn Thr Lys Ile
                485                 490                 495

Asn Arg Gly Ile Phe Asn Glu Phe Lys Lys Asn Phe Lys Tyr Ser Ile
                500                 505                 510

Ser Ser Asn Tyr Met Ile Val Asp Ile Asn Glu Arg Pro Ala Leu Asp
                515                 520                 525

Asn Glu Arg Leu Lys Trp Arg Ile Gln Leu Ser Pro Asp Thr Arg Ala
                530                 535                 540

Gly Tyr Leu Glu Asn Gly Lys Leu Ile Leu Gln Arg Asn Ile Gly Leu
545                 550                 555                 560

Glu Ile Lys Asp Val Gln Ile Ile Lys Gln Ser Glu Lys Glu Tyr Ile
                565                 570                 575

Arg Ile Asp Ala Lys Val Val Pro Lys Ser Lys Ile Asp Thr Lys Ile
                580                 585                 590

Gln Glu Ala Gln Leu Asn Ile Asn Gln Glu Trp Asn Lys Ala Leu Gly
                595                 600                 605

Leu Pro Lys Tyr Thr Lys Leu Ile Thr Phe Asn Val His Asn Arg Tyr
                610                 615                 620

Ala Ser Asn Ile Val Glu Ser Ala Tyr Leu Ile Leu Asn Glu Trp Lys
625                 630                 635                 640

Asn Asn Ile Gln Ser Asp Leu Ile Lys Lys Val Thr Asn Tyr Leu Val
                645                 650                 655

Asp Gly Asn Gly Arg Phe Val Phe Thr Asp Ile Thr Leu Pro Asn Ile
                660                 665                 670

Ala Glu Gln Tyr Thr His Gln Asp Glu Ile Tyr Glu Gln Val His Ser
                675                 680                 685

Lys Gly Leu Tyr Val Pro Glu Ser Arg Ser Ile Leu Leu His Gly Pro
                690                 695                 700

Ser Lys Gly Val Glu Leu Arg Asn Asp Ser Glu Gly Phe Ile His Glu
705                 710                 715                 720

Phe Gly His Ala Val Asp Asp Tyr Ala Gly Tyr Leu Leu Asp Lys Asn
                725                 730                 735
```

-continued

```
Gln Ser Asp Leu Val Thr Asn Ser Lys Lys Phe Ile Asp Ile Phe Lys
            740                 745                 750

Glu Glu Gly Ser Asn Leu Thr Ser Tyr Gly Arg Thr Asn Glu Ala Glu
            755                 760                 765

Phe Phe Ala Glu Ala Phe Arg Leu Met His Ser Thr Asp His Ala Glu
770                 775                 780

Arg Leu Lys Val Gln Lys Asn Ala Pro Lys Thr Phe Gln Phe Ile Asn
785                 790                 795                 800

Asp Gln Ile Lys Phe Ile Ile Asn Ser
                805

<210> SEQ ID NO 45
<211> LENGTH: 800
<212> TYPE: PRT
<213> ORGANISM: Bacillus anthracis
<220> FEATURE:
<223> OTHER INFORMATION: anthrax toxin edema factor (EF, calmodulin
      sensitive anenylate cyclase, cya, pXO1-122)
      component

<400> SEQUENCE: 45

Met Thr Arg Asn Lys Phe Ile Pro Asn Lys Phe Ser Ile Ile Ser Phe
1               5                   10                  15

Ser Val Leu Leu Phe Ala Ile Ser Ser Gln Ala Ile Glu Val Asn
            20                  25                  30

Ala Met Asn Glu His Tyr Thr Glu Ser Asp Ile Lys Arg Asn His Lys
            35                  40                  45

Thr Glu Lys Asn Lys Thr Glu Lys Glu Lys Phe Lys Asp Ser Ile Asn
    50                  55                  60

Asn Leu Val Lys Thr Glu Phe Thr Asn Glu Thr Leu Asp Lys Ile Gln
65                  70                  75                  80

Gln Thr Gln Asp Leu Leu Lys Lys Ile Pro Lys Asp Val Leu Glu Ile
                85                  90                  95

Tyr Ser Glu Leu Gly Gly Glu Ile Tyr Phe Thr Asp Ile Asp Leu Val
            100                 105                 110

Glu His Lys Glu Leu Gln Asp Leu Ser Glu Glu Glu Lys Asn Ser Met
            115                 120                 125

Asn Ser Arg Gly Glu Lys Val Pro Phe Ala Ser Arg Phe Val Phe Glu
130                 135                 140

Lys Lys Arg Glu Thr Pro Lys Leu Ile Ile Asn Ile Lys Asp Tyr Ala
145                 150                 155                 160

Ile Asn Ser Glu Gln Ser Lys Glu Val Tyr Tyr Glu Ile Gly Lys Gly
                165                 170                 175

Ile Ser Leu Asp Ile Ile Ser Lys Asp Lys Ser Leu Asp Pro Glu Phe
            180                 185                 190

Leu Asn Leu Ile Lys Ser Leu Ser Asp Asp Ser Asp Ser Ser Asp Leu
            195                 200                 205

Leu Phe Ser Gln Lys Phe Lys Glu Lys Leu Glu Leu Asn Asn Lys Ser
210                 215                 220

Ile Asp Ile Asn Phe Ile Lys Glu Asn Leu Thr Glu Phe Gln His Ala
225                 230                 235                 240

Phe Ser Leu Ala Phe Ser Tyr Tyr Phe Ala Pro Asp His Arg Thr Val
                245                 250                 255

Leu Glu Leu Tyr Ala Pro Asp Met Phe Glu Tyr Met Asn Lys Leu Glu
            260                 265                 270

Lys Gly Gly Phe Glu Lys Ile Ser Glu Ser Leu Lys Lys Glu Gly Val
            275                 280                 285
```

```
Glu Lys Asp Arg Ile Asp Val Leu Lys Gly Glu Lys Ala Leu Lys Ala
    290                 295                 300

Ser Gly Leu Val Pro Glu His Ala Asp Ala Phe Lys Lys Ile Ala Arg
305                 310                 315                 320

Glu Leu Asn Thr Tyr Ile Leu Phe Arg Pro Val Asn Lys Leu Ala Thr
                325                 330                 335

Asn Leu Ile Lys Ser Gly Val Ala Thr Lys Gly Leu Asn Val His Gly
            340                 345                 350

Lys Ser Ser Asp Trp Gly Pro Val Ala Gly Tyr Ile Pro Phe Asp Gln
        355                 360                 365

Asp Leu Ser Lys Lys His Gly Gln Gln Leu Ala Val Glu Lys Gly Asn
    370                 375                 380

Leu Glu Asn Lys Lys Ser Ile Thr Glu His Glu Gly Glu Ile Gly Lys
385                 390                 395                 400

Ile Pro Leu Lys Leu Asp His Leu Arg Ile Glu Glu Leu Lys Glu Asn
                405                 410                 415

Gly Ile Ile Leu Lys Gly Lys Glu Ile Asp Asn Gly Lys Lys Tyr
            420                 425                 430

Tyr Leu Leu Glu Ser Asn Asn Gln Val Tyr Glu Phe Arg Ile Ser Asp
        435                 440                 445

Glu Asn Asn Glu Val Gln Tyr Lys Thr Lys Glu Gly Lys Ile Thr Val
    450                 455                 460

Leu Gly Glu Lys Phe Asn Trp Arg Asn Ile Glu Val Met Ala Lys Asn
465                 470                 475                 480

Val Glu Gly Val Leu Lys Pro Leu Thr Ala Asp Tyr Asp Leu Phe Ala
                485                 490                 495

Leu Ala Pro Ser Leu Thr Glu Ile Lys Lys Gln Ile Pro Gln Lys Glu
            500                 505                 510

Trp Asp Lys Val Val Asn Thr Pro Asn Ser Leu Glu Lys Gln Lys Gly
        515                 520                 525

Val Thr Asn Leu Leu Ile Lys Tyr Gly Ile Glu Arg Lys Pro Asp Ser
    530                 535                 540

Thr Lys Gly Thr Leu Ser Asn Trp Gln Lys Gln Met Leu Asp Arg Leu
545                 550                 555                 560

Asn Glu Ala Val Lys Tyr Thr Gly Tyr Thr Gly Gly Asp Val Val Asn
                565                 570                 575

His Gly Thr Glu Gln Asp Asn Glu Glu Phe Pro Glu Lys Asp Asn Glu
            580                 585                 590

Ile Phe Ile Ile Asn Pro Glu Gly Glu Phe Ile Leu Thr Lys Asn Trp
        595                 600                 605

Glu Met Thr Gly Arg Phe Ile Glu Lys Asn Ile Thr Gly Lys Asp Tyr
    610                 615                 620

Leu Tyr Tyr Phe Asn Arg Ser Tyr Asn Lys Ile Ala Pro Gly Asn Lys
625                 630                 635                 640

Ala Tyr Ile Glu Trp Thr Asp Pro Ile Thr Lys Ala Lys Ile Asn Thr
                645                 650                 655

Ile Pro Thr Ser Ala Glu Phe Ile Lys Asn Leu Ser Ser Ile Arg Arg
            660                 665                 670

Ser Ser Asn Val Gly Val Tyr Lys Asp Ser Gly Asp Lys Asp Glu Phe
        675                 680                 685

Ala Lys Lys Glu Ser Val Lys Lys Ile Ala Gly Tyr Leu Ser Asp Tyr
    690                 695                 700

Tyr Asn Ser Ala Asn His Ile Phe Ser Gln Glu Lys Lys Arg Lys Ile
```

```
                705                 710                 715                 720
Ser Ile Phe Arg Gly Ile Gln Ala Tyr Asn Glu Ile Glu Asn Val Leu
                    725                 730                 735

Lys Ser Lys Gln Ile Ala Pro Glu Tyr Lys Asn Tyr Phe Gln Tyr Leu
                    740                 745                 750

Lys Glu Arg Ile Thr Asn Gln Val Gln Leu Leu Thr His Gln Lys
            755                 760                 765

Ser Asn Ile Glu Phe Lys Leu Leu Tyr Lys Gln Leu Asn Phe Thr Glu
            770                 775                 780

Asn Glu Thr Asp Asn Phe Glu Val Phe Gln Lys Ile Ile Asp Glu Lys
785                 790                 795                 800

<210> SEQ ID NO 46
<211> LENGTH: 254
<212> TYPE: PRT
<213> ORGANISM: Artificial Sequence
<220> FEATURE:
<223> OTHER INFORMATION: Description of Artificial Sequence:amino acid
      residues 1-254 of anthrax toxin lethal factor (LFn)

<400> SEQUENCE: 46

Met Asn Ile Lys Lys Glu Phe Ile Lys Val Ile Ser Met Ser Cys Leu
1               5                   10                  15

Val Thr Ala Ile Thr Leu Ser Gly Pro Val Phe Ile Pro Leu Val Gln
                20                  25                  30

Gly Ala Gly Gly His Gly Asp Val Gly Met His Val Lys Glu Lys Glu
            35                  40                  45

Lys Asn Lys Asp Glu Asn Lys Arg Lys Asp Glu Glu Arg Asn Lys Thr
        50                  55                  60

Gln Glu Glu His Leu Lys Glu Ile Met Lys His Ile Val Lys Ile Glu
65                  70                  75                  80

Val Lys Gly Glu Glu Ala Val Lys Lys Glu Ala Ala Glu Lys Leu Leu
                85                  90                  95

Glu Lys Val Pro Ser Asp Val Leu Glu Met Tyr Lys Ala Ile Gly Gly
                100                 105                 110

Lys Ile Tyr Ile Val Asp Gly Asp Ile Thr Lys His Ile Ser Leu Glu
            115                 120                 125

Ala Leu Ser Glu Asp Lys Lys Lys Ile Lys Asp Ile Tyr Gly Lys Asp
    130                 135                 140

Ala Leu Leu His Glu His Tyr Val Tyr Ala Lys Glu Gly Tyr Glu Pro
145                 150                 155                 160

Val Leu Val Ile Gln Ser Ser Glu Asp Tyr Val Glu Asn Thr Glu Lys
                165                 170                 175

Ala Leu Asn Val Tyr Tyr Glu Ile Gly Lys Ile Leu Ser Arg Asp Ile
            180                 185                 190

Leu Ser Lys Ile Asn Gln Pro Tyr Gln Lys Phe Leu Asp Val Leu Asn
        195                 200                 205

Thr Ile Lys Asn Ala Ser Asp Ser Asp Gly Gln Asp Leu Leu Phe Thr
    210                 215                 220

Asn Gln Leu Lys Glu His Pro Thr Asp Phe Ser Val Glu Phe Leu Glu
225                 230                 235                 240

Gln Asn Ser Asn Glu Val Gln Glu Val Phe Ala Lys Ala Phe
                245                 250
```

MULTIMERIC PROTEIN TOXINS TO TARGET CELLS HAVING MULTIPLE IDENTIFYING CHARACTERISTICS

CROSS-REFERENCES TO RELATED APPLICATIONS

This application is a division of U.S. patent application Ser. No. 11/055,557, now U.S. Pat. No. 7,947,289, filed Feb. 9, 2005, which claims priority to U.S. Provisional Patent Application No. 60/543,417, filed Feb. 9, 2004, the contents of each of the above are hereby incorporated by reference in the entirety for all purposes.

BACKGROUND OF THE INVENTION

Many multimeric bacterial toxins that comprise monomers or subunits that comprise monomers are known in the art. These include multimeric pore-forming toxins which lack a second catalytic effector domain or molecule, and multimeric binary toxins which comprise a second catalytic effector domain or molecule. Staphylococcal α-hemolysin, Staphylococcal leukocidin, aerolysin (e.g., from *Aeromonas hydrophile*), *Clostridium septicum* α toxin, *Bacillus cereus* hemolysis II, and *Helicobacter pylori* vacuolating toxin (VacA) are examples of multimeric pore-forming toxins which lack a second catalytic effector domain. Anthrax toxin, cholera toxin, *E. coli* heat-labile enterotoxin, Shiga toxin, pertussis toxin, *Clostridium perfringens* iota toxin, *Clostridium spiroforme* toxin, *Clostridium difficile* binary toxin, *Clostridium botulinum* C2 toxin, and *Bacillus cereus* vegetative insecticidal protein are examples of multimeric binary toxins which comprise a second catalytic effector domain or molecule. The interaction between catalytic effector domain of these toxins and target cells leads to the toxic effects of these toxins. For example, anthrax toxin lethal factor (LF), cholera toxin subunit A, Shiga toxin subunit A, *C. perfringens* iota toxin 1a component 1a (an ADP-ribosyltransferase), *C. spiroforme* toxin subunit A, *C. difficile* toxin subunit A, a *C. botulinum* C2 subunit A; and *B. cereus* vegetative insecticidal protein subunit A each serve as the catalytic effector domain of their respective toxins.

Homo-oligomeric bacterial toxins with modified monomers have been designed and used to target particular cell populations. For example, Liu et al., *PNAS USA* 100(2):657-662 (2003) describe use of a modified homo-oligomeric anthrax toxin protective antigen (PrAg) in which the native furin cleavage site has been replaced by a urokinase plasminogen activator cleavage site to target and kill melanoma cells, fibrosarcoma cells, and lung carcinoma cells in vivo. Liu et al., *J. Biol. Chem.*, 276(21): 17976-17984 (2001) describe use of a modified homo-oligomeric PrAg in which the native furin cleavage site has been replaced by a urokinase plasminogen activator cleavage site to target and kill melanoma cells, adenocarcinoma cells, and lung carcinoma cells in vitro. Liu et al., *Cancer Res.* 60:6061-6067 (2000) and WO 01/21656 describe use of a modified homo-oligomeric PrAg in which the native furin cleavage site has been replaced by a matrix metalloproteinase cleavage site (e.g., for MMP-2 or MMP-9) to target and kill melanoma cells, fibrosarcoma cells, and breast cancer cells in vitro. These homo-oligomeric PrAg comprising modified monomers are also described in Liu et al., *Expert Opin. Biol. Ther.* 3(5):843-853 (2003). U.S. Pat. No. 5,677,274 describes, inter alia, use of a modified PrAg in which the native trypsin cleavage site has been replaced by a cleavage site for HIV-1 protease to target and kill HIV-infected cells in vitro. WO 03/033648 describes use of a modified anthrax toxin protective antigen (PrAg) in which the native furin cleavage site has been replaced by a matrix metalloproteinase cleavage site or a plasminogen activator cleavage site to target and detect, i.e., image, target cells expressing matrix metalloproteinases or plasminogen activators on their surface.

Hetero-oligomeric bacterial toxins based on binary bacterial toxins have also been designed. These toxins have been used to explore the interactions between one component of the binary toxins (e.g., the binding component and the catalytic effector component) as well as the interactions between the monomers themselves. Mogridge et al., *PNAS USA* 99(10):7045-7048 (2002) describe a modified hetero-oligomeric PrAg comprising two types of modified monomers in which the monomer binding sites have been mutated so that the two types of monomers can only form oligomers with each other. Cunningham et al., *PNAS USA* 99(10):7049-7053 (2002) describe a modified hetero-oligomeric PrAg comprising two types of modified monomers in which the LF binding sites have been modified so that both types of monomers are required to bind LF.

Thus, bacterial toxins have been used in the development of homo-oligomeric and hetero-oligomeric toxins. The homo-oligomeric toxins, in particular, have been used to target specific cell populations (e.g., cancer cells or virally infected cells). The monomers of the homo-oligomeric toxins were modified to take advantage of a single characteristic of the target cell population. More particularly, the monomers were modified to replace a native proteolytic cleavage site with a cleavage site for a cell surface protease (e.g., MMP or plasminogen activator) overexpressed in the target cells, and thus specifically target these cells. The homo-oligomeric toxins can sometimes target normal cells which share the single characteristic of the target cell population. Therefore, hetero-oligomeric toxins which rely on multiple characteristics of a cell population are likely to have increased target cell specificity and decreased non-specific toxicity to non-target cells.

Thus, there is a need in the art for additional modified bacterial toxins which have greater specificity for a particular target cell population, i.e., toxins that target cells based on more than one target cell characteristic, and methods of using such toxins. The present invention addresses these and other needs.

BRIEF SUMMARY OF THE INVENTION

The present invention provides compositions comprising modified bacterial toxins and methods for targeting specific cell populations using the modified bacterial toxins.

In one embodiment, the present invention provides compositions comprising a first effector component of a multimeric bacterial protein toxin (e.g., Staphylococcal α-hemolysin, Staphylococcal leukocidin, aerolysin (e.g., from *Aeromonas hydrophile*), *Clostridium septicum* α toxin, *Bacillus cereus* hemolysis II, *Helicobacter pylori* vacuolating toxin (VacA), anthrax toxin, cholera toxin, *E. coli* heat-labile enterotoxin, Shiga toxin, pertussis toxin, *Clostridium perfringens* iota toxin, *Clostridium spiroforme* toxin, *Clostridium difficile* binary toxin, *Clostridium botulinum* C2 toxin, and *Bacillus cereus* vegetative insecticidal protein). The first effector component comprises at least a first monomer and a second monomer that are different from each other and form a heterooligomer. The first and second monomers are each modified by at least two of the following methods: (a) substitution of a native cell-recognition domain for a non-native cell-recognition domain; (b) substitution of a native proteolytic activation site for a non-native proteolytic activation site; (c) modification of the first monomer to generate a first modified monomer, whereby the first modified monomer can pair only with the second monomer; (d) modification of the first monomer and the second monomer, whereby a second effector component can bind only at a site formed by the interaction of the first monomer and the second monomer molecule; or (e) a combination thereof In some embodiments, (a) comprises substituting a native cell-recognition domain for a non-native cell recognition domain selected from the group consisting of: an antibody, a cytokine, a cell surface receptor ligand, or a combination thereof (b) comprises substituting a native furin cleavage site for a cleavage site for a metalloproteinase, a cysteine protease, an aspartic acid protease, a plasminogen activator, a kallikrein, a type 1 transmembrane serine protease, a type 2 transmembrane serine protease, or a GPI anchored serine protease; (c) comprises mutating the first monomer and the second monomer at least two times, whereby the first mutation generates a first modified monomer comprising a binding site that binds only a monomer binding site of the second monomer, and whereby the second mutation generates a monomer comprising a binding site that binds only a monomer binding site of a third monomer, wherein the first, second, and third monomer are each different. In some embodiments, thee first effector component forms a multimeric bacterial protein toxin component comprising at least five, six, or seven monomers. In some embodiments, the second effector component is selected from anthrax lethal factor (LF), anthrax edema factor (EF), amino acid residues 1-254 of anthrax lethal factor (LFn), amino acid residues 1-254 of anthrax lethal factor (LFn) fused to a heterologous polypeptide (e.g., *Pseudomonas* exotoxin A). In some embodiments, the first monomer and second monomer each comprise at least two modifications selected from (a) and (b); (b) and (c); (c) and (d); (a) and (c); (a) and (d); and (b) and (d). In some embodiments, the compositions comprise a third monomer that is different from the first monomer and the second monomer, and wherein the third monomer is modified by at least two methods selected from (a); (b); (c); (d); and (e).

In some embodiments, the first monomer is a first anthrax protective antigen monomer and the second monomer is a second anthrax protective antigen monomer. In these embodiments, (b) comprises substituting a native furin cleavage site of the first anthrax protective antigen monomer and the second anthrax protective antigen monomer for a cleavage site for a metalloproteinase (e.g., MMP-1, MMP-2, MMP-9, MMP-13, MMP-14, or MT2-MMP), a cysteine protease, an aspartic acid protease, a plasminogen activator (e.g., a urokinase plasminogen activator or a tissue plasminogen activator), a kallikrein (e.g., KLK2 or KLK3/PSA), a type 1 transmembrane serine protease, a type 2 transmembrane serine protease (e.g., hepsin or matriptase), or a GPI anchored serine protease; (c) comprises mutating an oligomerization site of the first anthrax protective antigen monomer and an oligomerization site of the second anthrax protective antigen site, whereby the first anthrax protective antigen monomer and second anthrax protective antigen monomer can bind to each other; and (d) comprises mutating a lethal factor binding site of the first anthrax protective antigen monomer and mutating a lethal factor binding site of the second anthrax protective antigen monomer, whereby the first anthrax protective antigen monomer and the second anthrax protective antigen monomer are both required to bind the lethal factor. In some embodiment, the cleavage site for a metalloproteinase or a plasminogen activator is selected from the group consisting of: GPLPMLSQ(SEQ ID NO:21), GPLPLWAQ(SEQ ID NO:22), PGSGRSA(SEQ ID NO:23), and PGSGKSA(SEQ ID NO:24). In some embodiments, (b) comprises substituting a native furin cleavage site of the first anthrax protective antigen monomer for a cleavage site for a plasminogen activator and of the second anthrax protective antigen monomer for a cleavage site for a metalloproteinase. In some embodiments, (d) comprises mutating the first anthrax protective antigen monomer by making a substitution selected from: arginine at position 178 with alanine; lysine at position 197 with alanine; arginine at position 200 with alanine; isoleucine at position 207 with alanine; isoleucine at position 210 with alanine; lysine at position 214 with alanine; and a combination thereof; and mutating the second anthrax protective antigen monomer by making a substitution selected from: arginine at position 178 with alanine; lysine at position 197 with alanine; arginine at position 200 with alanine; isoleucine at position 207 with alanine; isoleucine at position 210 with alanine; lysine at position 214 with alanine; and a combination thereof. In some embodiments, (d) comprises mutating the first anthrax protective antigen monomer by making a substitution selected from: arginine at position 200 with alanine and lysine at position 197 with alanine; and mutating the second anthrax protective antigen monomer by making a substitution selected from: arginine at position 178 with alanine; isoleucine at position 210 with alanine and lysine at position 214 with alanine. In some embodiments, (b) comprises substituting a native furin cleavage site of the first anthrax protective antigen monomer for a cleavage site for a plasminogen activator and of the second anthrax protective antigen monomer for a cleavage site for a matrix metalloproteinase; and (d) comprises mutating the first anthrax protective antigen monomer by substituting: arginine at position 200 with alanine and mutating the second anthrax protective antigen monomer by substituting isoleucine at position 210 with alanine In some embodiments, (b) comprises substituting a native furin cleavage site of the first anthrax protective antigen monomer for PGSGRSA(SEQ ID NO:23) and the second anthrax protective antigen monomer for GPLGMLSQ (SEQ ID NO:25). In some embodiments, the native cell-recognition domain is substituted for a cytokine (e.g., IL-2 and GM-CSF). The invention further provides pharmaceutical compositions comprising the effector molecules described herein and a pharmaceutically acceptable carrier.

Another embodiment provides a method of treating a disease by administering the compositions to a patient. In some embodiments, the disease is cancer (e.g., carcinoma, sarcoma, lymphoma, leukemia, melanoma, colon cancer, breast cancer, bladder cancer, thyroid cancer, liver cancer, pleural cancer, lung cancer, ovarian cancer, pancreatic cancer, head and neck cancer, kidney cancer, multiple myeloma, stomach cancer, brain cancer, Hodgkin's lymphoma, non-Hodgkin's lymphoma and a combination thereof). In some embodiments, the cancer cell expresses at least two proteolytic enzymes (e.g., enzymes selected from a metalloproteinase, a cysteine protease, an aspartic acid protease, a plasminogen activator, a kallikrein, a type 1 transmembrane serine protease, a type 2 transmembrane serine protease, or a GPI anchored serine protease, and a combination thereof). In some embodiments, the disease is a viral infection (e.g., an HIV infection, a CMV infection, a HPV infection, a HBV infection, a HCV infection , a HSV infection, and a HZV infection). In some embodiments, the disease is an autoimmune disease (e.g., rheumatoid arthritis ("RA"), diabetes mellitus ("DM"), myasthenia gravis ("MG"), systemic lupus erythematosus ("SLE"), Grave's disease, or Addison's disease.

A further embodiment of the invention provides a method of targeting a cell by contacting the cell with the compositions disclosed herein. In some embodiments, the cell is in a mammal (e.g., a rodent such as a mouse, a rat or, a gerbil, a canine such as a dog, feline such as a cat, a primate such as a chimpanzee, a rhesus monkey, a gorilla, and orangatun, or a human). In some embodiments, the cell is killed by contacting. In some embodiments, the cell is detected after the contacting. In some embodiments, the cell is a disease cell (e.g., a cancer cell or a virally infected cell.

Even another embodiment of the invention provides a polypeptide monomer of a first effector component of a multimeric bacterial protein toxin, the first effector component comprising at least a first monomer and a second monomer, wherein the first and second monomers form a heterooligomer, wherein the first and second monomers are different, and wherein the first and second monomers are each modified by at least two of the following methods: (a) substitution of a native cell-recognition domain for a non-native cell-recognition domain; (b) substitution of a native proteolytic activation site for a non-native proteolytic activation site; (c) modification of the first monomer to generate a first modified monomer, whereby the first modified monomer can pair only with the second monomer; (d) modification of the first monomer and the second monomer, whereby a second effector component can bind only at a site formed by the interaction of the first monomer and the second monomer molecule; or (e) a combination thereof.

In a further embodiment, the invention provides isolated nucleic acids comprising the sequences set forth in SEQ ID NOS: 1, 3, 5, 7, 9, 15, or 19, and isolated polypeptides comprising the sequences set forth in SEQ ID NOS: 2, 4, 6, 8, 10, 16, or 20.

BRIEF DESCRIPTION OF THE DRAWINGS

FIG. 1 is a schematic representation of intermolecular complementation by mutated PrAg proteins. LF-binding subsites I, II, and III are represented as I, II, and III, respectively. LF-binding subsites I and III and subsite II that together comprise one LF-binding site are located on adjacent PrAg63 subunits. Mutations in any of these subsites result in the impaired LF-binding sites on PrAg heptamers. However, up to three active LF-binding sites can be regained by intermolecular complementation of the two PrAg monomers with different LF-binding subsites mutations, such as in II and III as shown in the figure.

FIG. 4 illustrates data demonstrating that PrAg modified to comprise different LF-binding subsite mutations can complement LF-binding and toxicity. FIG. 4A demonstrate intermolecular complementation by PrAg-R200A and PrAg-I210A in mediating LF binding to CHO cells were incubated with PrAg-R200A, PrAg-I210A, and LF. FIG. 4B illustrates data demonstrating LF binding to RAW264.7 cells incubated with various amounts of LF in the presence of PrAg. FIG. 4C illustrates data demonstrating LF binding to RAW264.7 cells incubated with various amounts of LF in the presence of PrAg-R200A combined with PrAg-I210A. FIG. 4D illustrates data demonstrating LF binding to RAW264.7 cells incubated with various amounts of LF in the presence of PrAg-R200A.

FIG. 5 illustrates data demonstrating that intermolecular complementation of two groups of modified PrAg proteins leads to efficient killing of human cancer cells. FIG. 5A illustrates cytotoxicity of a wide range of ratios (from 1:5 to 5:1) of PrAg-U2-R200A and PrAg-L1-R178A, PrAg-U2-R200A and PrAg-L1-I210A, and PrAg-U2-R200A and PrAg-L1-K214A to human melanoma A2058 cells. FIG. 5B illustrates the effects of the protease inhibitors on the cytotoxicity of PrAg proteins to human melanoma A2058 cells pre-incubated with PAI-1 and TIMP-2, then with different PrAg proteins (i.e., PrAg-U2-R200A and PrAg-L1-I210A) as indicated together with FP59. p<0.05, determined by two-tailed Student's t-test.

FIG. 7 illustrates data demonstrating the potent tumoricidal activity of the modified PrAg proteins. Mice were treated with PBS (■), 6 µg PrAg-U2-R200A (▲), 6 µg PrAg-L1-I210A alone (♦), or a combination of 3 µg PrAg-U2-R200A and 3 µg PrAg-L1-I210A (●) in the presence of 0.5 µg FP59 at day 0, 3, and 6.

BRIEF DESCRIPTION OF THE SEQUENCES

Figure 2:
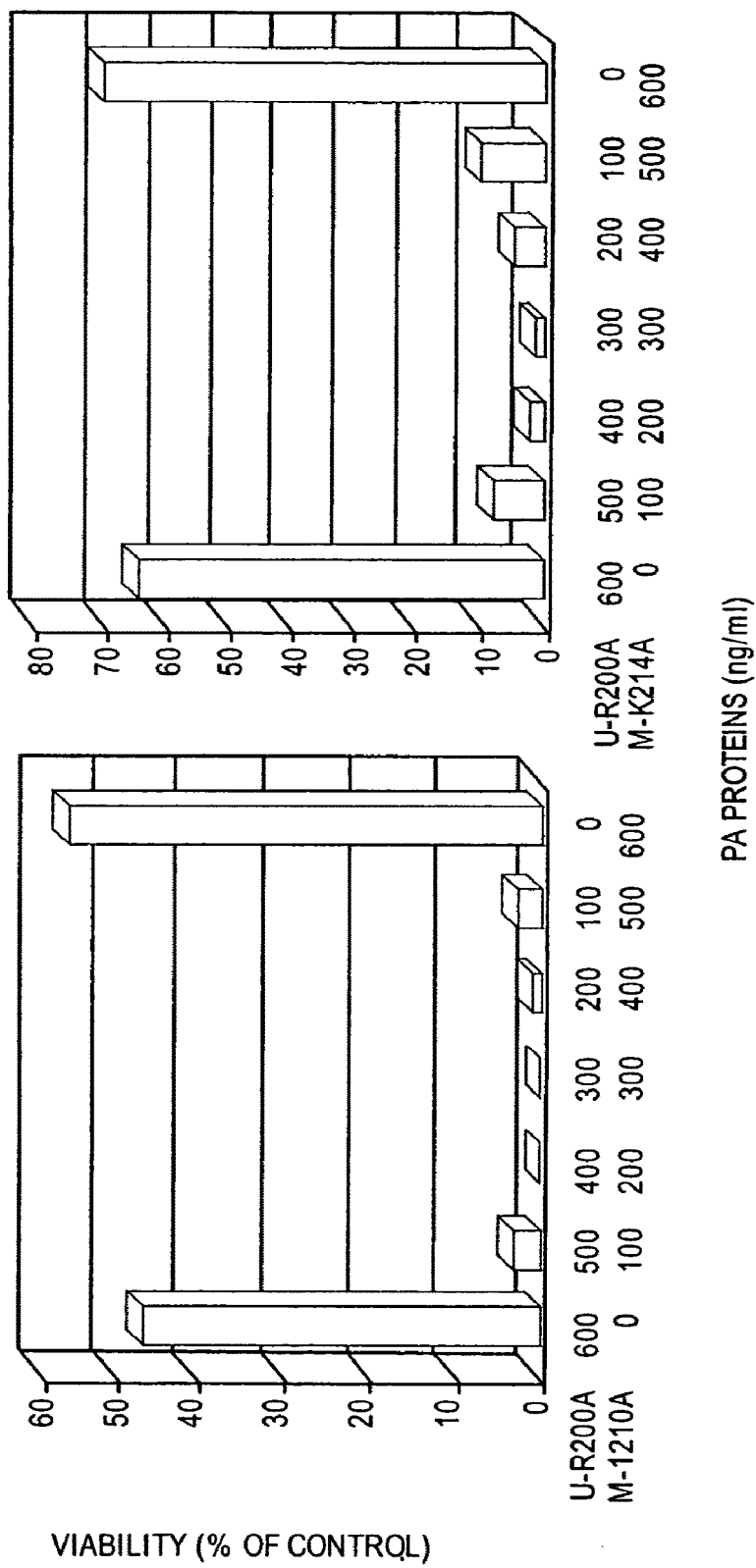
FIG. 2 illustrates data demonstrating the cytotoxicity of two pairs of complementary mutant PrAg proteins to human melanoma A2058 cells. Three mutant PrAg proteins were generated: U-R200A; M-I210A; and M-K214A. U-R200A has the native furin cleavage site of PrAg substituted for a cleavage site for urokinase plasminogen activator and arginine at position 200 substituted for alanine. M-I210A has the native furin cleavage site of PrAg substituted for a cleavage site for matrix metalloproteinase and isoleucine at position 210 substituted for alanine M-K214A has the native furin cleavage site of PrAg substituted for a cleavage site for matrix metalloproteinase and lysine at position 214 substituted for alanine The cells were contacted with various ratios of two mutant PrAg proteins as indicated and with FP59 (i.e., anthrax lethal factor fused to the ADP ribosylation domain of Pseudomonas exotoxin A). Cytotoxicity to tumor cells was demonstrated with a wide range of ratios from 1:5 to 5:1.

SEQ ID NO: 1 is a nucleic acid sequence for the modified PrAg: PrAg-U2-R200A.

SEQ ID NO: 2 is an amino acid sequence for the modified PrAg: PrAg-U2-R200A.

SEQ ID NO: 3 is a nucleic acid sequence for the modified PrAg: PrAg-L1-I210A (i.e., PA-M-I210A).

SEQ ID NO: 4 is an amino acid sequence for the modified PrAg: PrAg-L1-I210A (i.e., PA-M-I210A).

SEQ ID NO: 5 is a nucleic acid sequence for the modified PrAg: PrAg-L1-K214A (i.e., PA-M-K214A).

SEQ ID NO: 6 is an amino acid sequence for the modified PrAg: PrAg-L1-K214A (i.e., PA-M-K214A).

SEQ ID NO: 7 is a nucleic acid sequence for the modified PrAg: PrAg-L1-R178A (i.e., PA-M-R178A).

SEQ ID NO: 8 is an amino acid sequence for the modified PrAg: PrAg-L1-R178A (i.e., PA-M-R178A).

SEQ ID NO: 9 is a nucleic acid sequence for the modified PrAg: PrAg-U2K197A (i.e., PA-U-K197A).

SEQ ID NO: 10 is an amino acid sequence for the modified PrAg: PrAg-U2-K197A (i.e., PA-U-K197A).

SEQ ID NO: 11 is a nucleic acid sequence for wild-type PrAg.

SEQ ID NO: 12 is an amino acid sequence for wild-type PrAg.

SEQ ID NO: 13 is a nucleic acid sequence for the modified PrAg: PrAg-U2.

SEQ ID NO: 14 is an amino acid sequence for the modified PrAg: PrAg-U2.

SEQ ID NO: 15 is a nucleic acid sequence for the modified PrAg: PrAg-R200A.

SEQ ID NO: 16 is an amino acid sequence for the modified PrAg: PrAg-R200A.

SEQ ID NO: 17 is a nucleic acid sequence for the modified PrAg: PrAg-L1.

SEQ ID NO: 18 is an amino acid sequence for the modified PrAg: PrAg-L1.

SEQ ID NO: 19 is a nucleic acid sequence for the modified PrAg: PrAg-I210A

SEQ ID NO: 20 is an amino acid sequence for the modified PrAg: PrAg-I210A

DETAILED DESCRIPTION OF THE INVENTION

I. Introduction

The present invention is provides compositions comprising modified bacterial toxins and methods of using the modified bacterial toxins to specifically target a particular cell population, e.g., a cell population with more than one characteristic. More particularly, the invention is based on modification of the monomer subunits that make up a first effector component (e.g., protective antigen from anthrax toxin) of a multimeric bacterial protein toxin (e.g., anthrax toxin). The monomers are modified in two or more of the following ways: (a) substitution of a native cell-recognition domain for a non-native cell-recognition domain; (b) substitution of a native proteolytic activation site for a non-native proteolytic activation site; (c) modification of said first monomer to generate a first modified monomer, whereby said first modified monomer can pair only with said second monomer; or (d) modification of said first monomer and said second monomer, whereby a second effector component can bind only at a site formed by the interaction of said first monomer and said second monomer molecule. Each modified monomer targets the modified bacterial protein toxin to a target cell with a particular identifying characteristic. A modified effector component of a bacterial protein toxin comprising two different modified monomers (i.e., a hetero-oligomeric effector component) specifically targets a cell with two particular identifying characteristics.

In an exemplary embodiment, the invention provides a modified anthrax protective antigen (i.e., PrAg, or PA). The modified PrAg comprises at least one PrAg monomer in which the native furin cleavage site been replaced with a cleavage site for matrix metalloproteinase and at least one PrAg monomer in which the native furin cleavage site has been replaced with a cleavage site for a plasminogen activator. The PrAg monomers are further modified by mutation of the native LF binding site such that at least two modified PrAg monomers are required to bind LF. These modified PrAg specifically targets cells expressing both MMP and plasminogen activators and have reduced toxicity relative to unmodified PrAg.

II. Definitions

"Bacterial protein toxins" or "bacterial toxins" as used herein refers to any toxin produced by a bacteria. Bacterial protein toxins may be wild-type proteins or may be recombinant proteins. Bacterial protein toxins include multimeric bacterial toxins (i.e., toxins comprising components that are made up of monomers). Multimeric bacterial toxins include multimeric pore-forming bacterial toxins which lack a separate catalytic effector component, as well as multimeric binary bacterial toxins which comprise a cell binding effector component and a separate catalytic effector component. Pore-forming bacterial toxins exert their toxic effect when their monomeric subunits bind to the surface of a target cell and oligomerize to form a transmembrane channel (i.e., pore) in the target cells, thus leading to influx and efflux of small molecules and ions and subsequent swelling and death of the target cell, i.e., by osmotic lysis. Binary bacterial toxins exert their toxic effects when their cell binding effector component binds to target cells and to the separate catalytic effector component, thus targeting the catalytic effector component to the target cells. In some cases, binding of the separate catalytic effector component to the cell binding effector component leads to internalization of the catalytic effector component into the target cell where the catalytic effector component exerts its biological effects (e.g., cell killing or inhibition of cell proliferation). Multimeric pore-forming bacterial toxins which lack a separate catalytic effector component include, e.g., Staphylococcal α-hemolysin, Staphylococcal leukocidin (see, e.g., Miles et al., *Protein Science* 11:894 (2002)), aerolysin (e.g., from *Aeromonas hydrophila*), *Clostridium septicum* α toxin, *Bacillus cereus* hemolysis II, and *Helicobacter pylori* vacuolating toxin (VacA). Multimeric binary toxins which comprise a separate catalytic effector component include, e.g., anthrax toxin, pertussis toxins, cholera toxin, *E. coli* heat-labile enterotoxin, Shiga toxin, pertussis toxin, *Clostridium perfringens* iota toxin, *Clostridium spiroforme* toxin, *Clostridium difficile* binary toxin, *Clostridium botulinum* C2 toxin, and *Bacillus cereus* vegetative insecticidal protein. Anthrax toxin lethal factor (LF), pertussis toxin S1 subunit, cholera toxin subunit A, Shiga toxin subunit A, iota toxin component 1a (an ADP-ribosyltranferase), *Clostridium difficile* toxin subunit A, and *Clostridium botulinum* C2 subunit A serve as the catalytic effector component of their respective toxins (see, e.g.,. Kaslow and Burns, *FASEB J.* 6(9):2684-90 (1992); Paton and Paton, *Clin. Microbiol. Rev.* 11(3):450-479 (1998); m Richard et al., *Int. Microbiol.* (3):185-94 (1999); Lindsay, *Crit. Rev. Microbiol.* 22(4):257-77 (1996); Aktories, *Mol. Cell. Biochem.* 138(1-2):167-76 (1994); and Aktories and Wegner, *Mol. Microbiol.* 6(20):2905-8 (1992)).

Anthrax toxin is a protein toxin produced by *Bacillus anthracis* and comprises three components: the protective antigen (PrAg, 83 kDa; Genbank Accession Nos.: AF268967; (SEQ ID NO:43); AAD32414; (SEQ ID NO:12); NP_052806; (SEQ ID NO:12); and AAF86457 (SEQ ID NO:43)), lethal factor (LF, 90 kDa; Genbank Accession Nos.: AF065404 (SEQ ID NO:44); NC_001496 (SEQ ID NO:44); AAD32411 (SEQ ID NO:44)and JQ0032(SEQ ID NO:44); 1J7NB (chain B); and 1J7NA (chain A)) and edema factor (EF, 89 kDa; Genbank Accession Nos.: AF065404(SEQ ID NO:45); NC_001496(SEQ ID NO:45)); 1K93F (Chain F); 1K93E (Chain E); 1K93D (Chain D); 1K93C (Chain C); 1K93B (Chain B); 1K93A (Chain A); 1K90F (Chain F); 1K90C (Chain C); 1K90E (Chain E); 1K90B (Chain B);

1K90D (Chain D); 1K90A (Chain A); 1K8TA (Chain A)) each of which are individually non-toxic (see, e.g., Liu et al., *Expert Opin. Biol. Then.* 3(5):843-853 (2003). The PrAg is a cell binding effector component which binds to a cell surface receptor for PrAg, while LF and EF are catalytic effector molecules. PrAg is cleaved at the sequence $RKKR_{167}$ (SEQ ID NO:26)by cell-surface furin or furin-like proteases into two fragments: PrAg63, a 63 kDa monomer, which remains receptor-bound and forms a homo-oligomeric heptamer (i.e., a first effector component); and PrAg20, a 20 kDa N-terminal fragment, which is released into the medium (see, e.g., Klimpel et al., *PNAS USA,* 89:10277-10281 (1992); Molloy, et al., *J. B. Chem.,* 267:16396-16402 (1992); Klimpel et al., *Mol. Microbiol.,* 13:1094-1100 (1994); Milne et al., *J. Biol. Chem.,* 269:20607-20612 (1994); and Benson et al., *Biochemistry,* 37:3941-3948 (1998)). The PrAg63 homo-oligomeric heptamer (i.e., the cell binding effector component or a first effector component) binds LF or EF (e.g., the catalytic effector components or the second effector components) and the resulting complex is internalized in a target cell where the LF or EF exert their toxic effects (Leppla, et al., *Bacterial protein toxins,* p. 111-112 (1988) and Gordon et al., *Infect. Immun.,* 56:1066-1069 (1988)).

"Monomer" as used herein refers to a subunit of a effector component (e.g., a cell binding effector component or a catalytic effector component) from a multimeric bacterial protein toxin. The effector components described herein may comprise, for example, at least 2, 3, 4, 5, 6, 7, or 8 monomers. The monomers that make up an effector component may be the same or different. The monomers may comprise the following components: (1) a cell recognition site (i.e., domain) which binds to a molecule on the surface of a target cell; (2) a proteolytic activation site; (3) a monomer binding site; and (4) a binding site for a second effector component. Each of the sites may be a native site or may be a modified (i.e., non-native) site. For example, native anthrax PrAg comprises a cell recognition site that binds a PrAg receptor binding site on the surface of a target cell; a furin cleavage site, a binding site for other PrAg monomers, and anthrax LF and EF binding sites (i.e., binding sites for a second effector molecule). Each of these sites in the native anthrax PrAg can be modified as described herein.

"Effector component" as used herein refers to a cell binding effector component (i.e., a first effector component) and/ or a catalytic effector component (i.e., a second effector component) of the bacterial protein toxins described herein. A "cell binding effector component" binds to a target molecule on a target cell, as well as to a catalytic effector component. Cell binding effector components may comprise at least one, two, three, four, five, six, seven, eight, or more monomers (e.g., anthrax PrAg monomers). Cell binding effector components may be homo-oligomeric (i.e., comprise identical monomers) or hetero-oligomeric (i.e., comprise at least two, three, four, five, six, seven, eight, or more different types of monomers). In some cases, two, three, four, five, six, seven, eight, or more monomers of a cell binding effector component are required to bind to a catalytic effector component. A "catalytic effector component" bound by a cell binding effector component is internalized and exerts a biological activity (e g., inhibition of target cell proliferation and/or target cell killing). Cell binding effector components include, e.g., anthrax protective antigen. Catalytic effector components include, e.g., anthrax lethal factor, anthrax edema factor, truncated anthrax lethal factor (e.g., LFn or amino acids 1-254 of anthrax lethal factor), and FP59 (LFn fused to the ADP-ribosylation domain of Pseudomonas exotoxin A as described in, e.g., Arora et al., *J. Biol. Chem.* 268:3334-3341 (1993) and WO 01/21656). Effector components (i.e., first and second effector components such as cell binding effector components and catalytic effector components) can be modified, e.g., by modification of their monomer subunits as described herein, by fusion to each other, or by fusion of one or more monomers to a heterologous polypeptide (e.g., an antibody, a cytokine, or a cell surface receptor ligand). For example, native anthrax PrAg monomers can be modified such that they no longer bind to the PrAg receptors, but bind to other cell surface molecules (e.g., receptors for cytokines). Native PrAg monomers may also be modified such that they bind to the PrAg receptors in addition to other cell surface molecules including, for example, cell surface receptors specific for ligands other than PrAg (e.g., EGF, IL-2, or GM-CSF). Native PrAg monomers may also be modified so that they bind to a second effector component (e.g., LF or EF, or a biologically active fragment thereof).

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein or polypeptide indicates that the protein or polypeptide comprises two or more subsequences that are not found in the same relationship to each other in nature (e.g., a fusion protein such as the amino acids 1-254 of anthrax lethal factor fused to *Pseudomonas* exotoxin A).

"Cell-recognition domain" as used herein refers to a portion of a monomer that specifically recognizes a cell surface molecule (e.g., a receptor, a ligand, or a protease) on a target cell. The cell-recognition domain may also participate in binding of the monomer to the cell surface molecule. For example, anthrax PrAg monomers comprise a cell recognition domain that recognizes and binds to a PrAg receptor on the surface of target cells. The cell recognition domain may be a native cell recognition domain, a modified cell recognition domain, or may be a heterologous polypeptide that (e.g., an antibody, a cytokine, or cell surface receptor ligand) fused to the monomer. A cell recognition domain that is a heterologous polypeptide also recognizes and/or binds to a cell surface molecule on a target cell. Suitable antibodies include, for example, antibodies that specifically bind to growth factor receptors such as IGR62 as described in, e.g., Modjtahedi et al., *Int. J. Cancer* 105(2):273-80 (2003). Suitable cytokines include, for example, cytokines that are overexpressed on the surface of cancer cells or virally infected cells (e.g., IL-2, GM-CSF, and EGF).

"Proteolytic activation site" as used herein refers to a protease cleavage site of a monomer. Proteolytic activation sites include cleavage sites for any protease known in the art including, for example, plasminogen activators (uPA and tPA), matrix metalloproteinases, (e.g., MMP-1; MMP-2; MMP-3; MMP-7; MMP-8; MMP-9; MMP-10; MMP-11; MMP-12; MMP-13; MMP-14; MMP-15; MMP-16; MMP-17; MMP-19; MMP-20; MMP-21; MMP-23A; MMP-23B; MMP-24; MMP-25; MMP-26; MMP-27; MMP-28; and MT2-MMP); metalloproteases (e.g., Meprin a; Meprin b; Decysin; ADAM1a; ADAM2; ADAM3B; ADAM4; ADAM4B; ADAMS5; ADAM6; ADAM7; ADAM8; ADAM9; ADAM10; ADAM11; ADAM12; ADAM15; ADAM17; ADAM18; ADAM19; ADAM20; ADAM21; ADAM22; ADAM23; ADAM28; ADAM29; ADAM30; ADAM32; ADAM33; ADAMTS1; ADAMTS2; ADAMTS3; ADAMTS4; ADAMTS5/11; ADAMTS6; ADAMTS7;

ADAMTS8; ADAMTS9; ADAMTS10; ADAMTS12; ADAMTS13; ADAMTS14; ADAMTS15; ADAMTS16; ADAMTS17; ADAMTS18; ADAMTS19; ADAMTS20); serine proteases (e.g., Kallikrein hK1; Kallikrein hK2; Kallikrein hK3/PSA; Kallikrein hK4; Kallikrein hK5; Kallikrein hK6; Kallikrein hK7; Kallikrein hK8; Kallikrein hK9; Kallikrein hK10; Kallikrein hK11; Kallikrein hK12; Kallikrein hK13; Kallikrein hK14; Kallikrein hK15; Thrombin; Coagulation factor VIIa; Coagulation factor IXa; Coagulation factor Xa; Coagulation factor XIa; Coagulation factor XIIa; Protein C; Protein Z; Mastin; Tryptase-α1; Tryptase-α2; Tryptase-β1; Tryptase-δ1; Tryptase-γ1; Marapsin; Marapsin-2; Testisin; Brain serine protease-2; Prostasin; Prostasin-like 1; Prostasin-like 2; Chymase; Cathepsin G; Neutrophil elastase; Azurocidin; Hepsin; HAT-related protease; HAT (Human Airway Trypsin-like Protease); Type I transmembrane serine proteases, type II transmembrane serine proteases, cysteine proteases, aspartic acid proteases, HAT-like 1; HAT-like 2; HAT-like 3; HAT-like 4; HAT-like 5; DESC1; Corin; Matriptase; Matriptase-2; Matriptase-3; TMPRSS3; TMPRSS4; Spinesin; Polyserase; MSPL; Neurotrypsin; Urokinase plasminogen activator; Tissue plasminogen activator; Plasminogen; Acrosin; Plasma-kallikrein-like 1; Plasma-kallikrein-like 2; Plasma-kallikrein-like 3; Plasma-kallikrein-like 4; and Seprase); and aspartic proteases (e.g., Cathepsin D; and Cathepsin E); Cysteine Proteases (e.g., Cathepsin B; Cathepsin C; Cathepsin F; Cathepsin H; Cathepsin K; Cathepsin L; Cathepsin L2; Cathepsin S; Cathepsin W; Cathepsin Z and Cathepsin J). Additional suitable protease are described in, e.g., Puente, et al., *Nature Reviews Genetics* 4:544-558 (2003) and website merops.sanger.ac.uk). In exemplary embodiments, the first effector component may comprise monomers with a cleavage site for uPA and/or a cleavage site for MMP; a cleavage site for uPA and/or a cleavage site for Kallikrein hK3/PSA; a cleavage site for uPA and/or a cleavage site for Kallikrein hK2; a cleavage site for Kallikrein hK3/PSA and/or a cleavage site for Kallikrein hK2; a cleavage site for uPA and/or a cleavage site for Hepsin; a cleavage site for Kallikrein hK3/PSA and/or a cleavage site for Hepsin; or a cleavage site for Kallikrein hK2 and/or a cleavage site for Hepsin. Many of these protease or combinations thereof are overexpressed on the surface of diseased cells, e.g., cancer cells, virally infected cells, or cells affected by an autoimmune disease. As described in WO 01/21656, many of these proteases play a role in tumor invasion and metastasis formation. The proteases may also participate in tumor neoangiogenesis and may be selectively upregulated in proliferating tumor cells.

"Monomer binding site" or "oligomerization site" as used herein refers to a portion of a monomer which pairs with (i.e., interacts with/and or binds to and/or complements) other monomers of the same type or monomers of a different type. The monomer binding site of a particular monomer can be modified such that the monomer can pair only with a monomer of a different type. The monomer of a different type may also be modified so that the two monomers are complementary (i.e., can pair only with each other). Monomer binding sites can be modified such that the monomer can pair with two different types of monomers. In some cases each of the two different types of monomers have their respective monomer binding sites modified as well.

Cholera toxin (CT) is a bacterial toxin secreted by *Vibrio cholerae* and comprising A and B subunits. The A subunit is the effector molecule and contributes to intracellular toxicity and the B subunit is required for binding of CT to a cell surface receptor. The structural genes encoding A and B subunits are designated as ctxA and ctxB respectively. (see, e.g., Kaper and Srivastava, *Indian J. Med. Res.*95:163-7 (1992); Field, *Am. J. Clin. Nutr.* (1):189-96 (1979); and Van Heyningen et al., *Ciba Found Symp.* 1976; (42):73-88 (1976)

Shiga toxin is bacterial toxin produced by *Shigella dysenteriae* and comprising A and B subunits. The A subunit is the catalytic effector molecule and has N-glycosidase activity. The B subunit is the cell binding molecule (i.e., first effector component) and binds to a membrane glycolipid, globotriaosylceramide (Gb3). (see, e.g., Nakao and Takeda , *J. Nat. Toxins* (3):299-313 (2000)).

Pertussis toxin is a protein toxin produced by *Bordetella pertussis* and comprises an A protomer and a B oligomer. The A protomer is the catalytic effector molecule and comprises the S1 subunit, which disrupts transmembrane signaling by ADP-ribosylating eukaryotic G-proteins. The B oligomer is the cell binding molecule (i.e., first effector component) and contains five polypeptide monomers, binds to cell receptors and delivers the S1 subunit. Expression of ADP-ribosyltransferase activity in target eukaryotic cells arises after : (1) nucleotides and membrane lipids allosterically promote the release of the S1 subunit; and (2) the single disulfide bond in the Si subunit is reduced by reductants such as glutathione. (see, e.g., Kaslow and Burns, *FASEB J.* 6(9):2684-90 (1992)).

III. Modified Bacterial Toxins

In one embodiment, the present invention provides modified multimeric bacterial toxins. The modified bacterial toxins comprise a first effector component comprising at least 2, 3, 4, 5, 6, 7, or 8 or more monomers. The monomers comprise (1) a cell recognition site (i.e., domain) which binds to a molecule on the surface of a target cell; (2) a proteolytic activation site; (3) a monomer binding site; and (4) a binding site for a second effector component. The monomers of the invention comprise two or more of the following modifications: (a) substitution of a native cell-recognition domain for a non-native cell-recognition domain; (b) substitution of a native proteolytic activation site for a non-native proteolytic activation site; (c) modification of said first monomer to generate a first modified monomer, whereby said first modified monomer can pair only with said second monomer; or (d) modification of said first monomer and said second monomer, whereby a second effector component can bind only at a site formed by the interaction of said first monomer and said second monomer molecule. The second effector component is typically a catalytic effector component that binds to the first effector component, is internalized by the target cell, and exerts a biological effect on the target cell (e g., inhibition of proliferation or killing).

Bacterial protein toxins that can be modified according to the methods of the invention include, for example, toxins with multimeric binding subunits including, for example, pore-forming toxins which lack a catalytic effector component, and binary toxins which comprise a catalytic effector component. Suitable pore-forming toxins which lack a second catalytic effector domain include, for example staphylococcal α-hemolysin, staphylococcal leukocidin, aerolysin (e.g., from *Aeromonas hydrophile*),*Clostridium septicum* α toxin, *Bacillus cereus* hemolysis II, and *Helicobacter pylori* vacuolating toxin (VacA). Suitable binary toxins which comprise catalytic effector domain include, for example, anthrax toxin, cholera toxin, *E. coli* heat-labile enterotoxin, Shiga toxin, pertussis toxin, *Clostridium perfringens*, iota toxin, *Clostridium spiroforme* toxin, *Clostridium difficile* binary toxin, *Clostridium botulinum* C2 toxin, and *Bacillus cereus* vegetative insecticidal protein.

In an exemplary embodiment, modified bacterial protein toxins comprise modified anthrax PrAg monomers in which (1) the native PrAg receptor recognition domain has been replaced by a non-native recognition domain; (2) the naturally occurring furin cleavage site has been replaced by a cleavage site for a different protease (e.g., a metalloproteinase, a cysteine protease, an aspartic acid protease, a plasminogen activator, a kallikrein, a type 1 transmembrane serine protease, a type 2 transmembrane serine protease, or a GPI anchored serine protease); (3) the native monomer binding site (i.e., oligomerization site) has been mutated such that each monomer can only pair with a monomer of a different type; and/or (4) the native lethal factor binding site has been mutated such that at least two different anthrax protective antigen monomers are required to bind lethal factor.

In a preferred embodiment, the present invention provides a modified PrAg molecule comprising at least two types of monomers. The PrAg monomers are modified such that the native furin cleavage site (i.e., RKKR;(SEQ ID NO:26) has been substituted with a cleavage site for a metalloproteinase (e.g., a MMP cleavage site such as GPLGMLSQ; (SEQ ID NO:21) or plasminogen activator (e.g., PGSGRSA; (SEQ ID NO:23); and the lethal factor binding site has been modified such that two complementary modified PrAg monomers must hetero-oligomerize to form a functional anthrax LF binding site (e.g., arginine at position 200 has been substituted by alanine; leucine at position 210 has been substituted by alanine; or lysine at position 214 has been substituted by alanine) The modified hetero-oligomeric PrAg molecule specifically targets cells overexpressing both matrix metalloproteinase and plasminogen activator and has reduced toxicity for non-target cells.

A. Substitution of a Native Cell-Recognition Domain for a Non-Native Cell-Recognition Domain The monomers of the invention may be modified by substitution of their native cell recognition domain for a non-native cell recognition domain. The non-native cell recognition domain recognizes and/or binds to a molecule on the surface of a target cell population (e.g., a cancer cell or a virally infected cell), thus specifically targeting the modified bacterial protein toxin comprising the monomers to the target cells. In some embodiments, the first effector component of the modified bacterial protein toxin comprises two or more types of monomers, each of which has been modified so that the native cell recognition domain for each type of monomer is substituted for a different non-native cell recognition domain. Modified bacterial toxin proteins comprising two or more different types of monomers specifically target cell populations that express all of the molecules recognized and bound by the non-native cell recognition domains. Replacement of a native cell recognition domain may comprise, e.g., replacement of the native cell recognition domain with a recognition domain for another cell surface molecule (e.g., an antibody, a cytokine receptor, or another cell receptor ligand). In some embodiments replacement of the native cell recognition domain comprises fusion of the monomer to a heterologous peptide such as a cytokine, an antibody, or a cell receptor ligand). Exemplary non-native cell recognition domains include, e.g., an antibody, a cytokine, or a cell surface receptor ligand.

Suitable heterologous polypeptides include, for example, VEGF, C-CSF, GM-CSF, EPO, EGF, IL-1, IL-2, IL-4, IL-5, IL-6, interferon α, interferon γ, growth hormone, prolactin, thrombopoietin, or TGF-β. In some embodiments, the heterologous polypeptide comprises an antibody, e.g., an antibody that specifically binds proteins overexpressed on cancer cells such as, for example, Her2/Neu, CD25, CD30, CA19-9, CA-125, VEGF receptors, C-CSF receptors, GM-CSF receptors, EPO receptors, EGF receptors, interluekin receptors (e.g., IL-1R, IL-2R, IL-4R, IL-5R, or IL-6R), interferon receptors (e.g., interferon α or interferon γ), growth hormone receptors, prolactin receptors, thrombopoietin receptors, or TGF-β receptors, and immunoglobulins; an antibody that specifically binds proteins overexpressed on virally infected cells such as, for example, gag, pol, or env proteins, HIV proteases, and reverse transcriptase. In some embodiments, the heterologous polypeptide comprises an antibody that specifically binds proteins overexpressed in a HIV-infected cell, a CMV-infected cell, a HPV-infected cell, a HBV-infected cell, a HCV-infected cell, a HSV-infected cell, and a HZV-infected cell.—In other embodiments, the heterologous polypeptide comprises an antibody that specifically binds proteins overexpressed on cells affected by autoimmune diseases such as, for example, rheumatoid arthritis (RA), diabetes mellitus (DM), myasthenia gravis (MG), systemic lupus erythematosus (SLE), Grave's disease, and Addison's disease.

In an exemplary embodiment, native anthrax PrAg monomers are modified so that their PrAg receptor recognition and binding domain is replaced with a recognition and binding domain for a different molecule on the surface of a target cell. Native PrAg monomers can be modified such that they no longer bind to the PrAg receptors, but bind to other cell surface molecules (e.g., receptors for cytokines). Native PrAg monomers may also be modified such that they binds to the PrAg receptors in addition to other cell surface molecules including, for example, cell surface receptors specific for ligands other than PrAg (e.g., EGF, IL-2, or GM-CSF).

B. Substitution of a Native Proteolytic Activation Site for a Non-Native Proteolytic Activation Site The monomers of the invention may also be modified by substitution of the native proteolytic cleavage sites have been substituted for nonnative proteolytic cleavage sites. Thus, the first effector components comprising the monomers can be activated by cleavage by proteases present on the surface of specific target cell types (e.g., cancer cells, virally infected cells, or cells affected by autoimmune disease). In some embodiment, the first effector components comprises two or more different types of monomers that contain two or more different non-native proteolytic activation sites. Modified bacterial protein toxins comprising such monomers are activated by cleavage of two or more different types of proteases, and thus can conveniently be used to specifically target cells that express two or more different types of proteases.

Proteolytic cleavage site that can be substituted for native cleavage sites include cleavage sites for any proteases known in the art including, e.g., metalloproteinase, a cysteine protease, an aspartic acid protease, a plasminogen activator, a kallikrein, a type 1 transmembrane serine protease, a type 2 transmembrane serine protease, or a GPI anchored serine protease. Additional proteases include, e.g., plasminogen activators (uPA and tPA), matrix metalloproteinases, (e.g., MMP-1; MMP-2; MMP-3; MMP-7; MMP-8; MMP-9; MMP-10; MMP-11; MMP-12; MMP-13; MMP-14; MMP-15; MMP-16; MMP-17; MMP-19; MMP-20; MMP-21; MMP-23A; MMP-23B; MMP-24; MMP-25; MMP-26; MMP-27; MMP-28; and MT2-MMP); metalloproteases (e.g., Meprin a; Meprin b; Decysin; ADAM1a; ADAM2; ADAM3B; ADAM4; ADAM4B; ADAM5; ADAM6; ADAM7; ADAM8; ADAM9; ADAM10; ADAM11; ADAM12; ADAM15; ADAM17; ADAM18; ADAM19; ADAM20; ADAM21; ADAM22; ADAM23; ADAM28; ADAM29; ADAM30; ADAM32; ADAM33; ADAMTS1; ADAMTS2; ADAMTS3; ADAMTS4; ADAMTS5/11; ADAMTS6; ADAMTS7; ADAMTS8; ADAMTS9; ADAMTS10; ADAMTS12; ADAMTS13; ADAMTS14; ADAMTS15; ADAMTS16; ADAMTS17; ADAMTS18;

ADAMTS19; ADAMTS20); serine proteases (e.g., Kallikrein hK1; Kallikrein hK2; Kallikrein hK3/PSA; Kallikrein hK4; Kallikrein hK5; Kallikrein hK6; Kallikrein hK7; Kallikrein hK8; Kallikrein hK9; Kallikrein hK10; Kallikrein hK11; Kallikrein hK12; Kallikrein hK13; Kallikrein hK14; Kallikrein hK15; Thrombin; Coagulation factor VIIa; Coagulation factor IXa; Coagulation factor Xa; Coagulation factor XIa; Coagulation factor XIIa; Protein C; Protein Z; Mastin; Tryptase-α1; Tryptase-α2; Tryptase-β1; Tryptase-δ1; Tryptase-γ1; Marapsin; Marapsin-2; Testisin; Brain serine protease-2; Prostasin; Prostasin-like 1; Prostasin-like 2; Chymase; Cathepsin G; Neutrophil elastase; Azurocidin; Hepsin; HAT-related protease; HAT (Human Airway Trypsin-like Protease); Type I transmembrane serine proteases, type II transmembrane serine proteases, cysteine proteases, aspartic acid proteases, HAT-like 1; HAT-like 2; HAT-like 3; HAT-like 4; HAT-like 5; DESC1; Corin; Matriptase; Matriptase-2; Matriptase-3; TMPRSS3; TMPRSS4; Spinesin; Polyserase; MSPL; Neurotrypsin; Urokinase plasminogen activator; Tissue plasminogen activator; Plasminogen; Acrosin; Plasma-kallikrein-like 1; Plasma-kallikrein-like 2; Plasma-kallikrein-like 3; Plasma-kallikrein-like 4; and Seprase); and aspartic proteases (e.g., Cathepsin D; and Cathepsin E); Cysteine Proteases (e.g., Cathepsin B; Cathepsin C; Cathepsin F; Cathepsin H; Cathepsin K; Cathepsin L; Cathepsin L2; Cathepsin S; Cathepsin W; Cathepsin Z and Cathepsin J). Additional suitable protease are described in, e.g., Puente, et al., *Nature Reviews Genetics* 4:544-558 (2003) and website merops.sanger.ac.uk).

In exemplary embodiments, the first effector component may comprise monomers with a cleavage site for uPA and/or a cleavage site for MMP; a cleavage site for uPA and/or a cleavage site for Kallikrein hK3/PSA; a cleavage site for uPA and/or a cleavage site for Kallikrein hK2; a cleavage site for Kallikrein hK3/PSA and/or a cleavage site for Kallikrein hK2; a cleavage site for uPA and/or a cleavage site for Hepsin; a cleavage site for Kallikrein hK3/PSA and/or a cleavage site for Hepsin; or a cleavage site for Kallikrein hK2 and/or a cleavage site for Hepsin.

In some embodiments, the first effector component comprises modified PrAg monomers in which the native furin cleavage site has been replaced with a matrix metalloproteinase (MMP) cleavage site (e.g., GPLGMLSQ (SEQ ID NO:21) or GPLGLWAQ) (SEQ ID NO:27)), a plasminogen activator cleavage site (e.g., PCPGRVVGG(SEQ ID NO:28), PGSGRSA(SEQ ID NO:23), PGSGKSA(SEQ ID NO:24), or PQRGRSA(SEQ ID NO:29), or a kallikrein cleavage site (e.g., for hK2 as described in, e.g., Mikolajczyk et al., *Eur. J. Biochem.* 246(2):440-6 (1997) and Lövgren et al., *Eur. J. Biochem.* 262, 781-789 (1999); or hK3/PSA as described in, e.g., Brillard-Bourdet et al., *Eur. J. Biochem.* 269, 390-395 (2002)). In some embodiments, the first effector component comprises two or more different modified PrAg monomers, e.g., modified PrAg monomers in which the native furin cleavage site has been replaced with a matrix metalloproteinase (MMP) cleavage site (e.g., GPLGMLSQ (SEQ ID NO:25)or GPLGLWAQ(SEQ ID NO:27)) and modified prAg monomers in which the native furin cleavage site has been replaced with a plasminogen activator cleavage site (e.g., PCPGRVVGG(SEQ ID NO:28), PGSGRSA(SEQ ID NO:23), PGSGKSA(SEQ ID NO:24), or PQRGRSA(SEQ ID NO:29)).

C. Modification of Monomers to Generate Complementary Monomers

The monomers of the invention may be modified so that each monomer can only form hetero-oligomers (i.e., the monomers can pair only with a monomer of a different type). The modified monomers comprise monomer binding sites which have been modified such that the monomer can bind only to a monomer of a different type. In some embodiments, the monomer binding sites have been modified such that the monomer can bind two monomers of two different types. For example, monomer that form a heptameric complex can be modified so that each monomer can bind only to two different, but complementary monomers each of which has their respective monomer binding site modified. For example, a first effector component comprising monomers of type: I, II, III, IV, V, VI, or VII, each of which can bind only to two other monomer types is within the scope of the present invention. In this embodiment, the first effector component a heptamer in which monomer type I can bind only to monomer types II and VII; monomer type II can bind only to monomer types I and III; monomer type III can bind only to monomer types II and IV; monomer type IV can bind only to monomer types III and V; monomer type V can bind only to monomer types IV and VI; monomer type VI can bind only to monomer types V and VII; and monomer type VII can bind only to monomer types VI and I.

In some embodiments, the monomers are modified PrAg monomers in which the native monomer binding site has been mutated such that each monomer can only bind to a monomer of a different type, thus forming a hetero-oligomeric PrAg monomer. One or more of the following substitutions leads to a PrAg monomer that can only form a hetero-oligomeric heptamer: aspartic acid at position 512 for alanine; aspartic acid at position 512 for lysine; lysine at position 199 for glutamic acid; arginine at position 468 for alanine, and arginine at position 470 for aspartic acid. For example, a modified PrAg monomer comprising an alanine at position 512 is unable to homo-oligomerize, but can form functional hetero-oligomers with a modified PrAg with a glutamic acid at position 199, an alanine at position 468, and an aspartic acid at position 470 (see, e.g., Mogridge et al., 2002, supra).

D. Modification of Monomers so that at Least Two Monomers Are Needed to Bind a Second Effector Component The monomers of the invention may also be modified so that at least two monomers are needed to bind a second effector component (e.g., a catalytic effector component) so that it can be delivered to a target cell and exert its biological effect (e.g., target cell killing or inhibition of target cell proliferation). The portion of a first monomer that binds to a second effector molecule is modified so that a second monomer of a different type is required to effectively bind the second effector molecule.

In some embodiments, the present invention provides modified anthrax PrAg monomers in which the native lethal factor binding site has been mutated such that at least two different anthrax protective antigen monomers are required to bind lethal factor. For example, one or more of the following substitutions leads to a PrAg monomer that cannot homo-oligomerize to form a functional LF binding site: arginine at position 178 for alanine; lysine at position 197 for alanine; arginine at position 200 for alanine; isoleucine at position 207 for alanine; isoleucine at position 210 for alanine; lysine at position 214 for alanine As described in the Examples below, modified PrAg monomers comprising alanine at position 200 (R200A), modified PrAg monomers comprising alanine at position 210 (I210A), and modified PrAg monomers comprising alanine and position 214 (K214A) are unable to homo-oligomerize and form a functional PrAg heptamer that binds LF. However the combinations of R200A and I210A or R200A and K214A both form functional PrAg heptamers that bind LF.

E. Second Effector Components

In some embodiments, the modified bacterial protein toxins comprise a second effector component (e.g., a catalytic effector component) which binds to the first effector component and exerts a biological effect (e.g. killing of a target cell or inhibition of target cell proliferation). Suitable second effector components include, e.g., anthrax lethal factor, anthrax edema factor, truncated anthrax lethal factor (e.g., LFn or amino acids 1-254 of anthrax lethal factor), lethal factor fused to a heterologous polyepeptide, FP59 (LFn fused to the ADP-ribosylation domain of *Pseudomonas* exotoxin A as described in, e.g., Arora et al., *J. Biol. Chem.* 268:3334-3341 (1993) and WO 01/21656), the A subunit of cholera toxin, the A subunit of Shiga toxin, and the A protomer of pertussis toxin.

IV. Modified Bacterial Toxin Protein Constructs

In one embodiment, the present invention relates to isolated or purified polynucleotides that encode the modified bacterial protein toxins described herein. In accordance with the invention, any nucleotide sequence which encodes the amino acid sequence of a modified bacterial toxin of interest can be used to generate recombinant molecules which direct the expression of the modified bacterial protein toxin. The modified bacterial protein toxins can be also be chemically fused to a heterologous polypeptide.

Those of skill in the art will recognize a wide variety of ways to introduce mutations into a nucleic acid encoding a modified bacterial toxin or to construct a modified bacterial toxin-encoding nucleic acid. Such methods are well known in the art (see Sambrook et al., *Molecular Cloning, A Laboratory Manual* ($2^{nd}$ ed. 1989); Kriegler, *Gene Transfer and Expression: A Laboratory Manual* (1990); and *Current Protocols in Molecular Biology* (Ausubel et al., eds., 1994)). In some embodiments, nucleic acids of the invention are generated using PCR. For example, using mutagenic PCR modified bacterial toxin encoding nucleic acids can be generated by substituting the nucleic acid subsequence that encodes the furin site with a nucleic acid subsequence that encodes a matrix metalloproteinase (MMP) site (e.g., GPLGMLSQ (SEQ ID NO:21)and GPLGLWAQ(SEQ ID NO:27)). Similarly, a mutagenic PCR method can be used to construct the modified bacterial toxins in which the furin site is replaced by a plasminogen activator cleavage site (e.g., the uPA and tPA physiological substrate sequence PCPGRVVGG (SEQ ID NO:28), the uPA favorite sequence GSGRSA(SEQ ID NO:30), the uPA favorite sequence GSGKSA(SEQ ID NO:31), or the tPA favorite sequence QRGRSA(SEQ ID NO:32)). Mutagenic PCR can be used to construct modified anthrax PrAg monomers which comprise amino acid substitutions as described herein. The amino acid substitutions may comprise substituting the native amino acid residue at any position on the anthrax PrAg for any other amino acid residue, including, for example, alanine, asparagine, aspartic acid, cysteine, glutamic acid, phenylalanin, glycine, histidine, isoleucine, lysine, leucine, methionine, asparagine, proline, glutamine, arginine, serine, threonine, valine, tryptophan, or tyrosine. For example, a mutagenic PCR method can also be used to construct modified anthrax PrAg monomers which comprise one or more of the following substitutions: aspartic acid at position 512 for alanine; aspartic acid at position 512 for lysine; lysine at position 199 for glutamic acid; arginine at position 468 for alanine, and arginine at position 470 for aspartic acid, arginine at position 178 for alanine; lysine at position 197 for alanine; arginine at position 200 for alanine; isoleucine at position 207 for alanine; isoleucine at position 210 for alanine; lysine at position 214 for alanine.

In order to clone full-length coding sequences or homologous variants to generate the modified bacterial toxin polynucleotides, labeled DNA probes designed from any portion of the modified bacterial toxin nucleotide sequences or their complements may be used to screen a genomic library, to identify the coding sequence of each individual component of the modified bacterial toxin.

Such clones may be isolated by screening an appropriate expression library for clones that express a full length modified bacterial toxin (e.g., a modified bacterial toxin comprising at least two protective antigen monomers. The library preparation and screen may generally be performed using methods known to one of ordinary skill in the art, such as methods described in Sambrook et al., Molecular Cloning: A Laboratory Manual, Cold Spring Harbor Laboratories, Cold Spring Harbor, N.Y. (1989). Briefly, a bacteriophage expression library may be plated and transferred to filters. The filters may then be incubated with a detection reagent. In the context of this invention, a "detection reagent" is any compound capable of binding to the modified bacterial toxin, which may then be detected by any of a variety of means known to one of ordinary skill in the art. Typical detection reagents contain a "binding agent," such as Protein A, Protein G, IgG or a lectin, coupled to a reporter group. Preferred reporter groups include enzymes, substrates, cofactors, inhibitors, dyes, radionuclides, luminescent groups, fluorescent groups and biotin. More preferably, the reporter group is horseradish peroxidase, which may be detected by incubation with a substrate such as tetramethylbenzidine or 2,2'-azino-di-3-ethylbenzthiazoline sulfonic acid. Plaques containing genomic or cDNA sequences that express modified bacterial toxins protein are isolated and purified by techniques known to one of ordinary skill in the art. Appropriate methods may be found, for example, in Sambrook et al., supra.

Isolation of coding sequences may also be carried out by the polymerase chain reaction (PCR) using two degenerate oligonucleotide primer pools designed on the basis of the coding sequences disclosed herein. The desired nucleic acids can also be cloned using other well known amplification techniques. Examples of protocols sufficient to direct persons of skill through in vitro amplification methods, including PCR, ligase chain reaction (LCR), Qβ-replicase amplification and other RNA polymerase mediated techniques are found in Sambrook et al., supra, and Ausubel et al. Current Protocols in Molecular Biology (1994), as well as in U.S. Pat. No. 4,683,202; PCR PROTOCOLS A GUIDE TO METHODS AND APPLICATIONS (Innis et al. eds. 1990); Arnheim & Levinson C&EN pp. 36-47 (Oct. 1, 1990); *The Journal of NIH Research* 3:81-94 (1991); Kwoh et al. (1989) *Proc. Natl. Acad. Sci. USA* 86:1173; Guatelli et al. (1990) *Proc. Natl. Acad. Sci. USA* 87:1874; Lomell et al. (1989) *J. Clin. Chem.* 35:1826; Landegren et al. (1988) *Science* 241:1077-1080; Van Brunt (1990) *Biotechnology* 8:291-294; Wu et al. (1989) *Gene* 4:560; and Barringer et al. (1990) *Gene* 89:117. Improved methods of cloning in vitro amplified nucleic acids are described in U.S. Pat. No. 5,426,039. Suitable primers for use in the amplification of the nucleic acids of the invention can be designed based on the sequences provided herein.

In accordance with the invention, a polynucleotide of the invention which encodes a modified bacterial toxin, fragment thereof, or functional equivalent thereof may be used to generate recombinant nucleic acid molecules that direct the expression of the modified bacterial toxin, fragment thereof, or functional equivalent thereof, in appropriate host cells. The modified bacterial toxin products encoded by such polynucleotides may be altered by molecular manipulation of the coding sequence.

Due to the inherent degeneracy of the genetic code, other DNA sequences which encode substantially the same or a functionally equivalent amino acid sequence, may be used in the practice of the invention for the expression of the modified bacterial toxins. Such DNA sequences include those which are capable of hybridizing to the coding sequences or their complements disclosed herein under low, moderate or high stringency conditions as described herein.

Altered nucleotide sequences which may be used in accordance with the invention include deletions, additions or substitutions of different nucleotide residues resulting in a sequence that encodes the same or a functionally equivalent gene product. The gene product itself may contain deletions, additions or substitutions of amino acid residues, which result in a silent change thus producing a functionally equivalent antigenic epitope. Such conservative amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine and tyrosine; and amino acids with nonpolar head groups include alanine, valine, isoleucine, leucine, phenylalanine, proline, methionine and tryptophan.

The nucleotide sequences of the invention may be engineered using standard recombinant DNA techniques which are well known in the art, e.g., site-directed mutagenesis, PCR amplification using degenerate oligonucleotides, exposure of cells containing the nucleic acid to chemical mutagenic agents or radiation, chemical synthesis of a desired oligonucleotide (e.g., in conjunction with ligation and/or cloning to generate large nucleic acids) and other well-known techniques (see, e.g., Giliman et al. (1979) *Gene* 8:81-97; Hutchinson et al. (1978) *J. Biol. Chem.* 253:6551; Roberts et al. (1987) *Nature* 328: 731-734). Preferably, the manipulations do not destroy toxicity of the modified bacterial toxins.

A. Sequence Modifications

Variants of the modified bacterial toxins of the invention that retain the ability to inhibit abnormal cell proliferation may be identified by modifying the sequence in one or more of the aspects described above and assaying the resulting modified bacterial toxin for the ability to bind effector molecules or to form functional hetero-oligomers as described in detail herein. Naturally occurring variants of the individual polypeptide components (i.e., monomers) of the modified bacterial toxin may also be isolated by, for example, screening an appropriate cDNA or genomic library with a DNA sequence encoding each individual polypeptide or a variant thereof.

The above-described sequence modifications may be introduced using standard recombinant techniques or by automated synthesis of the modified bacterial toxin. For example, mutations can be introduced at particular loci by synthesizing oligonucleotides containing a mutant sequence, flanked by restriction sites enabling ligation to fragments of the native sequence. Following ligation, the resulting reconstructed sequence encodes an analogue having the desired amino acid insertion, substitution, or deletion.

Alternatively, oligonucleotide-directed site-specific mutagenesis procedures can be used to provide a gene in which particular codons are altered according to the substitution, deletion, or insertion required. Exemplary methods of making the alterations set forth above are described by Walder et al. (1986) *Gene* 42:133; Bauer et al. (1985) *Gene* 37:73; Craik (1985) *BioTechniques* January:12-19; Smith et al. (1981) GENETIC ENGINEERING: PRINCIPLES AND METHODS, Plenum Press; and U.S. Pat. Nos. 4,518,584 and 4,737,462.

Mutations in nucleotide sequences constructed for expression of such modified bacterial toxins must, of course, preserve the reading frame of the coding sequences and preferably will not create complementary regions that could hybridize to produce secondary mRNA structures, such as loops or hairpins, which would adversely affect the translation of the mRNA. Although a mutation site may be predetermined, it is not necessary that the nature of the mutation per se be predetermined. For example, in order to select for optimum characteristics of mutants at a given site, random mutagenesis may be conducted at the target codon and the expressed modified bacterial toxin screened for the desired activity. Not all mutations in a nucleotide sequence which encodes a modified bacterial toxin will be expressed in the final product. For example, nucleotide substitutions may be made to enhance expression, primarily to avoid secondary structure loops in the transcribed mRNA (see, e.g., European Patent Application 75,444A), or to provide codons that are more readily translated by the selected host, such as the well-known *E. coli* preference codons for *E. coli* expression.

B. Expression of Modified Bacterial Toxins

To obtain high level expression of a nucleic acid (e.g., genomic DNA, PCR product, etc. or combinations thereof) encoding a native modified bacterial toxin (e.g., a modified bacterial toxin comprising anthrax protective antigen) or a modified bacterial toxin (e.g., a modified bacterial toxin comprising U-R200A, M-I210A, or M-K214A), one typically subclones the modified bacterial toxin encoding nucleic acid into an expression vector that contains a strong promoter to direct transcription, a transcription/translation terminator, and if for a nucleic acid encoding a protein, a ribosome binding site for translational initiation. Suitable bacterial promoters are well known in the art and described, e.g., in Sambrook et al. and Ausubel et al. Bacterial expression systems for expressing the modified bacterial toxin encoding nucleic acid are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known in the art and are also commercially available.

In some embodiment, modified bacterial toxin containing proteins are expressed in non-virulent strains of Bacillus using Bacillus expression plasmids containing nucleic acid sequences encoding the particular modified bacterial toxin protein (see, e.g., Singh, Y., et al., *J Biol Chem*, 264:19103-19107 (1989)). The modified bacterial toxin containing proteins can be isolated from the Bacillus culture using protein purification methods (see, e.g., Varughese, M., et al., *Infect Immun*, 67:1860-1865 (1999)).

The promoter used to direct expression of a modified bacterial toxin encoding nucleic acid depends on the particular application. The promoter is preferably positioned about the same distance from the heterologous transcription start site as it is from the transcription start site in its natural setting. As is known in the art, however, some variation in this distance can be accommodated without loss of promoter function. The promoter typically can also include elements that are responsive to transactivation, e.g., Gal4 responsive elements, lac repressor responsive elements, and the like. The promoter can be constitutive or inducible, heterologous or homologous.

In addition to the promoter, the expression vector typically contains a transcription unit or expression cassette that contains all the additional elements required for the expression of the nucleic acid in host cells. A typical expression cassette thus contains a promoter operably linked, e.g., to the nucleic acid sequence encoding the modified bacterial toxin containing protein, and signals required for efficient expression and termination and processing of the transcript, ribosome binding sites, and translation termination. The nucleic acid sequence may typically be linked to a cleavable signal peptide sequence to promote secretion of the encoded protein by the transformed cell. Such signal peptides would include, among others, the signal peptides from bacterial proteins, or mammalian proteins such as tissue plasminogen activator, insulin, and neuron growth factor, and juvenile hormone esterase of *Heliothis virescens*. Additional elements of the cassette may include enhancers.

DNA regions are "operably linked" when they are functionally related to each other. For example, DNA for a signal peptide (secretory leader) is operably linked to DNA for a polypeptide if it is expressed as a precursor which participates in the secretion of the polypeptide; a promoter is "operably linked" to a coding sequence if it controls the transcription of the sequence; or a ribosome binding site is "operably linked" to a coding sequence if it is positioned so as to permit translation. Generally, "operably linked" means contiguous and, in the case of secretory leaders, in reading frame.

In addition to a promoter sequence, the expression cassette should also contain a transcription termination region downstream of the structural gene to provide for efficient termination and processing, if desired. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc.

Expression vectors for bacterial use may comprise a selectable marker and a bacterial origin of replication derived from commercially available plasmids comprising genetic elements of the well known cloning vector pBR322 (ATCC 37017). Such commercial vectors include, e.g., pKK223-3 (Pharmacia Fine Chemicals, Uppsala, Sweden), pGEM1 (Promega Biotec, Madison, Wis.), pET28b (Novagen) and pPDM (a modified pET28b, Corixa). These pBR322 "backbone" sections are combined with an appropriate promoter and the structural sequence to be expressed. *E. coli* is typically transformed using derivatives of pBR322, a plasmid derived from an *E. coli* species (Bolivar et al. (1977) Gene 2:95). pBR322 contains genes for ampicillin and tetracycline resistance and thus provides simple means for identifying transformed cells. Promoters commonly used in recombinant microbial expression vectors include the β-lactamase (penicillinase) and lactose promoter system (Chang et al. (1978) Nature 275:615; and Goeddel et al. (1979) *Nature* 281:544), the tryptophan (trp) promoter system (Goeddel et al. (1980) *Nucl. Acids Res.* 8:4057; and European Patent Application 36,776) and the tac promoter (Maniatis, Molecular Cloning: a Laboratory Manual, Cold Spring Harbor Laboratory, p.412 (1982)). A particularly useful bacterial expression system uses the phage γ PL promoter and cI857ts thermolabile repressor. Plasmid vectors available from the American Type Culture Collection which incorporate derivatives of the γ PL promoter include plasmid pHUB2, resident in *E. coli* strain JMB9 (ATCC 37092) and pPLc28, resident in *E. coli* RR1 (ATCC 53082).

Suitable promoter sequences in yeast vectors include the promoters for alcohol oxidase, metallothionein, 3-phosphoglycerate kinase (Hitzeman et al. (1980) *J. Biol. Chem.* 255: 2073) or other glycolytic enzymes (Hess et al. (1968) *J. Adv. Enzyme Reg.* 7:149; and Holland et al. (1978) *Biochem.* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in, e.g., European Patent Application No. 73,657.

Preferred yeast vectors can be assembled using DNA sequences from pBR322 for selection and replication in *E. coli* (Ampr gene and origin of replication) and yeast DNA sequences including a glucose-repressible ADH2 promoter and α-factor secretion leader. The ADH2 promoter has been described by Russell et al. (1982) *J. Biol. Chem,* 258:2674 and Beier et al. (1982) *Nature* 300:724. The yeast α-factor leader, which directs secretion of heterologous proteins, can be inserted between the promoter and the structural gene to be expressed (see, e.g., Kurjan et al. (1982) *Cell* 30:933; and Bitter et al. (1984) *Proc. Natl. Acad. Sci. USA* 81:5330. The leader sequence may be modified to contain, near its 3' end, one or more useful restriction sites to facilitate fusion of the leader sequence to foreign genes.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification such as thymidine kinase, hygromycin B phosphotransferase, and dihydrofolate reductase. Alternatively, high yield expression systems not involving gene amplification are also suitable, such as using a baculovirus vector in insect cells, with a modified bacterial toxin encoding nucleic acid under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of heterologous sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of protein, which are then purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of calcium phosphate transfection, polybrene, protoplast fusion, electroporation, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

After the expression vector is introduced into the cells, the transfected cells are cultured under conditions favoring expression of the modified bacterial toxin containing protein, which is recovered from the culture using standard techniques identified below.

C. Host Cells

Transformed host cells are cells which have been transformed or transfected with expression vectors constructed using recombinant DNA techniques and which contain sequences encoding modified bacterial toxins of the present invention. Transformed host cells may express the desired modified bacterial toxins, but host cells transformed for purposes of cloning or amplifying modified bacterial toxin DNA do not need to express the modified bacterial toxins. Expressed modified bacterial toxins will preferably be secreted into the culture medium or supernatant, depending on the DNA selected. One skilled in the art will appreciate that if modified bacterial toxins are secreted into the culture supernatant, then they are also soluble in the culture supernatant.

Any of the well known procedures for introducing foreign nucleotide sequences into host cells may be used to introduce the expression vector. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra).

Suitable host cells for expression of recombinant proteins include prokaryotes, yeast or higher eukaryotic cells under the control of appropriate promoters. Examples of suitable mammalian host cell lines include the COS-7 lines of monkey kidney cells, described by Gluzman (1981) *Cell* 23:175, and other cell lines capable of expressing an appropriate vector including, e.g., CV-1/EBNA (ATCC CRL 10478), L cells, C127, 3T3, Chinese hamster ovary (CHO), COS, NS-1, HeLa, Human embryonic Kidney Fibroblasts (HEK 293), BHK and HEK293 cell lines. Mammalian expression vectors may comprise nontranscribed elements (e.g., an origin of replication, a suitable promoter and/or an enhancer linked to the gene to be expressed, and other 5' or 3' flanking nontranscribed sequences) and 5' or 3' nontranslated sequences (e.g., necessary ribosome binding sites, a polyadenylation site, splice donor and acceptor sites, and transcriptional termination sequences). Preferred mammalian expression systems are the Chinese hamster ovary (CHO), the HEK293 and the BHK cell lines. Recombinant CHO-expressed modified bacterial toxin is secreted into the cell supernatant as a glycosylated protein.

Prokaryotes include gram negative or gram positive organisms, for example E. coli (e.g., BL21) or *Bacilli*. Higher eukaryotic cells include established cell lines of insect or mammalian origin as described below. Cell-free translation systems could also be used to produce modified bacterial toxins using RNAs derived from DNA constructs. Appropriate cloning and expression vectors for use with bacterial, fungal, yeast, and mammalian cellular hosts are described, for example, by Pouwels et al., CLONING VECTORS: A LABORATORY MANUAL, Elsevier, N.Y. (1985).

Prokaryotic expression hosts may be used for expression of modified bacterial toxins that do not require extensive proteolytic and disulfide processing. Prokaryotic expression vectors generally comprise one or more phenotypic selectable markers, e.g., a gene encoding a protein conferring antibiotic resistance or supplying an autotrophic requirement, and an origin of replication recognized by the host to ensure amplification within the host. Suitable prokaryotic hosts for transformation include *E. coli* (e.g., BL21 (DE3) CodonPlus *E. coli*), *Bacillus subtilis, Salmonella typhimurium*, and various species within the genera *Pseudomonas, Streptomyces*, and *Staphylococcus*, although other hosts may also be used.

Recombinant modified bacterial toxins may also be expressed in yeast hosts such as *P. pastoris*. Yeast of other genera, such as *Saccharomyces, Schizosaccharomyces* or *Kluyveromyces*, may also be used. Expression in *Pichia* is achieved by ligation of the gene to be expressed into a bacterial shuttle vector (e.g., the pPICZ series from Invitrogen Co.), transformation of the yeast with this vector and chromosomal integration into the alcohol oxidase (AOX) locus of the yeast genome. Selection for recombinant yeast is then performed using, e.g., Zeocin (Invitrogen Co.) and protein expression is induced by the addition of methanol to the growth medium (Higgin et al., "*Pichia* Protocols," METHODS IN MOLECULAR BIOLOGY, Vol. 103, Humana Press (1998)). Suitable strains of *Pichia* for protein expression include, e.g., the SMD1168 *Pichia* strain. Expression systems based on other methodologies, such as the ESP system (Stratagene) may also be used.

Suitable yeast transformation protocols are known to one of skill in the art. An exemplary technique described by Hind et al. (1978) *Proc. Natl. Acad. Sci. USA* 75:1929 involves selecting for Trp+ transformants in a selective medium consisting of 0.67% yeast nitrogen base, 0.5% casamino acids, 2% glucose, 10 mg/ml adenine and 20 mg/ml uracil. Host strains transformed by vectors comprising the ADH2 promoter may be grown for expression in a rich medium consisting of 1% yeast extract, 2% peptone, and 1% glucose supplemented with 80 mg/ml adenine and 80 mg/ml uracil. Derepression of the ADH2 promoter occurs upon exhaustion of medium glucose. Crude yeast supernatants are harvested by filtration and held at 4° C. prior to further purification.

Insect (e.g., Spodoptera or Trichoplusia) cell culture systems can also be used to express recombinant polypeptides. Baculovirus systems for production of heterologous polypeptides in insect cells are reviewed, for example, by Luckow et al. (1988) BioTechnology 6:47.

D. Purification of the Modified Bacterial Toxins of the Invention

Purified modified bacterial toxins may be prepared by culturing suitable host/vector systems to express the recombinant translation products of the DNAs of the present invention, which are then purified from culture media or cell extracts. For example, supernatants from systems which secrete recombinant polypeptides into culture media may be first concentrated using a commercially available protein concentration filter, such as, e.g., an Amicon or Millipore Pellicon ultrafiltration unit. Following the concentration step, the concentrate may be applied to a suitable purification matrix. For example, a suitable affinity matrix may comprise a counter structure protein (i.e., a protein to which a modified bacterial toxin binds in a specific interaction based on structure) or lectin or antibody molecule bound to a suitable support.

Alternatively, an anion exchange resin can be used, for example, a matrix or substrate having pendant diethylaminoethyl (DEAE) groups. The matrices can be acrylamide, agarose, dextran, cellulose, polystyrene, sepharose or other types commonly used in protein purification. Alternatively, a cation exchange step can be used. Suitable cation exchangers include various insoluble matrices comprising sulfopropyl or carboxy-methyl groups, preferably sulfopropyl groups. Gel filtration chromatography also provides a means of purifying modified bacterial toxins. The modified bacterial toxins of the invention are preferably purified by anion exchange chromatography using, e.g., monoQ columns or Q sepharose High Performance chromatography.

Affinity chromatography is another preferred method of purifying modified bacterial toxins. For example, monoclonal antibodies against the modified bacterial toxins may be useful in affinity chromatography purification, by using methods that are well-known in the art.

Finally, one or more reverse-phase high performance liquid chromatography (RP-HPLC) steps using hydrophobic RP-HPLC media (e.g., silica gel having pendant methyl or other aliphatic groups) may be used to further purify modified bacterial toxin compositions. Some or all of the foregoing purification steps, in various combinations, can also be used to provide a homogeneous recombinant protein or polypeptide.

Recombinant modified bacterial toxins produced in bacterial culture may be purified by initial extraction from cell pellets, followed by one or more concentration, salting-out, aqueous ion exchange or size exclusion chromatography steps. High performance liquid chromatography (HPLC) may be used for final purification steps. Microbial cells used in expression of recombinant modified bacterial toxins can be disrupted by any convenient method, including freeze-thaw cycling, sonication, mechanical disruption, or use of cell lysing agents.

Fermentation of yeast cells which express modified bacterial toxins as a secreted protein greatly simplifies purification. The secreted recombinant proteins resulting from a large-scale fermentation can be purified by methods analogous to those disclosed by Urdal et al. (1984) *J. Chromatog.* 296:171. This reference describes two sequential, reverse-phase HPLC steps for purification of recombinant human GM-CSF on a preparative HPLC column.

Preparations of modified bacterial toxins synthesized in recombinant cultures may contain non-modified bacterial toxin cell components, including proteins, in amounts and of a character which depend upon the purification steps taken to recover the modified bacterial toxins from the culture. These components are ordinarily of yeast, prokaryotic or non-human eukaryotic origin. Such preparations are typically free of other proteins which may be normally associated with the modified bacterial toxin protein as it is found in nature in its species of origin.

In general, modified bacterial toxins and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

V. Purification of Modified Bacterial Toxins

Recombinant proteins of the invention can be purified from any suitable expression system, e.g., by expressing the proteins in *B. anthracis* and then purifying the recombinant protein via conventional purification techniques (e.g., ammonium sulfate precipitation, ion exchange chromatography, gel filtration, etc.) and/or affinity purification, e.g., by using antibodies that recognize a specific epitope on the protein or on part of the modified bacterial toxin, or by using glutathione affinity gel, which binds to GST (see, e.g., Scopes, *Protein Purification: Principles and Practice* (1982); U.S. Pat. No. 4,673,641; Ausubel et al., supra; and Sambrook et al., supra). In some embodiments, the recombinant protein is a modified bacterial toxin with GST or Ga14 at the N-terminus. Those of skill in the art will recognize a wide variety of peptides and proteins that can be fused to the modified bacterial toxin containing protein to facilitate purification (e.g., maltose binding protein, a polyhistidine peptide, etc.).

A. Purification of Proteins from Recombinant Bacteria

Recombinant and native proteins can be expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of inclusion bodies. For example, purification of inclusion bodies typically involves the extraction, separation and/or purification of inclusion bodies by disruption of bacterial cells, e.g., by incubation in a buffer of 50 mM Tris/HCl pH 7.5, 50 mM NaCl, 5 mM $MgCl_2$, 1 mM DTT, 0.1 mM ATP, and 1 mM PMSF. The cell suspension can be lysed using 2-3 passages through a French press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. The protein of choice is separated from other bacterial proteins by standard separation techniques, e.g., ion exchange chromatography, ammonium sulfate fractionation, etc.

B. Standard Protein Separation Techniques for Purifying Proteins of the Invention 1. Solubility Fractionation Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. Alternatively, the protein of interest in the supernatant can be further purified using standard protein purification techniques. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

2. Size Differential Filtration

The molecular weight of the protein, e.g., PA-U-R200A, PA-M-I210A, or PA-M-K214A, etc., can be used to isolated the protein from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

3. Column Chromatography

The protein of choice can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

In some embodiments, the proteins are purified from culture supernatants of *Bacillus* or *E. coli*. Briefly, the proteins are purified by making a culture supernatant 5 mM in EDTA, 35% saturated in ammonium sulfate and 1% in phenyl-Sepharose Fast Flow (Pharmacia). The phenyl-Sepharose Fast Flow is then agitated and collected. The collected resin is washed with 35% saturated ammonium sulfate and the modified bacterial toxins were then eluted with 10 mM HEPES-1 mM EDTA (pH 7.5). The proteins can then be further purified using a MonoQ column (Pharmacia Biotech). The proteins can be eluted using a NaCl gradient in 10 mM CHES (2-[N-cyclohexylamino]ethanesulfonic acid)-0.06% (vol/vol) ethanolamine (pH 9.1). The pooled MonoQ fractions can then be dialyzed against the buffer of choice for subsequent analysis or applications.

VI. Chemical Linkage of Modified Bacterial Toxins

Although certain of the methods of the invention have been described as using modified bacterial toxins, it will be understood that other modified bacterial toxin compositions having chemically attached compounds can be used in the methods of the invention. In another embodiment, the portions of the modified bacterial toxin, (e.g., anthrax protective antigen monomers and a cell recognition domain such as a cytokine, an antibody, or a cell receptor ligand) are joined via a linking group. The linking group can be a chemical crosslinking agent, including, for example, succinimidyl-(N-maleimidomethyl)-cyclohexane-1-carboxylate (SMCC). The linking group can also be an additional amino acid sequence(s), including, for example, a polyglycine linking group.

Functional groups capable of forming covalent bonds with the amino- and carboxyl-terminal amino acids or side groups of amino acids are well known to those of skill in the art. For example, functional groups capable of binding the terminal amino group include anhydrides, carbodiimides, acid chlorides, and activated esters. Similarly, functional groups capable of forming covalent linkages with the terminal carboxyl include amines and alcohols. Such functional groups can be used to bind heterologous polypeptides to modified bacterial toxins (e.g., modified bacterial toxins comprising anthrax protective antigen monomers) at either the amino- or carboxyl-terminus. Heterologous polypeptides can also be bound to the modified bacterial toxin through interactions of amino acid residue side groups, such as the SH group of cysteine (see, e.g., Thorpe et al., *Monoclonal Antibody-Toxin Conjugates: Aiming the Magic Bullet*, in *Monoclonal Antibodies in Clinical Medicine*, pp. 168-190 (1982); Waldmann, *Science*, 252: 1657 (1991); U.S. Pat. Nos. 4,545,985 and 4,894,443).

In an exemplary embodiment, the coding sequences of each polypeptide in the modified bacterial toxin are directly joined at their amino- or carboxy-terminus via a peptide bond in any order.

Alternatively, an amino acid linker sequence may be employed to separate the first and second polypeptide components by a distance sufficient to ensure that each polypeptide folds into its secondary and tertiary structures. Such an amino acid linker sequence is incorporated into the modified bacterial toxin using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala, may also be used in the linker sequence. Amino acid sequences which may be usefully employed as linkers include those disclosed in Maratea et al. (1985) *Gene* 40:39-46; Murphy et al. (1986) *Proc. Natl. Acad. Sci. USA* 83:8258-8262; and in U.S. Pat. Nos. 4,935,233 and 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

Other chemical linkers include carbohydrate linkers, lipid linkers, fatty acid linkers, polyether linkers, e.g., PEG, etc. (see, e.g., Hermanson (1996) Bioconjugate Techniques).

VII. Synthesis of Modified Bacterial Toxins

In one embodiment of the invention, the coding sequence of a modified bacterial toxin (e.g., U-R200A; M-I210A; or M-K214A) may be synthesized in whole or in part, using chemical methods well known in the art (see, e.g., Caruthers et al. (1980) *Nuc. Acids Res. Symp. Ser.* 7:215-233; Crea et al. (1980) *Nuc. Acids Res.* 9(10):2331; Matteucci et al. (1980) *Tetrahedron Letter* 21:719 (1980); and Chow et al. (1981) *Nuc. Acids Res.* 9(12):2807-2817).

The modified bacterial toxin polypeptide itself can be produced using chemical methods to synthesize an amino acid sequence in whole or in part. For example, peptides can be synthesized by solid phase techniques such as, e.g., the Merrifield solid phase synthesis method, in which amino acids are sequentially added to a growing chain of amino acids (see, Merrifield (1963) *J. Am. Chem. Soc.* 85:2149-2146). Equipment for automated synthesis of polypeptides is commercially available from suppliers such as Perkin Elmer Biosystems, Inc. (Foster City, Calif.), and may generally be operated according to the manufacturer's instructions. The synthesized peptides can then be cleaved from the resin and purified, e.g., by preparative high performance liquid chromatography (see, Creighton, Proteins Structures and Molecular Principles, pp. 50-60 (1983)). The composition of the synthetic modified bacterial toxins may be confirmed by amino acid analysis or sequencing (e.g., the Edman degradation procedure; see, Creighton, Proteins, Structures and Molecular Principles, pp. 34-49 (1983)).

In addition, nonclassical amino acids or chemical amino acid analogs can be introduced as a substitution or addition into the sequence. Non-classical amino acids include, but are not limited to, the D-isomers of the common amino acids, α-amino isobutyric acid, 4-aminobutyric acid, Abu, 2-amino butyric acid, γ-Abu, ϵ-Ahx, 6-amino hexanoic acid, Aib, 2-amino isobutyric acid, 3-amino propionic acid, ornithine, norleucine, norvaline, hydroxyproline, sarcosine, citrulline, cysteic acid, t-butylglycine, t-butylalanine, phenylglycine, cyclohexylalanine, β-alanine, fluoro-amino acids, designer amino acids such as β-methyl amino acids, Cα-methyl amino acids, Nα-methyl amino acids, and amino acid analogs in general. Furthermore, the amino acid can be D (dextrorotary) or L (levorotary).

VIII. Identification of Functional Modified Bacterial Protein Toxins

The administration of a functional modified bacterial protein toxin of the invention can specifically target and inhibit proliferation of cell that overexpress one or more cell surface molecule including, e.g., a metalloproteinase, a cysteine protease, an aspartic acid protease, a plasminogen activator, a kallikrein, a type 1 transmembrane serine protease, a type 2 transmembrane serine protease, a GPI anchored serine protease, a cytokine receptor. One of skill in the art can readily identify functional modified bacterial protein toxins using methods that are well known in the art. Changes in cell growth can be assessed by using a variety of in vitro and in vivo assays, e.g., MTT assay, ability to grow on soft agar, changes in contact inhibition and density limitation of growth, changes in growth factor or serum dependence, changes in the level of tumor specific markers, changes in invasiveness into Matrigel, changes in cell cycle pattern, changes in tumor growth in vivo, such as in transgenic mice, etc.

The term "over-expressing" refers to a cell that expresses a mRNA or protein (e.g., for a metalloproteinase, a cysteine protease, an aspartic acid protease, a plasminogen activator, a kallikrein, a type 1 transmembrane serine protease, a type 2 transmembrane serine protease, or a GPI anchored serine protease, a growth factor, or a cytokine) in amounts at least about twice that normally produced in a reference normal cell type, e.g., a Vero cell. Overexpression can result, e.g., from selective pressure in culture media, transformation, activation of endogenous genes, or by addition of exogenous genes. Overexpression can be analyzed using a variety of assays known to those of skill in the art to determine if the gene or protein is being overexpressed (e.g., northerns, RT-PCR, westerns, immunoassays, cytotoxicity assays, growth inhibition assays, enzyme assays, gelatin zymography, etc.). An example of a cell overexpressing a matrix metalloproteinase are the tumor cell lines, fibrosarcoma HT1080, melanoma A2058 and breast cancer MDA-MB-231. An example of a cell which does not overexpress a matrix metalloproteinase is the non-tumor cell line Vero. An example of a cells that overexpress a plasminogen activator receptor are the uPAR overexpressing cell types Hela, A2058, and Bowes. An example of a cell which does not overexpress a plasminogen activator receptor is the non-tumor cell line Vero. An example of a cells that overexpress a tissue-type plasminogen activator are cell types human melanoma Bowes and human primary vascular endothelial cells. An example of a cell which does not overexpress a plasminogen activator receptor is the non-tumor cell line Vero. An example of a cell which overexpresses GM-CSF receptors if the human leukemia cell line U397. An example of a cell which does not overexpress GM-CSF receptors is CEM-SS. Each of the aforementioned cell types can be used in assays to identify functional modified bacterial protein toxins.

A. Assays for Changes in Cell Growth by Administration of Modified Bacterial Toxin One or more of the following assays can be used to identify proteins of the invention which are capable of regulating cell proliferation. The phrase "modified bacterial toxin constructs" refers to a modified bacterial toxin of the invention. Functional modified bacterial toxin constructs identified by the following assays can then be used to treat disease and conditions, e.g., to inhibit abnormal cellular proliferation and transformation. Thus, these assays can be sued to identify modified bacterial toxins that are useful to inhibit cell growth of tumors, cancers, cancerous cells, and other pathogenic cell types.

1. Soft Agar Growth or Colony Formation in Suspension

Soft agar growth or colony formation in suspension assays can be used to identify modified bacterial toxin constructs which inhibit abnormal cellular proliferation and transformation. Typically, transformed host cells (e.g., cells that grow on soft agar) are used in this assay. Techniques for soft agar growth or colony formation in suspension assays are described in Freshney, *Culture of Animal Cells a Manual of Basic Technique,* $3^{rd}$ ed., Wiley-Liss, New York (1994), herein incorporated by reference. See also, the methods section of Garkavtsev et al. (1996), supra, herein incorporated by reference.

Normal cells require a solid substrate to attach and grow. When the cells are transformed, they lose this phenotype and grow detached from the substrate. For example, transformed cells can grow in stirred suspension culture or suspended in semi-solid media, such as semi-solid or soft agar. The transformed cells, when transfected with tumor suppressor genes, regenerate normal phenotype and require a solid substrate to attach and grow.

Administration of an active modified bacterial toxin to transformed cells would reduce or eliminate the host cells' ability to grow in stirred suspension culture or suspended in semi-solid media, such as semi-solid or soft. This is because the transformed cells would regenerate anchorage dependence of normal cells, and therefore require a solid substrate to grow. Therefore, this assay can be used to identify modified bacterial toxins that inhibit cell growth. Once identified, such modified bacterial toxin constructs can be used in a number of diagnostic or therapeutic methods, e.g., in cancer therapy to inhibit abnormal cellular proliferation and transformation.

2. Contact Inhibition and Density Limitation of Growth

Contact inhibition and density limitation of growth assays can be used to identify modified bacterial toxin constructs which are capable of inhibiting abnormal proliferation and transformation in host cells. Typically, transformed host cells (e.g., cells that are not contact inhibited) are used in this assay. Administration of a modified bacterial toxin construct to these transformed host cells would result in cells which are contact inhibited and grow to a lower saturation density than the transformed cells. Therefore, this assay can be used to identify modified bacterial toxin constructs which are useful in compositions for inhibiting cell growth. Once identified, modified bacterial toxin constructs can be used in disease therapy to inhibit abnormal cellular proliferation and transformation.

Alternatively, labeling index with [$^3$H]-thymidine at saturation density can be used to measure density limitation of growth. See Freshney (1994), supra. The transformed cells, when treated with a functional modified bacterial toxin, regenerate a normal phenotype and become contact inhibited and would grow to a lower density. In this assay, labeling index with [$^3$H]-thymidine at saturation density is a preferred method of measuring density limitation of growth. Transformed host cells are treated with one or more modified bacterial toxin constructs (e.g., U-R200A; M-I210A; M-K214A; or a combination thereof) and are grown for 24 hours at saturation density in non-limiting medium conditions. The percentage of cells labeling with [$^3$H]-thymidine is determined autoradiographically. See, Freshney (1994), supra. The host cells treated with a functional modified bacterial toxin construct would give arise to a lower labeling index compared to control (e.g., transformed host cells treated with a non-functional modified bacterial toxin).

3. Growth Factor or Serum Dependence

Growth factor or serum dependence can be used as an assay to identify functional modified bacterial toxin constructs. Transformed cells have a lower serum dependence than their normal counterparts (see, e.g., Temin, *J. Natl. Cancer Insti.* 37:167-175 (1966); Eagle et al., *J. Exp. Med.* 131:836-879 (1970)); Freshney, supra. This is in part due to release of various growth factors by the transformed cells. When a tumor suppressor gene is transfected and expressed in these transformed cells, the cells would reacquire serum dependence and would release growth factors at a lower level. Therefore, this assay can be used to identify modified bacterial toxin constructs which are able to inhibit cell growth. Growth factor or serum dependence of transformed host cells which are transfected with a modified bacterial toxin construct can be compared with that of control (e.g., transformed host cells which are treated with a non-functional modified bacterial toxin). Transformed host cells treated with a functional modified bacterial toxin would exhibit an increase in growth factor and serum dependence compared to control.

4. Tumor Specific Markers Levels

Tumor cells release an increased amount of certain factors (hereinafter "tumor specific markers") than their normal counterparts. For example, tumor angiogenesis factor (TAF) is released at a higher level in tumor cells than their normal counterparts. See, e.g., Folkman, Angiogenesis and cancer, *Sem Cancer Biol. (*1992*)*).

Tumor specific markers can be assayed to identify modified bacterial toxin constructs, which, decrease the level of release of these markers from host cells. Typically, transformed or tumorigenic host cells are used. Administration of a modified bacterial toxin to these host cells would reduce or eliminate the release of tumor specific markers from these cells. Therefore, this assay can be used to identify modified bacterial toxin constructs are functional in suppressing tumors.

Various techniques which measure the release of these factors are described in Freshney (1994), supra. Also, see, Unkless et al., *J. Biol. Chem.* 249:4295-4305 (1974); Strickland & Beers, *J. Biol. Chem.* 251:5694-5702 (1976); Whur et al., *Br. J. Cancer* 42:305-312 (1980); Gulino, *Angiogenesis, tumor vascularization, and potential interference with tumor growth*. In Mihich, E. (ed): "Biological Responses in Cancer." New York, Plenum (1985); Freshney Anticancer Res. 5:111-130 (1985).

5. Cytotoxicity Assay with MTT

The cytotoxicity of a particular modified bacterial toxin can also be assayed using the MTT cytotoxicity assay. Cells are seeded and grown to 80 to 100% confluence. The cells are then were washed twice with serum-free DMEM to remove residual FCS and contacted with a particular modified bacterial toxin. MTT (3-[4,5-dimethylthiazol-2-yl]-2,5-diphenyltetrazolium bromide) is then added to the cells and oxidized MTT (indicative of a live cell) is solubilized and quantified.

6. Invasiveness into Matrigel

The degree of invasiveness into Matrigel or some other extracellular matrix constituent can be used as an assay to identify modified bacterial toxin constructs which are capable of inhibiting abnormal cell proliferation and tumor growth. Tumor cells exhibit a good correlation between malignancy and invasiveness of cells into Matrigel or some other extracellular matrix constituent. In this assay, tumorigenic cells are typically used. Administration of an active modified bacterial toxin to these tumorigenic host cells would decrease their invasiveness. Therefore, functional modified bacterial toxin constructs can be identified by measuring changes in the level of invasiveness between the tumorigenic cells before and after the administration of the modified bacterial toxin constructs.

Techniques described in Freshney (1994), supra, can be used. Briefly, the level of invasion of tumorigenic cells can be measured by using filters coated with Matrigel or some other extracellular matrix constituent. Penetration into the gel, or through to the distal side of the filter, is rated as invasiveness, and rated histologically by number of cells and distance moved, or by prelabeling the cells with $^{125}$I and counting the radioactivity on the distal side of the filter or bottom of the dish. See, e.g., Freshney (1984), supra.

7. $G_0/G_1$ Cell Cycle Arrest Analysis $G_0/G_1$ cell cycle arrest can be used as an assay to identify functional modified bacterial toxin construct. Modified bacterial toxin/effector molecule construct administration can cause G1 cell cycle arrest. In this assay, cell lines can be used to screen for functional modified bacterial toxin constructs. Cells are treated with a putative modified bacterial toxin construct. The cells can be transfected with a nucleic acid comprising a marker gene, such as a gene that encodes green fluorescent protein. Administration of a functional modified bacterial toxin would cause $G_0/G_1$ cell cycle arrest. Methods known in the art can be used to measure the degree of $G_1$ cell cycle arrest. For example, the propidium iodide signal can be used as a measure for DNA content to determine cell cycle profiles on a flow cytometer. The percent of the cells in each cell cycle can be calculated. Cells exposed to a functional modified bacterial toxin would exhibit a higher number of cells that are arrested in $G_0/G_1$ phase compared to control (e.g., treated in the absence of a modified bacterial toxin).

8. Tumor Growth in Vivo

Effects of modified bacterial toxins on cell growth can be tested in transgenic or immune-suppressed mice. Transgenic mice can be made, in which a tumor suppressor is disrupted (knock-out mice) or a tumor promoting gene is overexpressed. Such mice can be used to study effects of modified bacterial toxins as a method of inhibiting tumors in vivo.

Knock-out transgenic mice can be made by insertion of a marker gene or other heterologous gene into a tumor suppressor gene site in the mouse genome via homologous recombination. Such mice can also be made by substituting the endogenous tumor suppressor with a mutated version of the tumor suppressor gene, or by mutating the endogenous tumor suppressor, e.g., by exposure to carcinogens.

A DNA construct is introduced into the nuclei of embryonic stem cells. Cells containing the newly engineered genetic lesion are injected into a host mouse embryo, which is re-implanted into a recipient female. Some of these embryos develop into chimeric mice that possess germ cells partially derived from the mutant cell line. Therefore, by breeding the chimeric mice it is possible to obtain a new line of mice containing the introduced genetic lesion (see, e.g., Capecchi et al., *Science* 244:1288 (1989)). Chimeric targeted mice can be derived according to Hogan et al., *Manipulating the Mouse Embryo: A Laboratory Manual*, Cold Spring Harbor Laboratory (1988) and *Teratocarcinomas and Embryonic Stem Cells: A Practical Approach*, Robertson, ed., IRL Press, Washington, D.C., (1987).

These knock-out mice can be used as hosts to test the effects of various modified bacterial toxin constructs on cell growth. These transgenic mice with a tumor suppressor gene knocked out would develop abnormal cell proliferation and tumor growth. They can be used as hosts to test the effects of various modified bacterial toxin constructs on cell growth. For example, introduction of modified bacterial toxin constructs into these knock-out mice would inhibit abnormal cellular proliferation and suppress tumor growth.

Alternatively, various immune-suppressed or immune-deficient host animals can be used. For example, genetically athymic "nude" mouse (see, e.g., Giovanella et al., *J. Natl. Cancer Inst.* 52:921 (1974)), a SCID mouse, a thymectomized mouse, or an irradiated mouse (see, e.g., Bradley et al., *Br. J. Cancer* 38:263 (1978); Selby et al., *Br. J. Cancer* 41:52 (1980)) can be used as a host. Transplantable tumor cells (typically about $10^6$ cells) injected into isogenic hosts will produce invasive tumors in a high proportions of cases, while normal cells of similar origin will not. In hosts which developed invasive tumors, cells are exposed to a modified bacterial toxin (e.g., by subcutaneous injection). After a suitable length of time, preferably 4-8 weeks, tumor growth is measured (e.g., by volume or by its two largest dimensions) and compared to the control. Tumors that have statistically significant reduction (using, e.g., Student's T test) are said to have inhibited growth. Using reduction of tumor size as an assay, functional modified bacterial toxin constructs which are capable of inhibiting abnormal cell proliferation can be identified. This model can also be used to identify functional versions of modified bacterial toxins.

IX. Administration of Modified Bacterial Toxins

Modified bacterial protein toxins of the invention and pharmaceutical compositions comprising such the modified bacterial protein toxins can be administered directly to the patient, e.g., for inhibition of cancer, tumor, or precancer cell growth in vivo; or for inhibition of virally infected cell growth in vivo, or for inhibition of autoimmune disease (i.e., by killing cells affected by autoimmune disease) in vivo. The modified bacterial protein toxins specifically target cells that have more than one identifying characteristic (e.g., overexpress two or more different proteases).

Administration is by any of the routes normally used for introducing a compound into ultimate contact with the tissue (e.g. a cancerous tissue, a virally infected tissue, or a tissue affected by autoimmune disease) to be treated. The compounds are administered in any suitable manner, preferably with pharmaceutically acceptable carriers. Suitable methods of administering such compounds are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences*, $17^{th}$ ed. 1985)). For example, if in vivo delivery of a biologically active modified bacterial toxin protein is desired, the methods described in Schwarze et al. (see *Science* 285:1569-1572 (1999)) can be used.

The compounds, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

The dose administered to a patient ("a therapeutically effective amount"), in the context of the present invention should be sufficient to effect a beneficial therapeutic response in the patient over time. The dose will be determined by the efficacy of the particular compound employed and the condition of the patient, as well as the body weight or surface area of the patient to be treated. The size of the dose also will be determined by the existence, nature, and extent of any adverse side-effects that accompany the administration of a particular compound or vector in a particular patient In determining the effective amount of the compound(s) to be administered in the treatment or prophylaxis of cancer, the physician evaluates circulating plasma levels of the respective compound(s), progression of the disease, and the production of anti-compound antibodies. In general, the dose equivalent of a compound is from about 1 ng/kg to 10 mg/kg for a typical patient. Administration of compounds is well known to those of skill in the art (see, e.g., Bansinath et al., *Neurochem Res.* 18:1063-1066 (1993); Iwasaki et al., *Jpn. J.*

Cancer Res. 88:861-866 (1997); Tabrizi-Rad et al., Br. J. Pharmacol. 111:394-396 (1994)).

For administration, compounds of the present invention can be administered at a rate determined by the LD-50 of the particular compound, and its side-effects at various concentrations, as applied to the mass and overall health of the patient. Administration can be accomplished via single or divided doses.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

EXAMPLES

The following examples are provided by way of illustration only and not by way of limitation. Those of skill in the art will readily recognize a variety of noncritical parameters that could be changed or modified to yield essentially similar results.

Example 1

Materials and Methods

Construction of mutated PrAg proteins: A modified overlap PCR method was used to construct the two groups of mutated PrAg proteins. The group L included two uPA-activated PrAg proteins, PrAg-U2-K197A and PrAg-U2-R200A, in which LF-binding subsite II residues $Lys^{197}$ and $Arg^{200}$ were changed to Ala. The group R contained three MMP-activated PrAg proteins, PrAg-L1-R178A, PrAg-L1-I210A, and PrAg-L1-K214A, in which the LF-binding subsite I ($Arg^{178}$) or subsite III ($Ile^{210}$ and $Lys^{214}$) were changed to Ala. To amplify DNA for the group L mutants, PrAg-U2 expression plasmid pYS5-PrAg-U2 (Liu, S. et al., *J. Biol. Chem.* 276, 17976-17984 (2001)) was used as a template. We used a sense primer Pn (GGTAGATGACCAAGAAGTGA (SEQ ID NO:33)) and an antisense primer Pk197a (AAATC-CATGGTGAAAGAAAAGTTCTTT-TATTTGCGACATCAACCGTATATCC(SEQ ID NO:34), NcoI site is in italic, the antisense codon for $Ala^{197}$ instead of $Lys^{197}$ underlined) to amplify a mutagenic fragment K197A. We used the primer Pn and an antisense primer Pr200a (AAATCCATGGTGAAAGAAAAGTTGCTT-TATTTTTGACATCAACCG(SEQ ID NO:35), the antisense codon for $Ala^{200}$ instead of $Arg^{200}$ underlined) to amplify a mutagenic fragment R200A. We used a sense primer Pnco (TTCACCATGGATTTCTAATATTCATG(SEQ ID NO:36), NcoI site is in italic) and an antisense primer Ppst (TAAATC-CTGCAGATACACTCCCACCAAT(SEQ ID NO:37), PstI site is in italic) to amplify a fragment designated NP. After digestion by NcoI, the fragments K197A and NP, and R200A and NP were ligated. The primers Pn and Ppst were used to amplify the ligated products of K197A+NP and R200A+NP, respectively, resulting in the mutagenized fragments U2-K197A and U2-R200A.

To amplify the group R mutants, PrAg-L1 expression plasmid pYS5-PrAg-L1[17] was used as a template. We used primer Pn and an antisense primer Pr178a-1 (AGGGATCCCAT-CATTGTCAGCGTCTGGAACCGTAGGTCC(SEQ ID NO:38), BamHI site is in italic, the antisense codon for $Ala^{178}$ instead of $Arg^{178}$ underlined) to amplify a mutagenic fragment R178A-1. We used a sense primer Pr178a-2 (TGG-GATCCCTGATTCATTAGAGGTAGAAGG(SEQ ID NO:39), BamHI site is in italic, the codon for $Ala^{178}$ instead of $Arg^{178}$ underlined) and the primer Ppst to amplify a fragment R178A-2. After digestion by BamHI, the fragments R178A-1 and R178A-2 were ligated. The primers Pn and Ppst were used to amplify their ligated product, resulting in the mutagenized fragments L1-R178A.

We used the primer Pn and Ppst to amplify a fragment designated PP. We used a sense primer Pi210a (TTCAC-CATGGATTTCTAATGCTCATGAAAAGAAAGG(SEQ ID NO:40), NcoI site is in italic, the codon for $Ala^{210}$ instead of $Ile^{210}$ underlined) and an antisense primer Pli4 (ACGTT-TATCTCTTATTAAAAT(SEQ ID NO:41)) to amplify a mutagenic fragment I210A. We used a sense primer Pk214a (TTCACCATGGATTTCTAATATTCAT-GAAAAGGCAGGATTAACCAAATATA(SEQ ID NO:42), NcoI site is in italic, the codon for $Ala^{214}$ instead of $Lys^{214}$ underlined) and the primer Pli4 to amplify a mutagenic fragment K214A. After digestion by NcoI, the fragments I210A and PP, and I214A and PP were ligated. Primers Pn and Pli4 were used to amplify the ligated products of I210A+PP and I214A+PP, respectively, resulting in the mutagenized Fragments L1-I210A and L1-K214A.

The 670-bp HindIII/PstI fragments from the digests of U2-K197A, U2-R200A, L1-R178A, L1-I210A, and L1-K214A were cloned between the HindIII and PstI sites of pYS5, a wild-type PrAg expression plasmid. The resulting mutated PrAg proteins were accordingly named PrAg-U2-K197A, PrAg-U2-R200A, PrAg-L1-R178A, PrAg-L1-I210A, and PrAg-L1-K214A. We also constructed PrAg-R200A and PrAg-I210A, using procedures similar to those described above except that plasmid pYS5 was used as a template for PCR. The sequences of all mutated PrAg constructs were confirmed by DNA sequencing.

Expression and purification of PrAg proteins: Plasmids encoding the constructs described above were transformed into the non-virulent strain *Bacillus anthracis* BH445, and transformants were grown in FA medium (Rosovitz, M. J. et al., *J Biol. Chem. (*2003)) with 20 μg/ml kanamycin and 10 μg/ml chloramphenicol for 12 h at 37° C. The proteins were secreted into the culture supernatants at 20-40 mg/L, precipitated by ammonium sulfate, and purified by gel filtration chromatography to one prominent band at the expected molecular mass of 83 kDa, which co-migrated with wild-type PrAg in SDS-PAGE.

Cytotoxicity assays with MTT: Human melanoma A2058 cells were grown and maintained as described previously (Liu, S. et al., *Cancer Res.* 60, 6061-6067 (2000)). Cells were cultured in 96-well plates to approximately 50% confluence. Then the cells were pre-incubated for 30 min with 1.9 nM pro-uPA (#107, American Diagnostica Inc., Greenwich, Conn.) with or without PAI-1 (46 nM) (#1094, American Diagnostica Inc.) or TIMP-2 (0.4 μM) (Cat. No. PF021, Calboichem, San Diego, Calif.). Various concentrations of PrAg proteins or mixtures of them, combined with FP59 (1.9 nM), were added to the cells to give a total volume of 200 μl/well. Cell viability was assayed after incubation for 48 h using MTT (3-[4,5-dimethylthiazol-2-yl]-2,5-diphenyltetrazolium bromide) as described previously (Liu, S. et al., *Cancer Res.* 60, 6061-6067 (2000)).

Murine macrophage RAW264.7 cells were grown in Dulbecco's Modified Essential Medium (DMEM) with 0.45% glucose, 10% fetal bovine serum (FCS), 2 mM glutamine, and 50 μg/ml gentamicin. RAW264.7 cells cultured in 96-well plates to approximately 80% confluence were incubated with 6 nM of different PrAg proteins or their combinations and various amounts of LF (0-12 nM) for 3.5 h, and then MTT was added to determine cell viability.

PrAg-mediated LF-binding assay: CHO cells grown in 24-well plates were incubated with 12 nM of different PrAg proteins or their combinations and 1.2 nM of LF for 2 h at 37° C. Then the cells were washed and lysed in a modified RIPA lysis buffer containing protease inhibitors (Liu, S. & Leppla, S. H., *J. Biol. Chem.* 278, 5227-5234 (2003)). The cell lysates were analyzed by SDS-PAGE followed by Western blotting using a rabbit anti-PrAg antiserum (serum #5308, made in our laboratory) to detect PrAg binding and processing, or a rabbit anti-LF antiserum (serum #5309, made in our laboratory) to detect LF binding.

In vitro cleavage of PrAg proteins by furin, uPA and MT1-MMP: Reaction mixtures of 50 µl containing 3 µg of the PrAg proteins were incubated at 37° C. with 1 unit of furin (Product No. F2677, Sigma, Saint Louis, Mo.), 0.3 µg uPA (#124, American Diagnostica Inc., Greenwich, Conn.), or 0.3 µg soluble MT1-MMP (Calbiochem). Digestion with furin and uPA was performed as described (Liu, S. et al., *J. Biol. Chem.* 276, 17976-17984 (2001)). Cleavage with MT1-MMP was done in 50 mM HEPES, pH 7.5, 10 mM $CaCl_2$, 200 mM NaCl, 0.05% Brij35, 50 µM $ZnSO_4$. Aliquots withdrawn at intervals were analyzed by SDS-PAGE, and proteins were visualized by Western blot analysis using the rabbit anti-PrAg polyclonal antiserum (serum #5308).

Determination of the maximum tolerated doses of recombinant toxins: Male and female C57BL/6J mice (The Jackson Laboratory) aged between 6-8 weeks were used in this study. The mice were housed in a pathogen-free facility certified by the Association for Assessment and Accreditation of Laboratory Animal Care International, and the study was carried out in accordance with institutional guidelines. The maximum tolerated doses of PrAg proteins were determined using a dose escalation protocol aimed at minimizing the number of the mice to be used. The mice (n=5) in each group were anesthetized by Isoflurane inhalation and injected intraperitoneally with three doses of various PrAg proteins combined with 3 µg FP59 in 500 µl PBS at days 0, 3, and 6. The mice were monitored closely for signs of toxicity including weight loss, inactivity, loss of appetite, inability to groom, ruffling of fur, and shortness of breath, and euthanized by $CO_2$ inhalation at the onset of obvious malaise. The maximum tolerated doses for three administrations (MTD3) were determined as the highest doses in which outward disease was not observed in any mice within a 14-day period of observation. The significance of differences between treatment groups was determined by two-tailed Chi-square analysis.

Tumor transplantation and toxin treatment experiments: The transplanted murine B16-BL6 melanoma, T241 fibrosarcoma and LL3 Lewis lung carcinoma were established subcutaneously as described previously (Liu, S. et al., *Proc. Natl. Acad. Sci. U.S.A.* 100, 657-662 (2003)). PrAg proteins combined with 0.5 µg FP59 in 100 µl PBS or PBS 100 µl alone were injected intradermally adjacent to the tumor nodule when the tumors had reached a size ranging from approximately 0.1-0.8% of total body mass (day 0) and again at days 3 and 6. The longest and shortest tumor diameter was determined daily by calipation by an investigator unaware of treatment group, and the tumor weight was calculated using the formula milligrams=(length in mm×[width in mm]$^2$)/2 (Geran, R. I. et al. *Cancer Chemother. Rep.* 3, 1 (1972)). The experiment was terminated when one or more mice in a treatment group presented frank tumor ulceration or exceed 10% of body weight. The significance of differences in tumor size was determined by two-tailed Student's t-test.

Example 2

Two Pairs of Complementary Mutant PrAg Antigens Exhibit Tumoricidal Activity in vitro FIG. 2 illustrates data demonstrating the cytotoxicity of two pairs of complementary mutant PrAg proteins to human melanoma A2058 cells. Three mutant PrAg proteins were generated: U-R200A; M-I210A; and M-K214A. U-R200A has the native furin cleavage site of PrAg substituted for a cleavage site for urokinase plasminogen activator and arginine at position 200 substituted for alanine. M-I210A has the native furin cleavage site of PrAg substituted for a cleavage site for matrix metalloproteinase and isoleucine at position 210 substituted for alanine M-K214A has the native furin cleavage site of PrAg substituted for a cleavage site for matrix metalloproteinase and lysine at position 214 substituted for alanine None of these modified PrAg monomers are able to homo-oligomerize to form a functional PrAg that binds LF. Human melanoma A2058 cells were contacted with the following ratios of either U-R200A and M-I210A or U-R200A and M-K214A: 6:0; 5:1; 4:2; 3:3; 2:4; 1:5, or 0:6. The cells were also contacted with FP59 (i.e., anthrax lethal factor fused to the ADP ribosylation domain of Pseudomonas exotoxin A) at 100 ng/ml. Cytotoxicity to the tumor cells was demonstrated with a wide range of ratios from 1:5 to 5:1 for both the U-R200A:M-I210A and U-R200A:M-K214A. The results are shown in FIG. 2

Example 3

Two Complementary Mutant PrAg Antigens Exhibit Tumoricidal Activity in vivo

Figure 3:
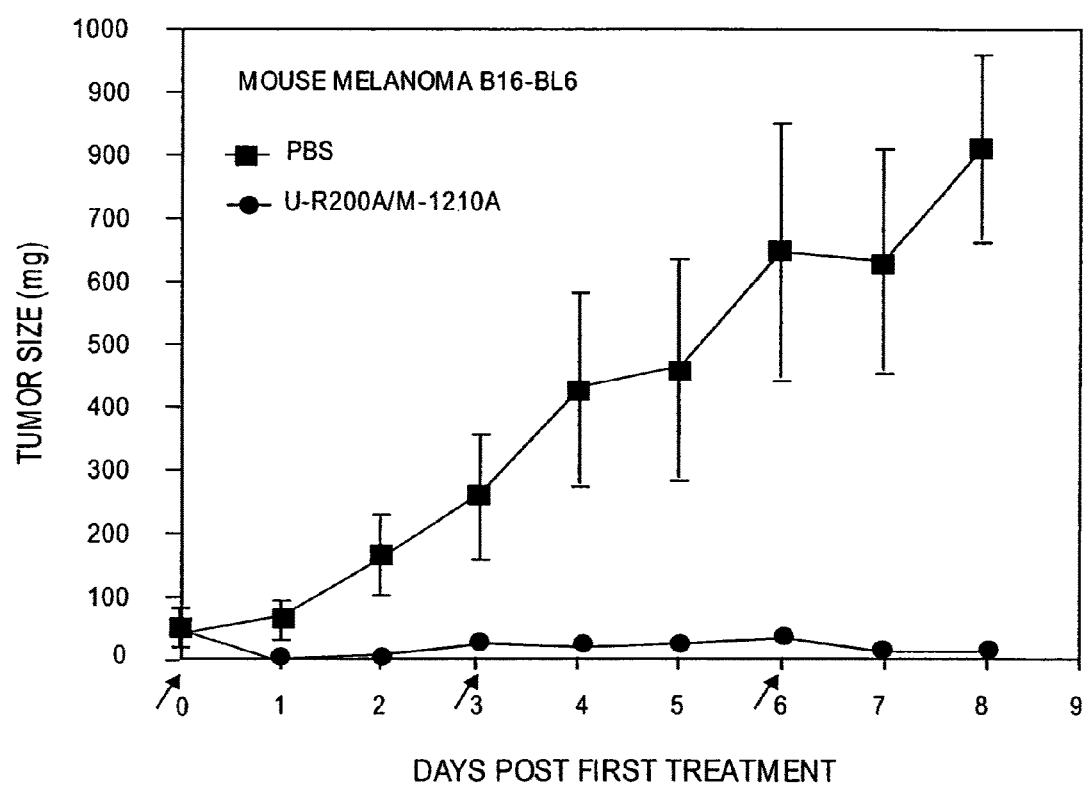
FIG. 3 illustrates data demonstrating tumoricidal activity of two complementary mutant PrAg proteins to a mouse melanoma cell B16-BL6 in a mouse tumor model. A combination f U-R200A and M-I210A was used in these experiments. Mutant PrAg proteins and FP59 were injected on days 0, 3, and 6: U-R200A=10 µg; M-I210A=5 µg and FP59=1.2 µg.

Two complementary mutant PrAg proteins (U-R200A and M-I210A) were generated. Neither mutant can homo-oligomerize and form a functional PrAg, but they are able to hetero-oligomerize and form a functional PrAg that can bind LF. A combination of U-R200A and M-I210A was used in these experiments. The mutant PrAg proteins and FP59 were injected into mice bearing melanoma cell B16-BL6 tumors on days 0, 3, and 6 as follows: U-R200A=10 µg; M-I210A=5 µg and FP59=1.2 µg. The results are shown in FIG. 3.

Example 4

Figure 1:
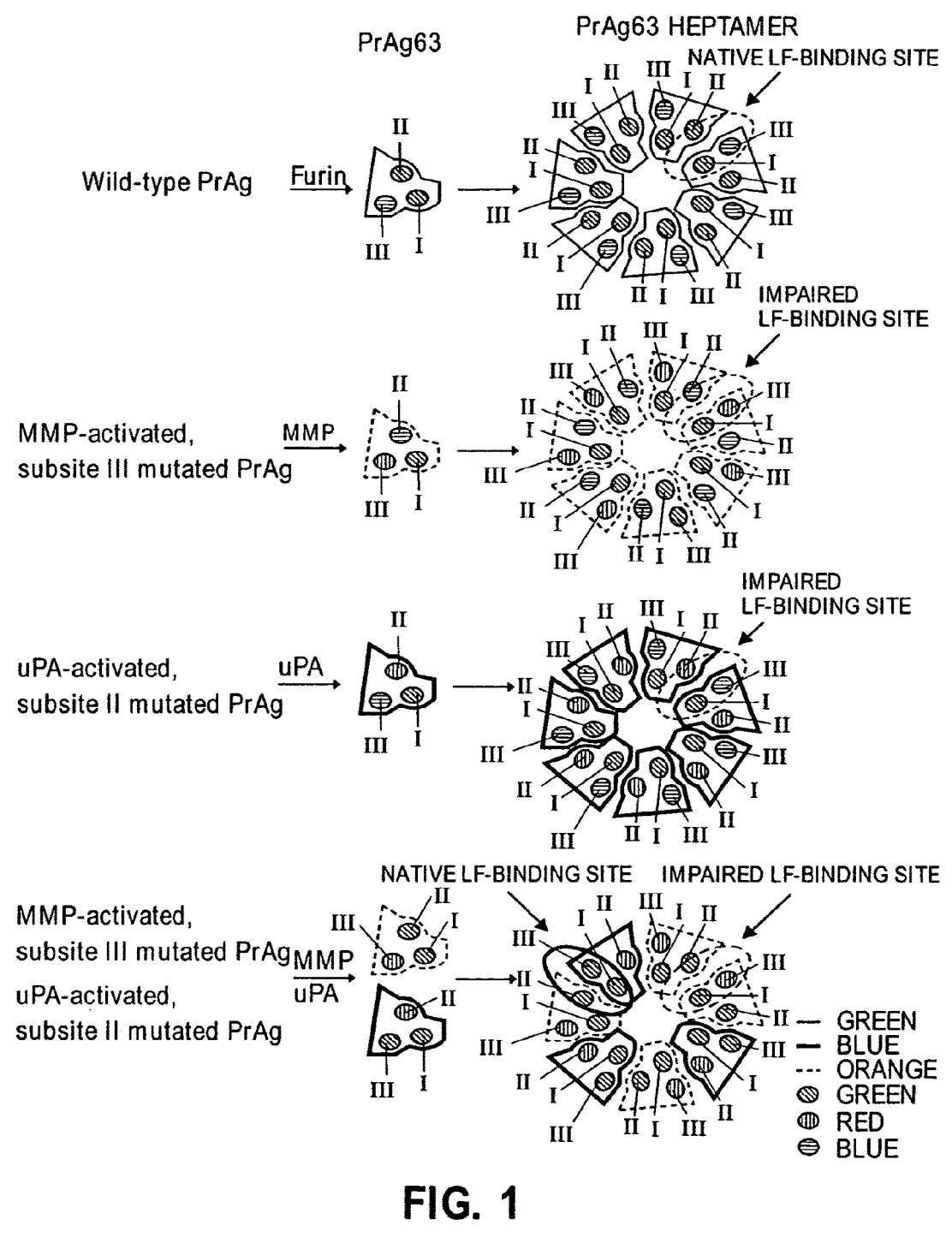

Generation of Mutated PrAg Proteins that Depend on Intramolecular Complementation for Toxicity We recognized that the multimeric nature of the PrAg heptamer offers several opportunities for achieving high cell-type specificity. The strategy used in these studies is diagrammed in FIG. 1. The top row shows the assembly of native PrAg63 into a heptamer having functional LF binding sites. The second row shows a PrAg mutant altered in the protease cleavage site so as to be dependent on MMP activity, and containing a second mutation that inactivates the LF binding subsite III. Binding of this PrAg to an MMP-expressing cells leads to assembly of a heptamer in which every LF binding site contains the inactivating subsite III mutation. The third row in FIG. 1 shows a PrAg protein requiring uPA activation and having an inactivating LF binding subsite II mutation. It would also produce an impaired heptamer. However, adding a mixture of these PrAg proteins to a cell having both MMP and uPA activities would generate two PrAg63 proteins that could randomly assemble into a heptamer in which some (up to three) of the LF binding sites would bind LF. An interesting feature of this geometry is that adjacent functional sites cannot occur, so the steric constraint on use of adjacent sites in the native heptamer will not prevent use of latent sites, and all sites formed by intermolecular complementation will be able to bind LF proteins.

To determine whether intermolecular complementation can restore an active LF binding site, we introduced previously described LF-binding site mutations into PrAg while retaining the native furin site. The mutated PrAg proteins PrAg-R200A and PrAg-I210A contain alanine substitutions at, respectively, the LF-binding subsite II residue $Arg^{200}$ and the subsite III residue $Ile^{210}$ (Table 1).

TABLE 1

Properties and maximum tolerated doses of the PrAg proteins when injected intraperitoneally at days 0, 3, and 6

| PrAg proteins or their combination | Proteolytic cleavage | Group L mutation Subsite II | Group R mutation Subsite I | Group R mutation Subsite III | MTD3 (µg) FP59 = 3 µg |
|---|---|---|---|---|---|
| PrAg | Furin | | | | 0.25 |
| PrAg-R200A | Furin | R200A | | | ND |
| PrAg-I210A | Furin | | | I210A | ND |
| PrAg-L1 | MMP | | | | 4 |
| PrAg-L1-R178A | MMP | | R178A | | ND |
| PrAg-L1-I210A | MMP | | | I210A | 50 |
| PrAg-L1-K214A | MMP | | | K214A | ≧50 |
| PrAg-U2 | uPA | | | | 10 |
| PrAg-U2-K197A | uPA | K197A | | | ND |
| PrAg-U2-R200A | uPA | R200A | | | ≧100 |
| PrAg-U2-R200A | uPA | R200A | | | 30 |
| PrAg-L1-I210A | MMP | | | I210A | 15 |
| PrAg-U2-R200A | uPA | R200A | | | 30 |
| PrAg-L1-K214A | MMP | | | K214A | 15 |

ND: not done. PrAg-L1: MMP-activated PrAg protein with furin site RKKR(SEQ ID NO:26) changed to MMP cleavage sequence GPLGMLSQ(SEQ ID NO:25)(Liu, S. et al., *J. Biol. Chem.* 276, 17976-17984 (2001)). PrAg-U2: uPA-activated PrAg protein with furin site RKKR(SEQ ID NO:26) changed to uPA cleavage sequence PGSGRSA(SEQ ID NO:23)(Liu, S. et al., *J. Biol. Chem.* 276, 17976-17984 (2001); Liu, S. et al., *Proc. Natl. Acad. Sci. U. S. A.* 100, 657-662 (2003)).

These mutated proteins are designated as belonging to groups L and R, respectively, indicating the location of the mutations relative to the monomer-monomer interface. These mutated PrAg proteins were expressed in the non-virulent *B. anthracis* strain BH445, purified, and characterized. PrAg-R200A and PrAg-I210A, just like wild-type PrAg, bound to Chinese hamster ovary (CHO) cells, were processed by furin to produce PrAg63 proteins, and formed SDS-resistant heptamers (FIG. 4A), but they had significantly decreased abilities to bind LF (FIG. 4A). However, when PrAg-I210A and PrAg-R200A were applied together to CHO cells, LF-binding ability was substantially regained (FIG. 4A). Therefore, PrAg-R200A and PrAg-I210A display intermolecular complementation in formation of LF-binding PrAg heptamers. The decreased LF binding observed for the PrAg-R200A/PrAg-I210A mixture is expected (FIG. 4A), because the PrAg63 heptamer formed from wild-type PrAg is able to bind three LF molecules, while that formed from the complementing PrAg proteins will on average contain fewer than three functional sites (FIG. 1).

Figure 4E:
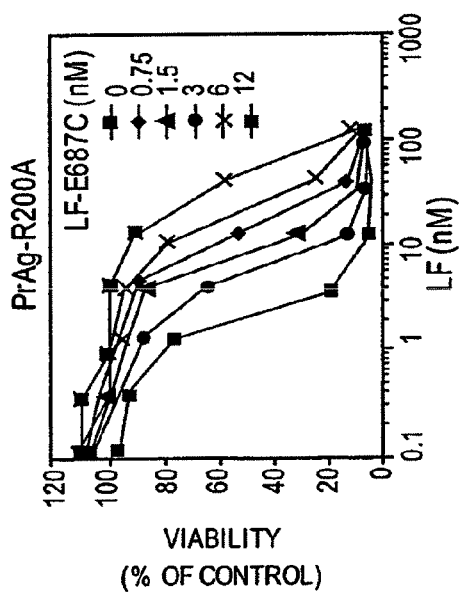
FIG. 4E illustrates data demonstrating LF binding to RAW264.7 cells incubated with various amounts of LF in the presence of PrAg-I210A.

In agreement with the results of FIG. 4A, cytotoxicity measurements showed that PrAg-R200A and PrAg-I210A demonstrated intermolecular complementation in killing of the murine macrophage cell line RAW264.7 by LF (FIG. 4C). The mixture of PrAg-R200A and PrAg-I210A had an $EC_{50}$ for LF of 0.2 nM (18 ng/ml), 14- and 10-fold lower than that of PrAg-R200A (2.7 nM) and PrAg-I210A (2.0 nM) (FIGS. 4D and 4E), respectively, and approaching the potency found with wild-type PrAg, 0.05 nM (4.5 ng/ml) (FIG. 4B).

Figure 4F:
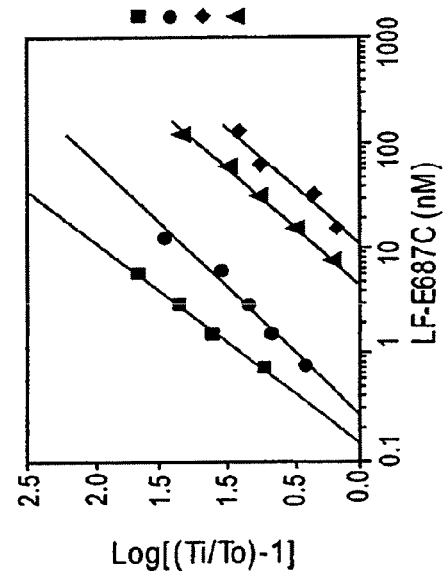
FIG. 4F illustrates Schild Plot analyses data identifying the $K_d$ of LF-E687C to the heptamers formed by the modified PrAg proteins.
Figure 6:
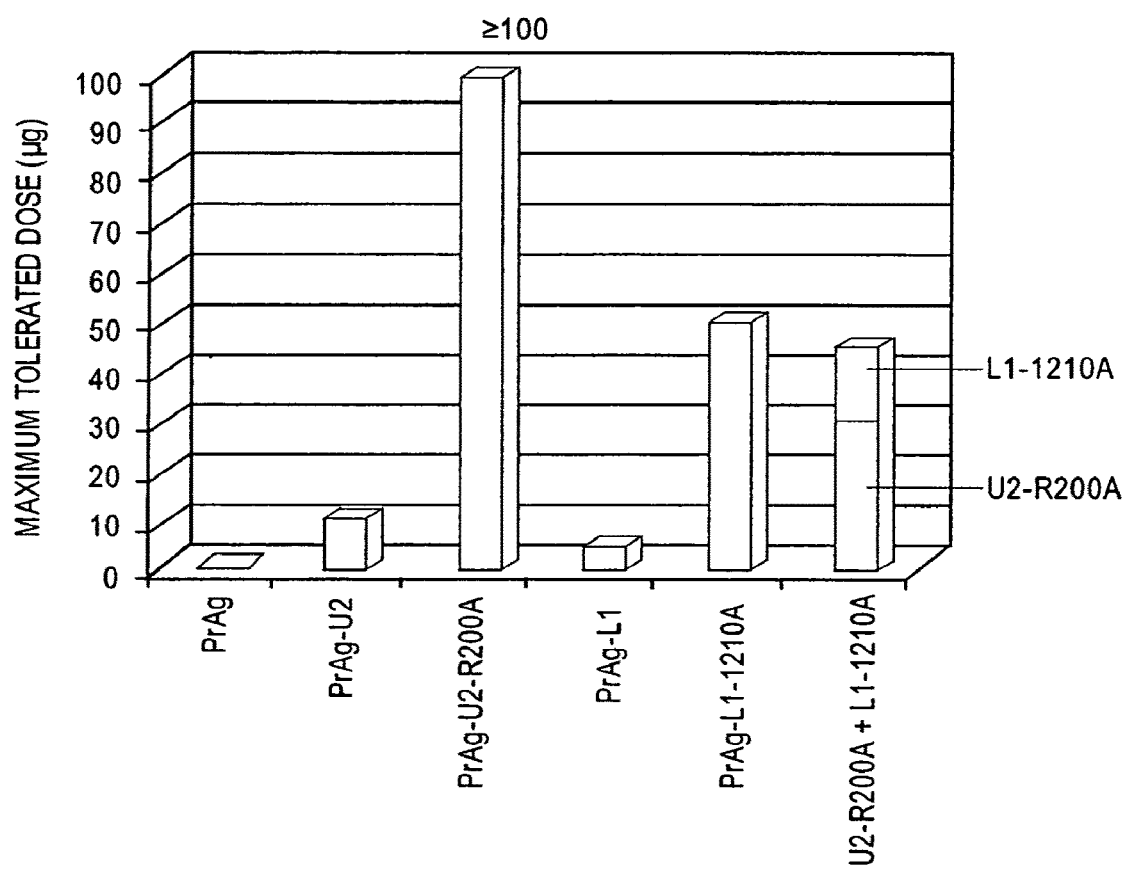
FIG. 6 illustrates data demonstrating the maximum tolerated doses of PrAg proteins in mice.
Figures 7A, 7B, 7C:
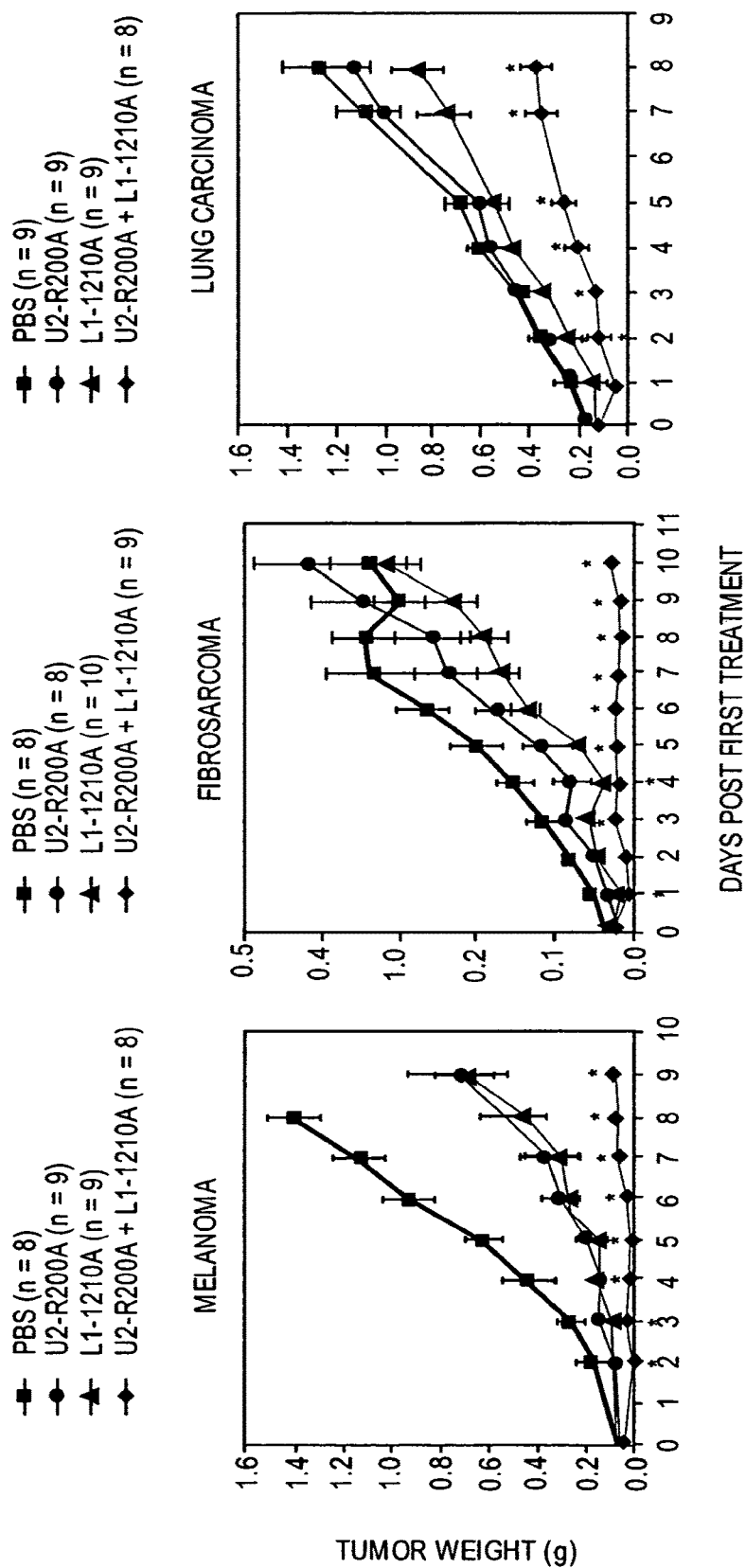
FIG. 7A illustrates data from mice bearing B16-BL6 melanomas.
FIG. 7B illustrates data from mice bearing T241 fibrosarcomas.
FIG. 7C illustrates data from mice bearing LL3 Lewis lung carcinomas. The weight of intradermal tumor nodules is expressed as mean tumor weight±the SEM. *, Significance (p<0.05) between the treatments using the combination of PrAg-U2-R200A and PrAg-L1-I210A and using PrAg-U2-R200A or PrAg-L1-I210A alone.

The affinities of the LF binding sites present on the PrAg heptamers formed by these mutated PrAg proteins were directly measured by competitive Schild Plot analyses (Ittelson, T. R. & Gill, D. M., *Nature* 242, 330-332 (1973); Malatynska, E. et al., *Pharmacology* 57, 117-123 (1998); Varughese, M. et al., *Infect. Immun.* 67, 1860-1865 (1999)). Cytotoxicity assays were performed using as a competitor a mutated, non-toxic LF protein, LFE687C[28], that contains a cysteine substitution at the catalytic site $Glu^{687}$ (FIGS. 4B-4F). Addition of fixed concentrations of LF-E687C shifted the cytotoxicity dose-response curves rightward ((FIGS. 4B-4D). A reciprocal plot of the midpoints of the dose response curves yields dissociation constants for the affinity of LF-E687C to the heptamers formed from the PrAg proteins (FIG. 4F). This analysis showed that the Kd for LF-E687C binding to the complementing mixture of PrAg-R200A and PrAg-I210A is 0.26 nM, 39- and 18-fold lower than those of the individual proteins (10.3 nM for PrAg-R200A, 4.7 nM for PrAg-I210A), and approaching that of wild-type PrAg, 0.15 nM (FIG. 4F).

Example 5

Killing Tumor Cells by Engineered Intermolecularly Complementing PrAg Proteins that Require Both uPA and MMP Activation The evidence that intermolecular complementation does occur in this system implied that a PrAg mixture could be created that would be toxic only to tumor cells expressing two distinct cell-surface proteolytic activities. To test this hypothesis, PrAg proteins were produced that require activation by either uPA or MMP activities and which incorporate the LF-binding subsite mutations. Thus, the previously characterized uPA-activated PrAg-U2 (with the furin site RKKR(SEQ ID NO:26) changed to uPA cleavage sequence PGSGRSA) (SEQ ID NO:23)) (Liu, S. et al., *J. Biol. Chem.* 276, 17976-17984 (2001); Liu, S. et al., *Proc. Natl. Acad. Sci. U.S.A.* 100, 657-662 (2003)), was further mutated to yield the group L proteins PrAg-U2-K197A and PrAg-U2-R200A (Table 1 and FIG. 1). Similarly, the previously described PrAg-L1 protein (with the furin site changed to MMP cleavage sequence GPLGMLSQ(SEQ ID NO:25)) (Liu, S. et al., *J. Biol. Chem.* 276, 17976-17984 (2001)) was further mutated to yield the group R proteins PrAg-L1-R178A, PrAg-L1-I210A, and PrAg-L1-K214A. These PrAg proteins and their properties as determined below are summarized in Table 1.

To determine whether these PrAg proteins require intermolecular complementation to kill tumor cells, PrAg proteins from the L and R groups were added individually and in combination to human melanoma A2058 cells along with the effector protein FP59. In tumor tissues, cancer cells typically overexpress uPAR, while either the cancer cells or the adjacent tumor stromal cells express pro-uPA, which is activated on the cancer cell surface after binding to uPAR (Dano, K. et al., *APMIS* 107, 120-127 (1999)). A2058 cells express both uPAR and MMP but do not express pro-uPA under the current culture condition (Liu, S. et al., *Cancer Res.* 60, 6061-6067 (2000); Liu, S. et al., *J. Biol. Chem.* 276, 17976-17984 (2001)). Therefore, pro-uPA was added to mimic the in vivo situation. The results showed that the group L protein PrAg- U2-R200A complemented the group R proteins, in particular PrAg-L1-I210A, to efficiently kill A2058 cells in a wide range of molar ratios from 1:5 to 5:1 (FIG. 5A). In contrast, PrAg-U2-R200A, PrAg-L1-I210A(i.e., PA-M-I210A), PrAg-L1-K214A (i.e., PA-M-K214A), and PrAg-L1-R178A (i.e., PA-M-R178A) killed<50% of the tumor cells when used alone at high concentrations (7.2 nM), demonstrating that their cytotoxic action is greatly increased by intermolecular complementation.

To verify that the cytotoxicity of the PrAg-U2-R200A and PrAg-L1-I210A mixture is dependent on both uPA and MMP activities, we first determined the in vitro susceptibility of the proteins to cleavage by their corresponding purified proteases. Only wild-type PrAg could be efficiently cleaved by furin to produce the PrAg63 fragment. Wild-type PrAg also showed a low degree of susceptibility to uPA, as reported previously (Liu, S. et al., *J. Biol. Chem.* 276, 17976-17984 (2001)), but was completely resistant to MT1 (membrane-type 1)-MMP. Moreover, PrAg-L1-I210A was cleaved only by MT1-MMP, and PrAg-U2-R200A was cleaved only by uPA.

We then used physiological inhibitors of each protease to confirm that the toxicity of the PrAg-U2-R200A and PrAg-L1-I210A mixture for A2058 cells requires both activating proteases. The effectiveness of the inhibitors was confirmed by showing inhibition of the parental proteins, PrAg-U2 by plasminogen activator inhibitor 1 (PAI-1), and PrAg-L1 by tissue inhibitor 2 of MMP (TIMP-2) (FIG. 5B) . Although the cell killing abilities of the individual LF binding site mutants were, as expected from FIG. 5A, less than 50%, their toxicities were clearly decreased by the corresponding protease inhibitors. Consistent with theory, the cytotoxicity of the combination of PrAg-U2-R200A and PrAg-L1-I210A was greatly inhibited by PAI-1 and TIMP-2 (FIG. 5B), with either one being sufficient, demonstrating that the toxicity was dependent on the simultaneous expression by the tumor cells of both uPA and MMP activities.

Example 6

PrAg Protein Mixtures that Depend on Two Distinct Proteases for Activation have Reduced Toxicity to Mice Toxin proteins having increased cell-type specificity are expected to have lower non-specific toxicity in vivo. To evaluate the toxicity of the PrAg proteins described here, various doses of mutated PrAg proteins were injected intraperitoneally into C57BL6 mice at days 0, 3, and 6 in the presence of 3 μg FP59. Wild-type PrAg was very toxic, having a maximum tolerated dose/three injections (MTD3) of 0.25 μg (Table 1, FIG. 6). PrAg-L1 was about 16-fold attenuated (MTD3=4 μg), and PrAg-U2 40-fold attenuated (MTD3=10 μg). The toxicities of PrAg-L1-I210A (MTD3=50 μg) and PrAg-U2-R200A (MTD3≧100 μg) were further decreased about 10-fold when compared with that of PrAg-L1 and PrAg-U2, respectively (Table 1, FIG. 6). Interestingly, PrAg-U2-R200A and PrAg-L1-I210A demonstrated an intermolecular complementation in toxicity to mice (MTD3=30+15 ug) (Table 1, FIG. 4), but the toxicity was substantially decreased compared with PrAg-U2 (MTD3=10 ug) and PrAg-L1 (MTD3=4 ug).

Example 7

Potent Tumoricidal Activity of the Complementing PrAg Proteins

We evaluated the PrAg-U2-R200A and PrAg-L1-I210A combination in treatment of three mouse tumors, B16-BL6 melanoma (Hart, I. R. *Am. J. Pathol.* 97, 587-600 (1979)), T241 fibrosarcoma (Liotta, L. A. et al., *Nature* 284, 67-68 (1980)), and LL3 Lewis lung carcinoma (Sugiura, K. & Stock, C. C., *Cancer Res* 15, 38-51 (1955); Bugge, T. H. et al., *Blood* 90, 4522-4531 (1997)). These murine tumors are highly malignant, disseminate rapidly when transplanted to syngeneic mice, and demonstrate a poor response to conventional treatment. Mice bearing solid intradermal tumor nodules constituting approximately 0.1 to 0.8% of the total body mass were treated with PBS, 6 μg PrAg-U2-R200A (plus 0.5 μg FP59), 6 μg PrAg-L1-I210A (plus 0.5 μg FP59), or with a combination of 3 μg PrAg-U2-R200A and 3 μg PrAg-L1-I210A (plus 0.5 μg FP59) at day 0, 3, and 6. The combination of PrAg-U2-R200A and PrAg-L1-I210A had strong anti-tumor activity, causing reductions in tumor size of 94% ($p<0.001$) in B16-BL6 melanoma, 92% ($p<0.001$) for T241 fibrosarcoma, and 71% ($p<0.001$) for Lewis lung carcinoma, as compared to PBS-treated tumors at the time the control mice were euthanized due to the heavy tumor burden or extensive ulceration (day 8 for melanoma and carcinoma, day 10 for fibrosarcoma) (FIGS. 7A-7C). In contrast, the tumors showed little or no response to treatment with the individual proteins, either PrAg-U2-R200A [65% reduction for melanoma ($p<0.005$), no reduction for fibrosarcoma and lung carcinoma ($p=0.36$)] or PrAg-L1-I210A [67% reduction ($p<0.005$) melanoma, no reduction for fibrosarcoma, 30% reduction for carcinoma ($p>0.05$)]. These data demonstrate that the potent tumoricidal activity of these engineered PrAg proteins requires their intermolecular complementation.

Example 8

Cell Binding Assay for Identification of Additional Functional Modified Bacterial Toxins that Bind to Effector Molecules Additional functional modified bacterial toxins that bind to effector molecules can be identified using the cell binding assay described in, e.g., Mogridge et al., *PNAS USA* 99(10): 7045-7048 (2002), or a modification thereof. Briefly, CHO cells are incubated in ice with $2\times10^{-8}$M modified PrAg monomers for 2 hours, washed twice with PBS, incubated with $^{35}$S-labeled lethal factor (LF) for 2 hours, washed twice with PBS. The modified PrAg monomers, when homo-oligomerized are unable to bind LF. Modified PrAg monomers which are complementary will hetero-oligomerize to form functional heptamers and bind the labeled LF to effect LF internalization into the cell. The amount of radioactive LF in the cells is detected on a scintillation counter. Trypsin-nicked PrAg is used as a positive control. Modifications of this assay, e.g., using modified monomers from any bacterial toxin can conveniently be used to identify complementary modified bacterial toxin monomers that can hetero-oligomerize to form functional modified bacterial toxins which bind effector molecules.

Example 9

Oligomerization Assay for Identification of Additional Monomer Oligomerization Sites in Modified Bacterial Toxins Additional monomer oligomerization sites in modified bacterial toxins can be identified using the oligomerization assay described in, e.g., Cunningham et al., *PNAS USA* 99(10):7049-7053 (2002) or a modification thereof. Briefly, Briefly, CHO cells are incubated in ice with $2\times10^{-8}$M modified PrAg monomers for 2 hours, washed twice with PBS, incubated with $^{35}$S-labeled lethal factor (LF) for 2 hours, washed twice with PBS. The modified PrAg monomers are unable to homo-oligomerize to form functional PrAg heptamers that bind LF. Modified PrAg monomers which are complementary will hetero-oligomerize to form functional heptamers and bind the labeled LF to effect LF internalization into the cell. The amount of radioactive LF in the cells is detected on a scintillation counter. Trypsin-nicked PrAg is used as a positive control. Modifications of this assay, e.g., using modified monomers from any bacterial toxin can conveniently be used to identify complementary modified bacterial toxin monomers that can hetero-oligomerize to form functional modified bacterial toxins which bind effector molecules.

All publications, patents, patent applications, and Accession Nos. cited in this specification are herein incorporated by reference as if each individual publication, patent, patent application, or Accession No. were specifically and individually indicated to be incorporated by reference.

What is claimed is:

1. A method of treating a disease, said method comprising administering to a patient suffering from the disease a composition that comprises a first effector component of a multimeric bacterial protein toxin, the first effector component comprising at least a first modified monomer and a second modified monomer, wherein said first and second modified monomers form a heterooligomer, wherein said first and second modified monomers are different, and wherein said first and second modified monomers are generated by modification of a first and second unmodified monomers, respectively, the modification of each of said first and second unmodified monomers meeting at least one of the following criteria:
   (a) substitution of a native cell-recognition domain in said first or second unmodified monomer for a non-native cell-recognition domain, wherein cells characteristic of the disease are recognized by the non-native cell-recognition domain; and
   (b) substitution of a native proteolytic activation site in said first or second unmodified monomer for a non-native proteolytic activation site, wherein cells characteristic of the disease express a protease cleaving at the non-native proteolytic activation site.

2. The method of claim 1, wherein the modification of each of said first and second unmodified monomers further meets at least one of the following criteria:
   (c) at least one mutation made to said first unmodified monomer, whereby said first modified monomer can form a heterooligomer with said second modified monomer only; and
   (d) at least one mutation made to each of said first and second unmodified monomers, whereby a second effector component can bind only at a site formed by the interaction of said first modified monomer and said second modified monomer.

3. The method of claim 1, wherein said disease is a cancer.

4. The method of claim 3, wherein said cancer is selected from the group consisting of: a carcinoma, a sarcoma, a lymphoma, a leukemia, and a combination thereof.

5. The method of claim 4, wherein said cancer is selected from the group consisting of: melanoma, colon cancer, breast cancer, bladder cancer, thyroid cancer, liver cancer, pleural cancer, lung cancer, ovarian cancer, pancreatic cancer, head and neck cancer, kidney cancer, multiple myeloma, stomach cancer, brain cancer, Hodgkin's lymphoma, non-Hodgkin's lymphoma and a combination thereof.

6. The method of claim 1, wherein cells characteristic of said disease express at least two different proteolytic enzymes.

7. The method of claim 6, wherein each of the at least two different proteolytic enzymes is a metalloproteinase, a cysteine protease, an aspartic acid protease, a plasminogen activator, a kallikrein, a type 1 transmembrane serine protease, a type 2 transmembrane serine protease, or a GPI anchored serine protease.

8. The method of claim 1, wherein said disease is a viral infection.

9. The method of claim 8, wherein said viral infection is a member selected from the group consisting of: an HIV infection, a CMV infection, a HPV infection, a HBV infection, a HCV infection, a HSV infection, and a HZV infection.

10. The method of claim 1, wherein said disease is an autoimmune disease.

11. The method of claim 10, wherein said autoimmune disease is a member selected from the group consisting of: rheumatoid arthritis (RA), diabetes mellitus (DM), myasthenia gravis (MG), systemic lupus erythematosus (SLE), Grave's disease, and Addison's disease.

12. A method of targeting a cell, said method comprising contacting said cell with a composition that comprises a first effector component of a multimeric bacterial protein toxin, the first effector component comprising at least a first modified monomer and a second modified monomer, wherein said first and second modified monomers form a heterooligomer, wherein said first and second modified monomers are different, and wherein said first and second modified monomers are generated by modification of a first and second unmodified monomers, respectively, the modification of each of said first and second unmodified monomers meeting at least one of the following criteria:
   (a) substitution of a native cell-recognition domain in said first or second unmodified monomer for a non-native cell-recognition domain, wherein the non-native cell-recognition domain recognizes the cell; and
   (b) substitution of a native proteolytic activation site in said first or second unmodified monomer for a non-native proteolytic activation site, wherein the cell expresses a protease cleaving at the non-native proteolytic activation site.

13. The method of claim 12, wherein the modification of each of said first and second unmodified monomers further meets at least one of the following criteria:
   (c) at least one mutation made to each of said first and second unmodified monomers, whereby said first modified monomer can form a heterooligomer with said second modified monomer only; and
   (d) at least one modification made to each of said first and second unmodified monomers, whereby a second effector component can bind only at a site formed by the interaction of said first modified monomer and said second modified monomer.

14. The method of claim 12, wherein said cell is in a mammal.

15. The method of claim 12, wherein said cell is killed by said contacting.

16. The method of claim 12, wherein said cell is detected after said contacting.

17. The method of claim 12, wherein said cell is a virally infected cell.

18. The method of claim 12, wherein said cell is a cancer cell.

* * * * *